(12) United States Patent
Gadini et al.

(10) Patent No.: US 9,250,163 B2
(45) Date of Patent: Feb. 2, 2016

(54) MICROFLUIDIC DEVICES AND/OR EQUIPMENT FOR MICROFLUIDIC DEVICES

(75) Inventors: Costanzo Gadini, Frassineto Po (IT); Fulvio Cerutti, Ivrea (IT)

(73) Assignee: ELTEK S.P.A., Casale Monferrato (IT)

( * ) Notice: Subject to any disclaimer, the term of this patent is extended or adjusted under 35 U.S.C. 154(b) by 511 days.

(21) Appl. No.: 13/642,596

(22) PCT Filed: Apr. 20, 2011

(86) PCT No.: PCT/IB2011/051733
§ 371 (c)(1),
(2), (4) Date: Dec. 21, 2012

(87) PCT Pub. No.: WO2011/132164
PCT Pub. Date: Oct. 27, 2011

(65) Prior Publication Data
US 2013/0086980 A1  Apr. 11, 2013

(30) Foreign Application Priority Data
Apr. 20, 2010  (IT) .............................. TO2010O068 U

(51) Int. Cl.
| | | |
|---|---|---|
| *G01N 1/28* | (2006.01) | |
| *B01L 3/00* | (2006.01) | |
| *G01N 15/12* | (2006.01) | |
| *G01N 15/14* | (2006.01) | |

(52) U.S. Cl.
CPC ............ *G01N 1/28* (2013.01); *B01L 3/502753* (2013.01); *B01L 3/502761* (2013.01); *B01L 2200/028* (2013.01); *B01L 2200/0631* (2013.01); *B01L 2200/0652* (2013.01); *B01L 2200/0668* (2013.01); *B01L 2300/0681* (2013.01); *B01L 2300/0816* (2013.01); *B01L 2300/0877* (2013.01); *B01L 2400/086* (2013.01); *G01N 15/12* (2013.01); *G01N 2015/1486* (2013.01)

(58) Field of Classification Search
CPC . G01N 1/28; G01N 15/12; G01N 2015/1486; B01L 3/502753; B01L 3/502761; B01L 2200/028; B01L 2200/0631
See application file for complete search history.

(56) References Cited

U.S. PATENT DOCUMENTS

| | | |
|---|---|---|
| 6,150,180 A | 11/2000 | Parce |
| 2003/0023149 A1 | 1/2003 | Montemagno et al. |
| 2006/0035386 A1 | 2/2006 | Hattori et al. |
| 2008/0233607 A1 | 9/2008 | Yu et al. |
| 2008/0318324 A1 | 12/2008 | Chiu et al. |
| 2009/0283456 A1 | 11/2009 | Le Vot et al. |
| 2011/0087367 A1* | 4/2011 | Gadini et al. ................. 700/231 |

FOREIGN PATENT DOCUMENTS

| | | |
|---|---|---|
| EP | 2000807 A1 | 12/2008 |
| WO | 2008115626 A2 | 9/2008 |

OTHER PUBLICATIONS

International Search Report for PCT/IB2011/051733 dated Sep. 15, 2011.

* cited by examiner

*Primary Examiner* — Daniel S Larkin
(74) *Attorney, Agent, or Firm* — Heslin Rothenberg Farley Mesiti, PC; Victor Cardona

(57) ABSTRACT

A biomedical microfluidic device for separating a sub-population of particles from a first fluid, particularly a biological fluid, has means for separation and/or filtration of the fluid, which include a first microfluidic path defined in a first body of the device, a first inlet for introduction of a first fluid in the first path and at least a first outlet for discharge from the first path of a sample of fluid enriched in the sub-population of particles.

20 Claims, 36 Drawing Sheets

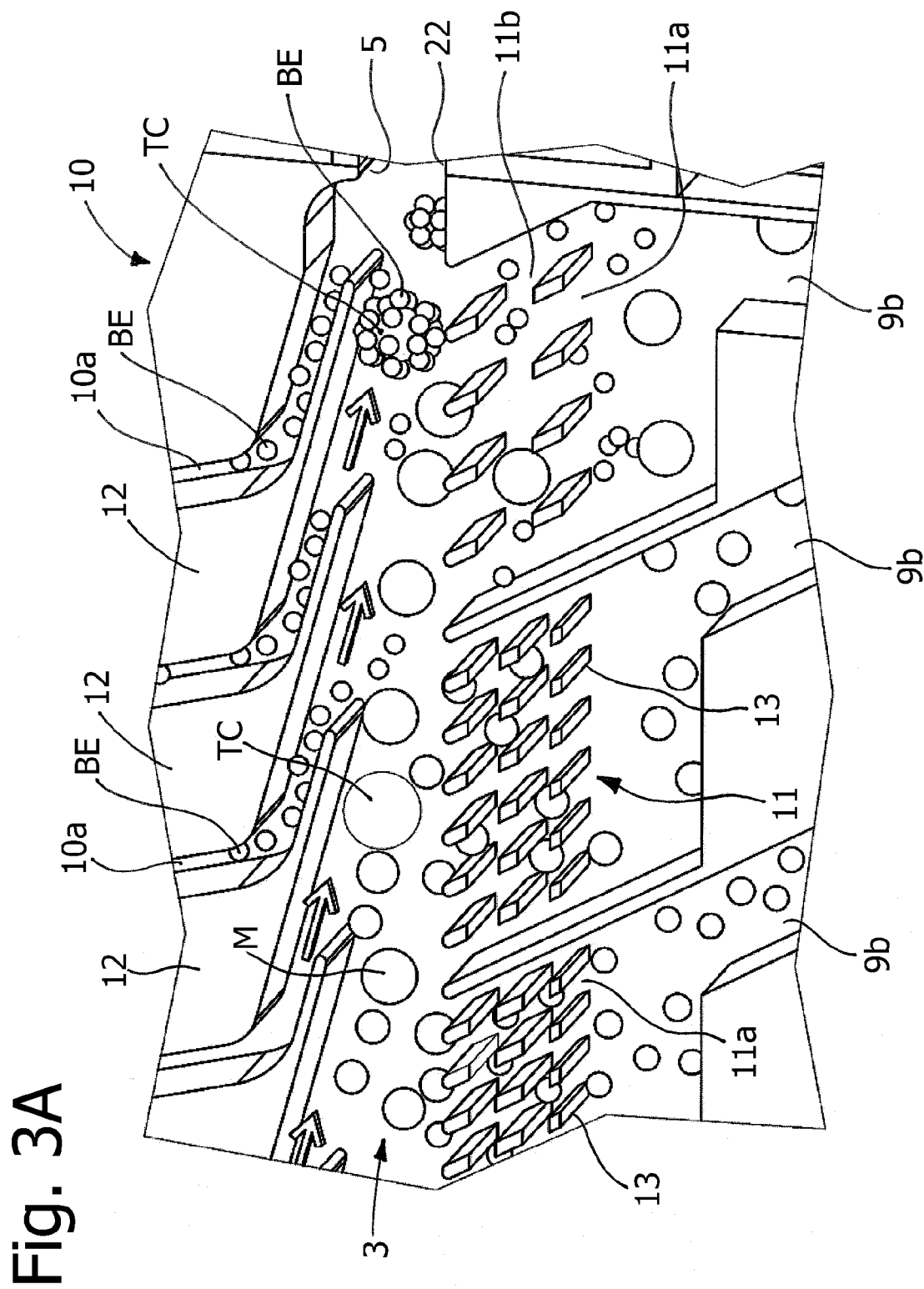

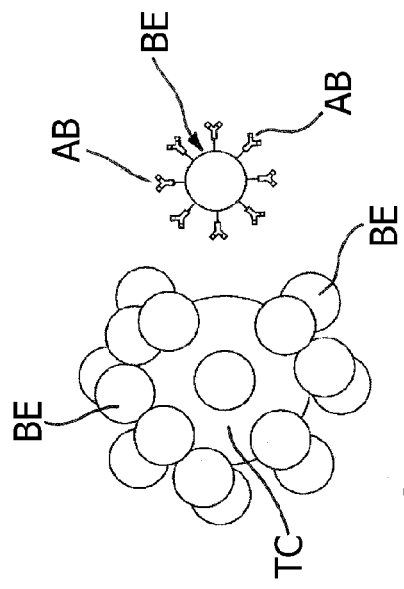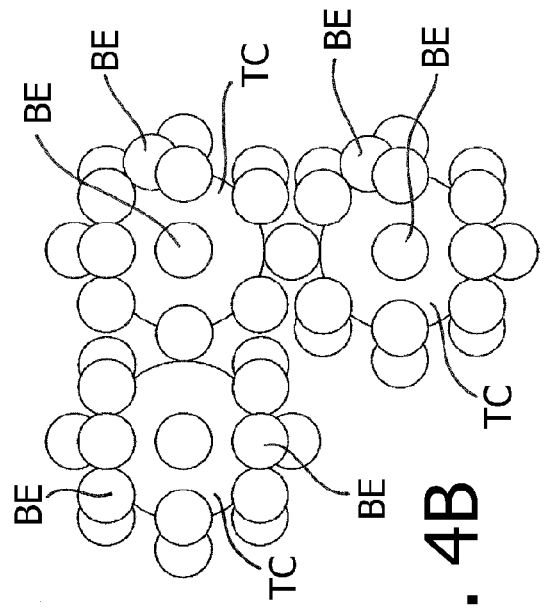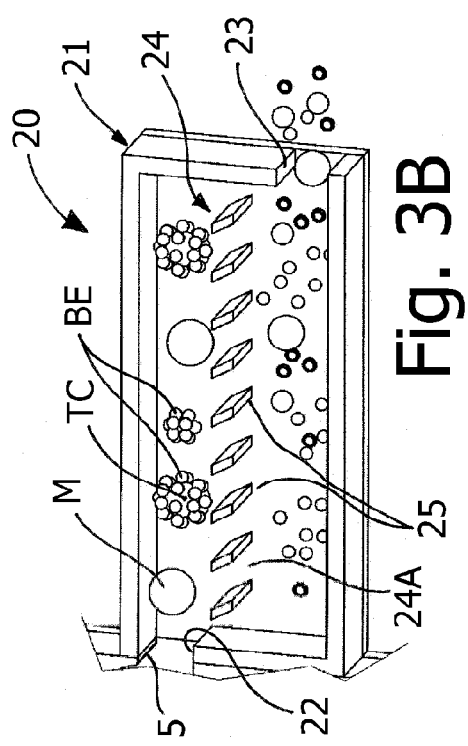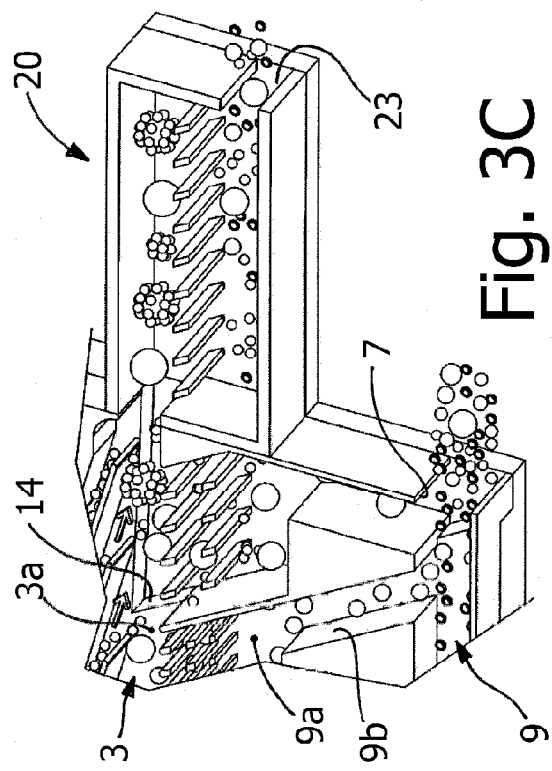

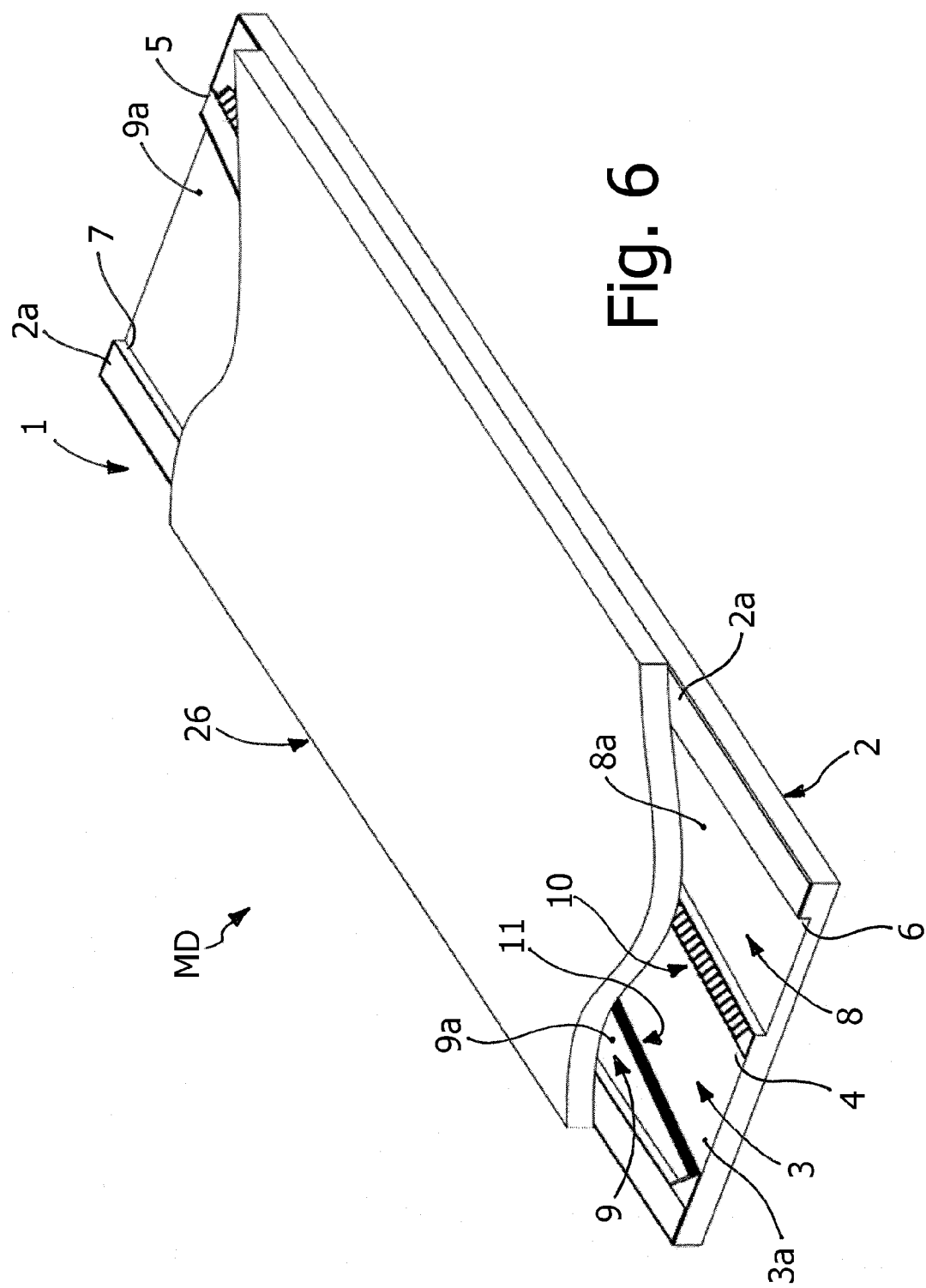

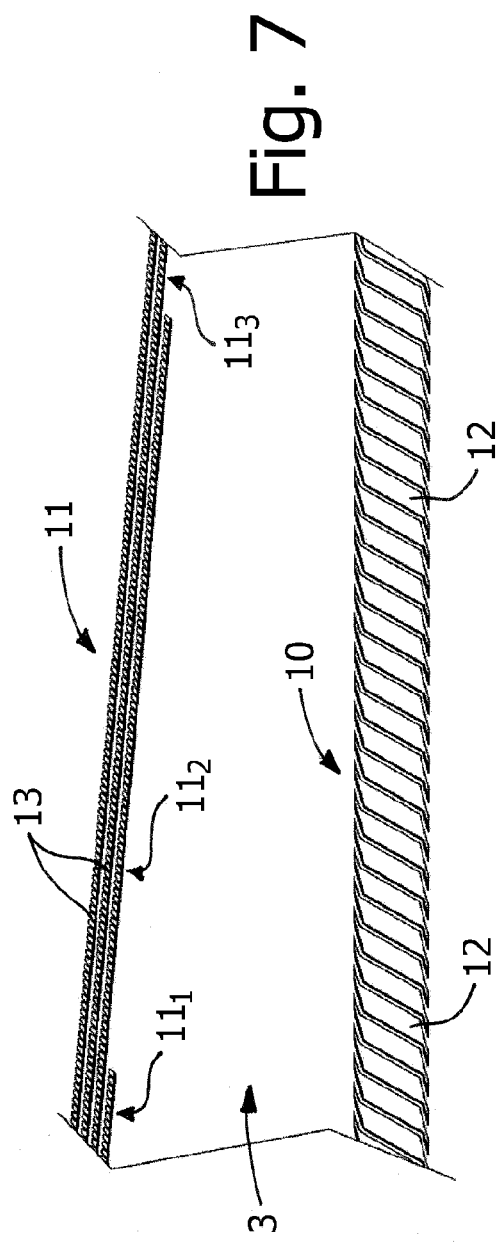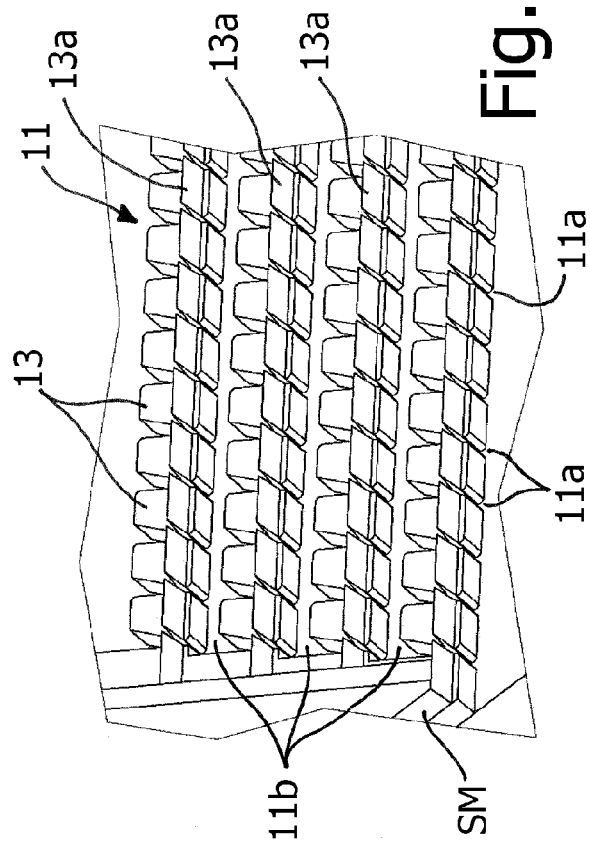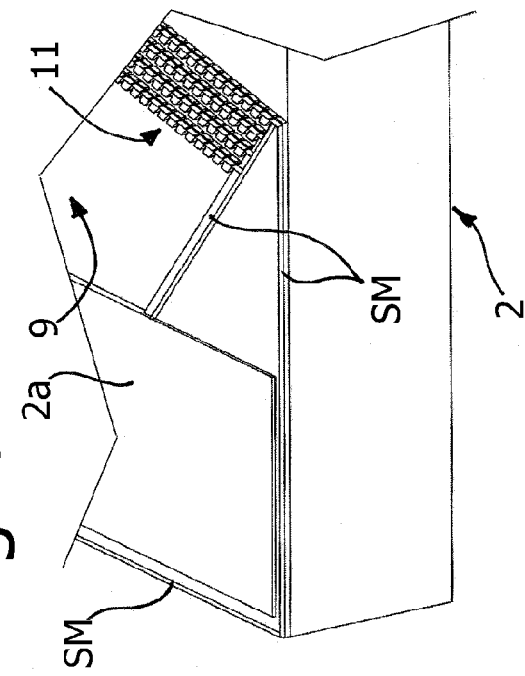

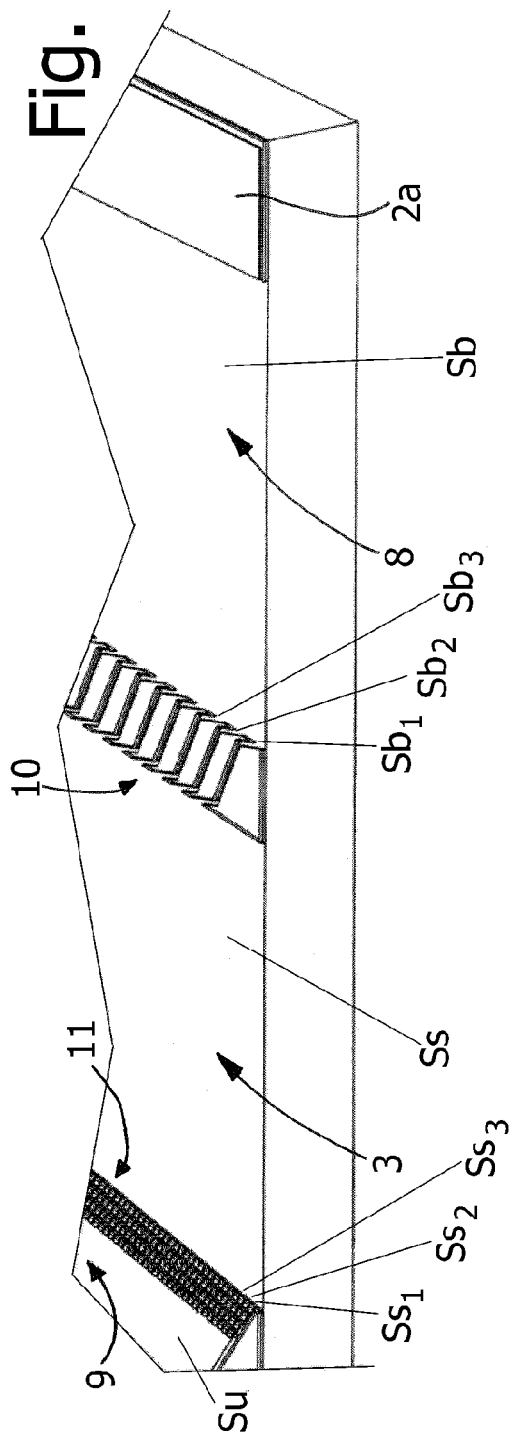
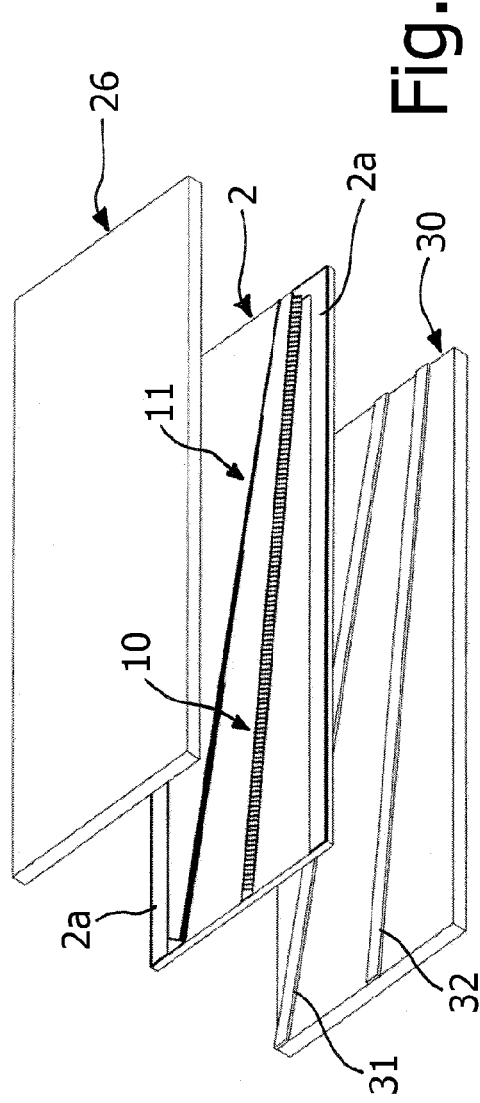

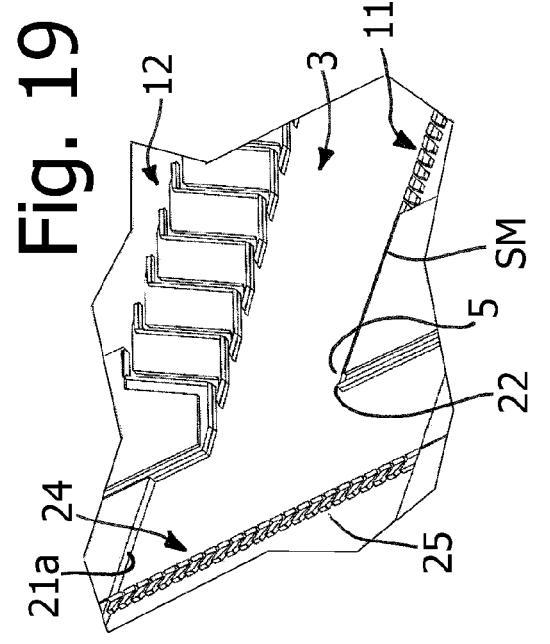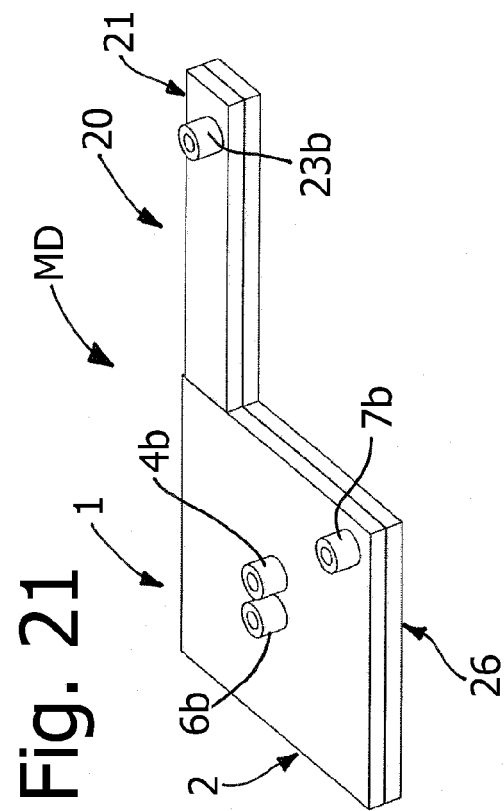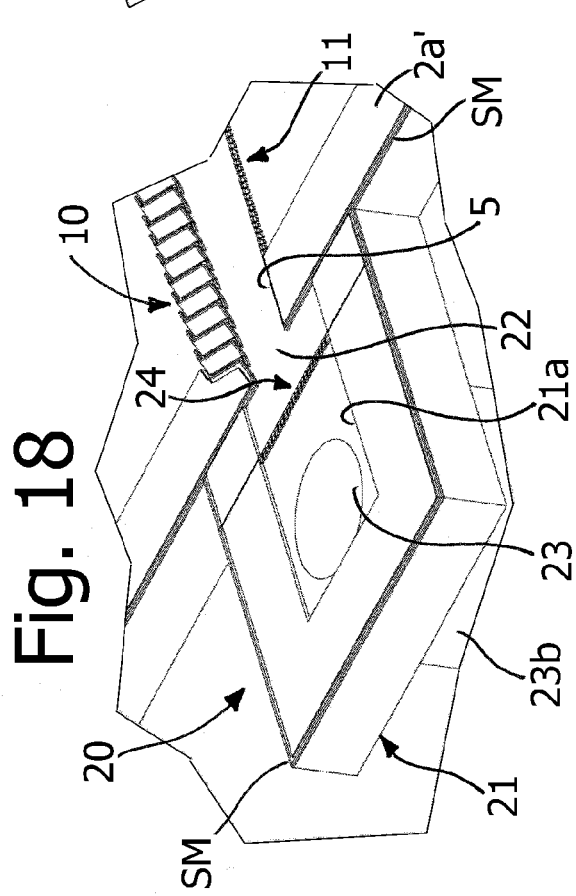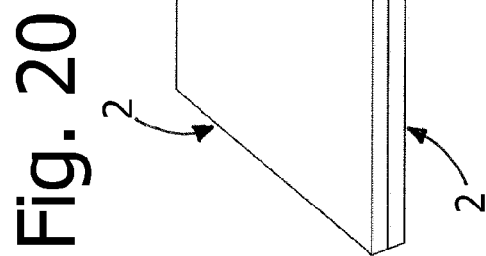

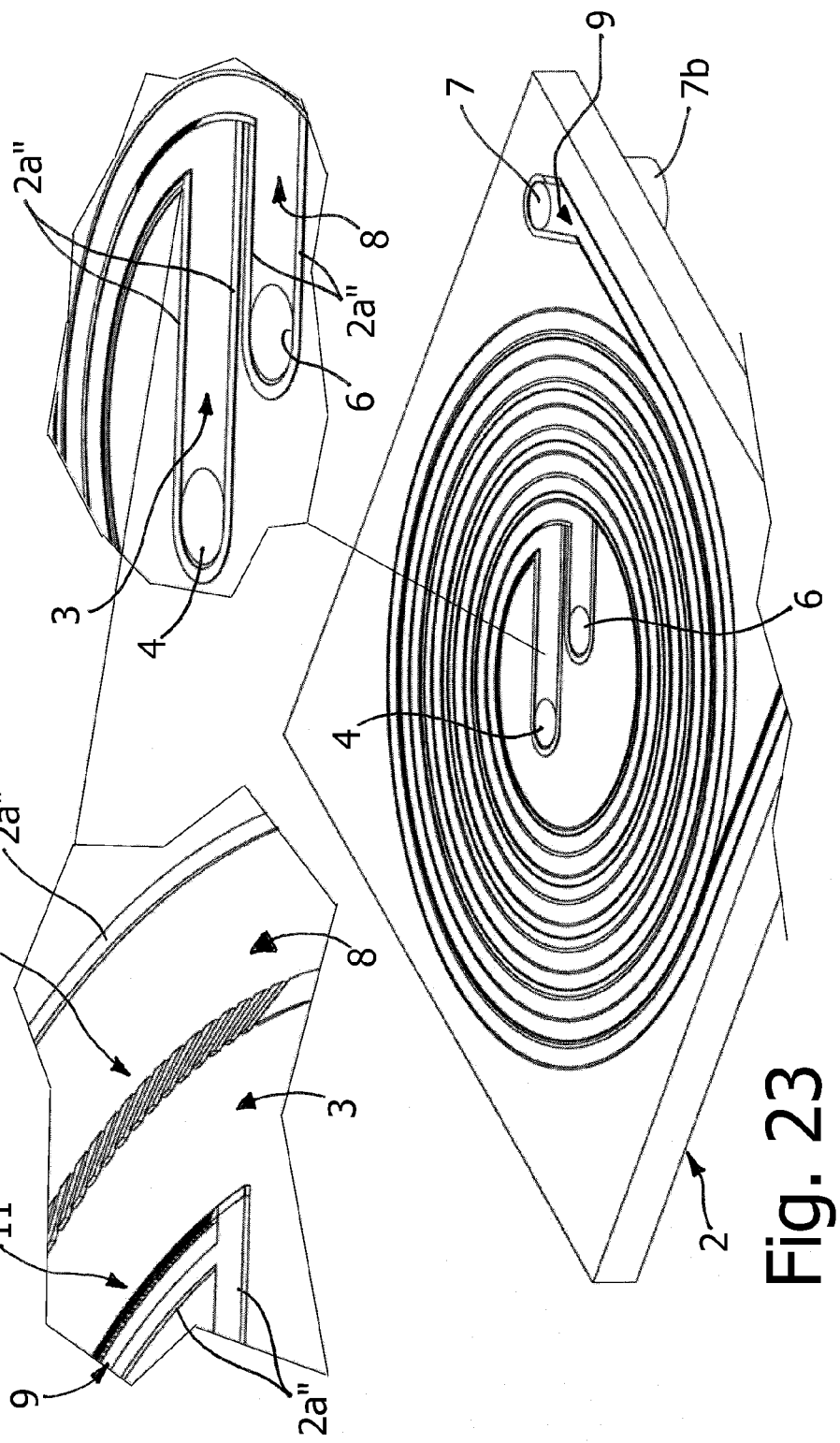
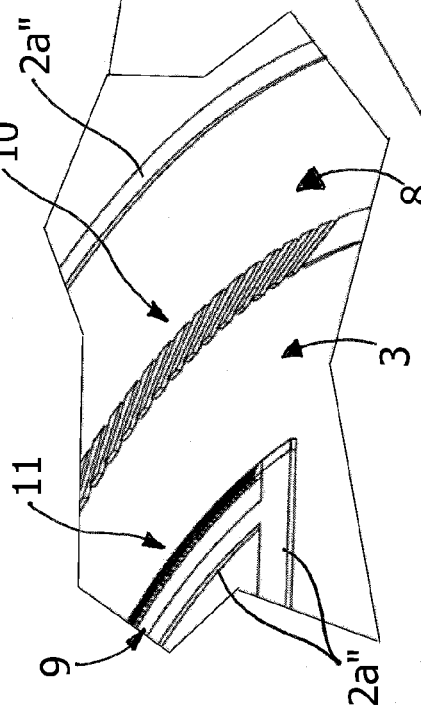

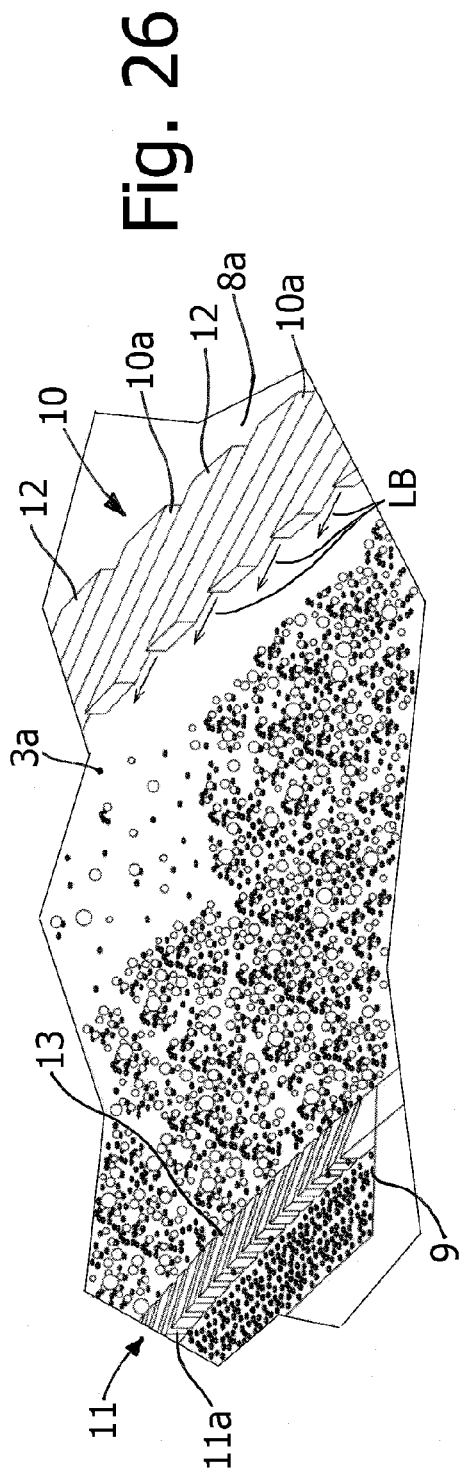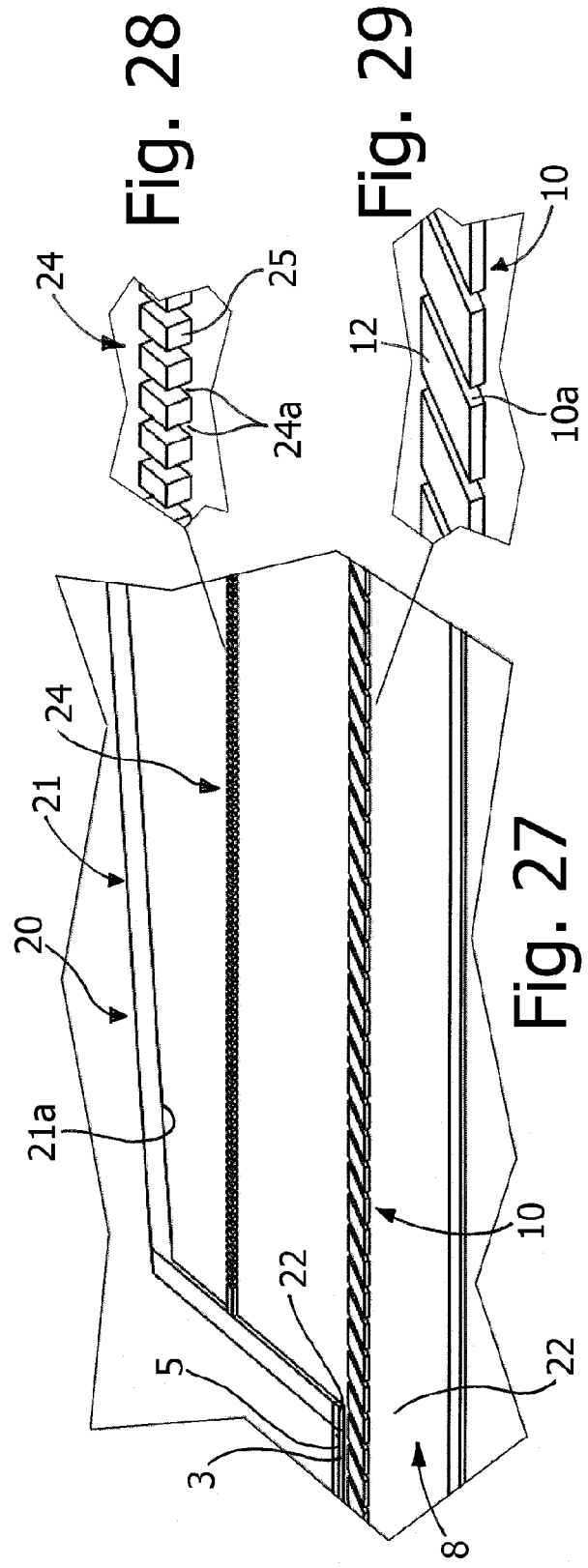

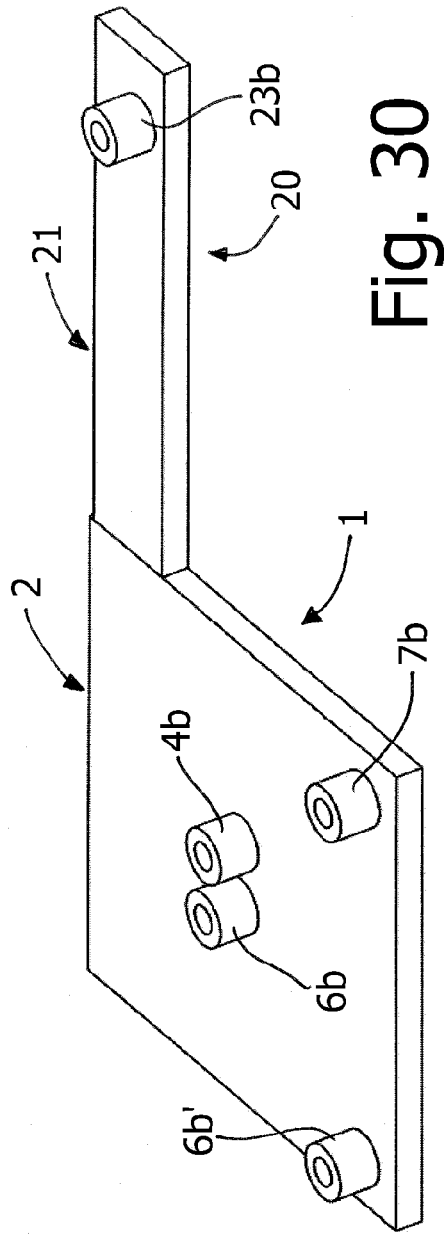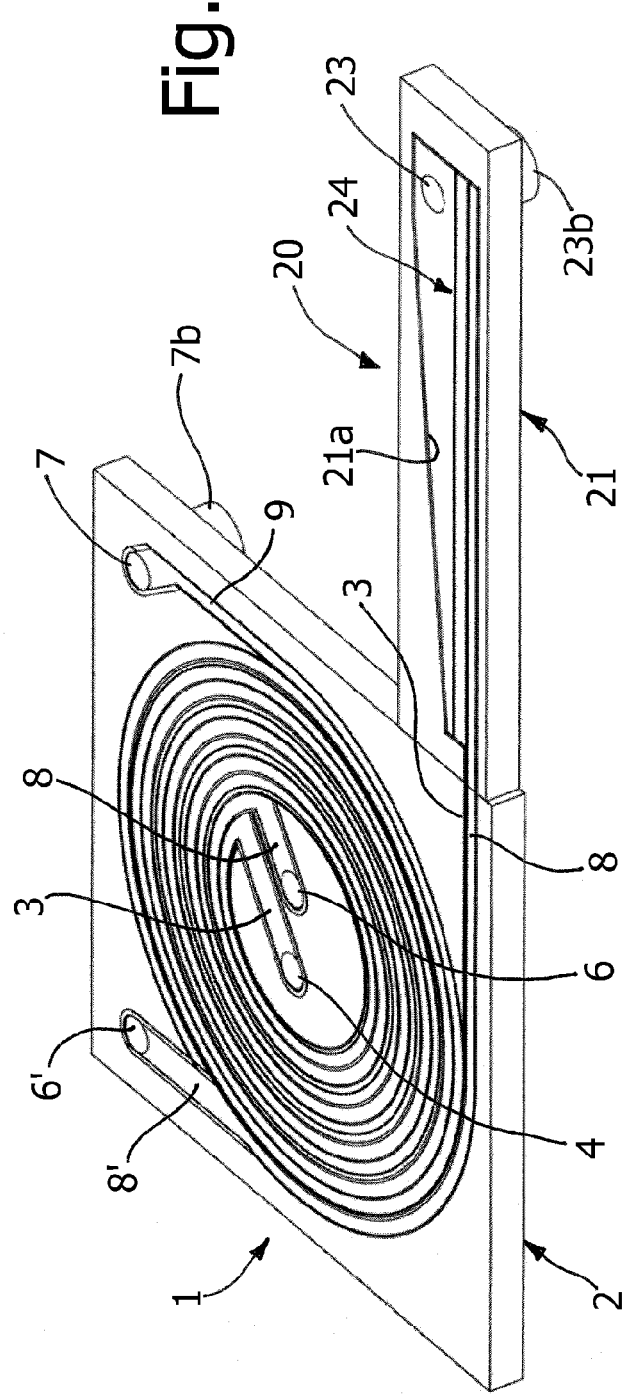

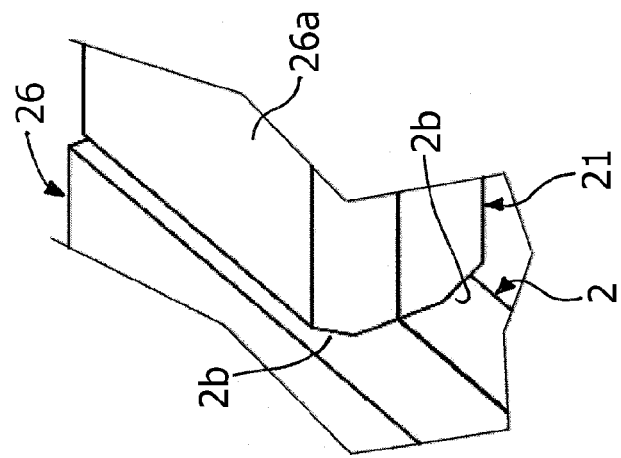
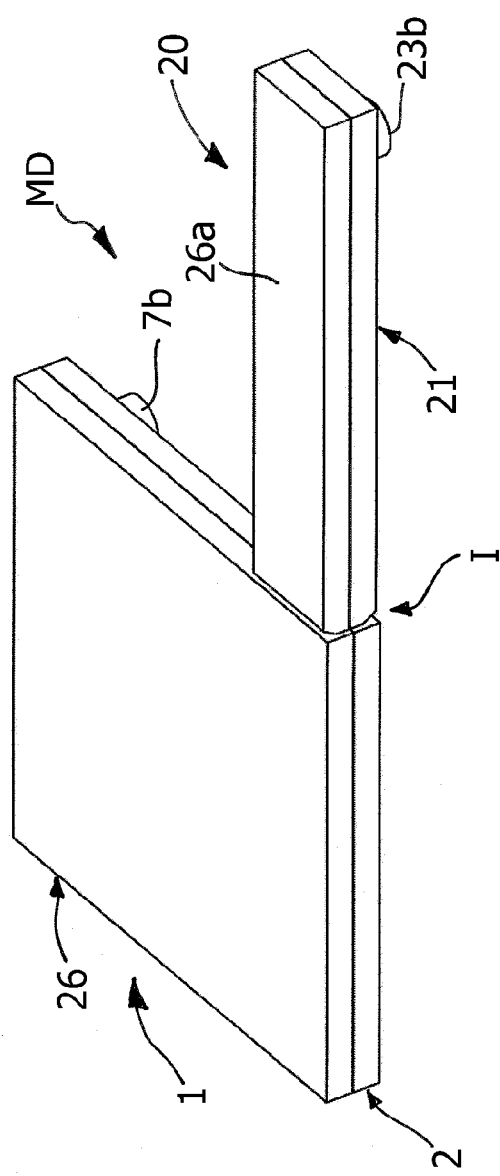
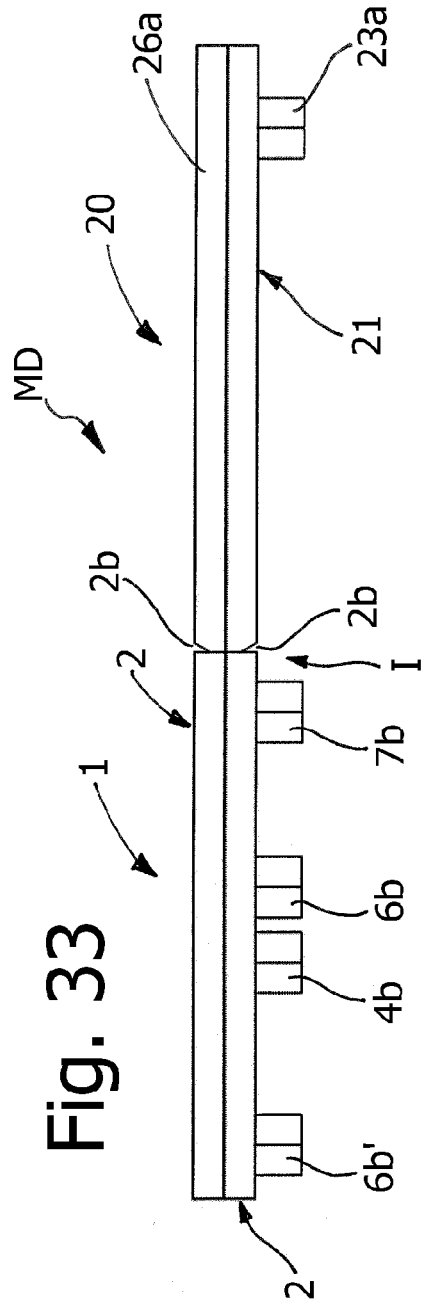

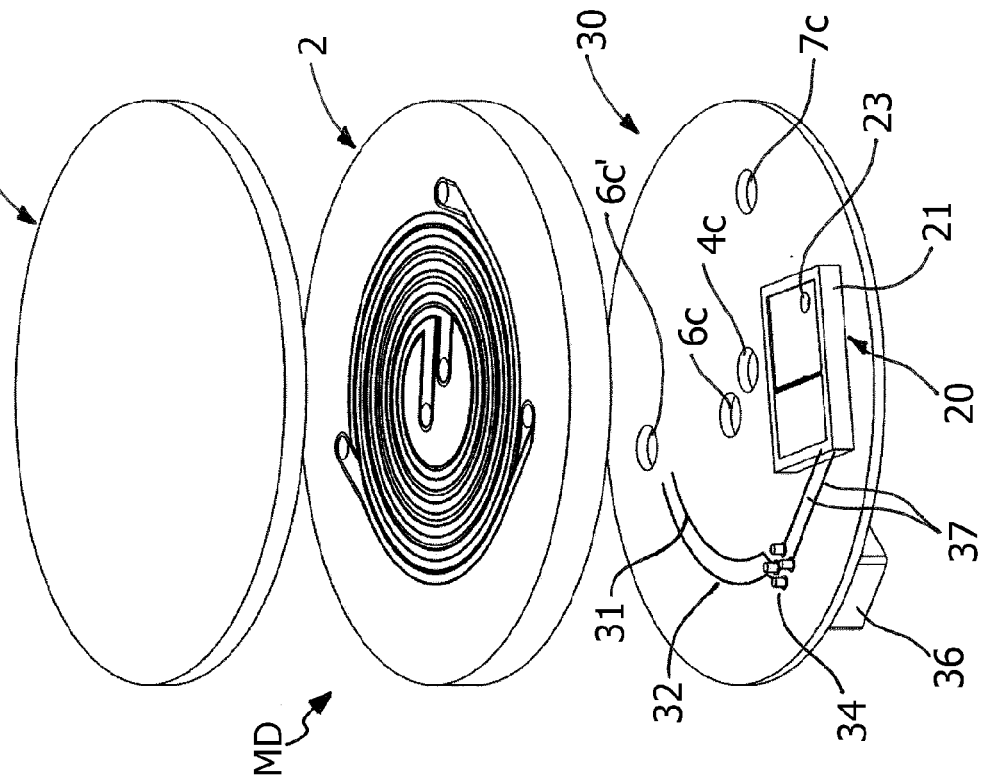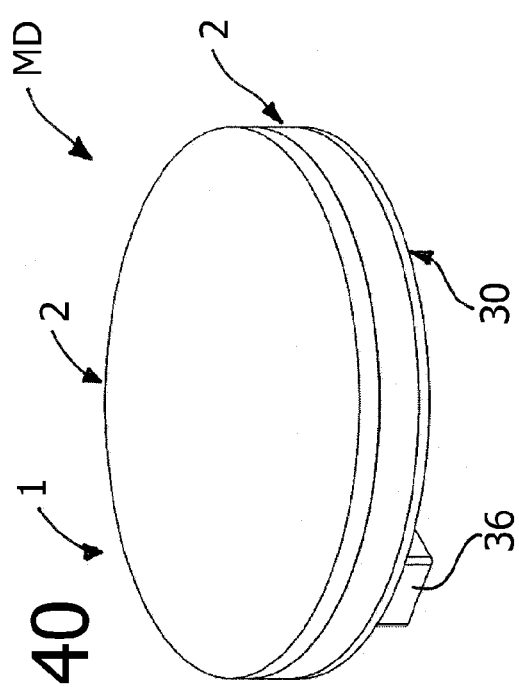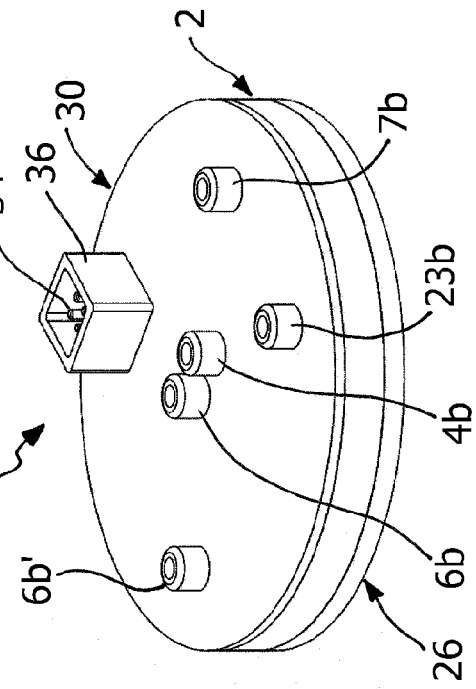

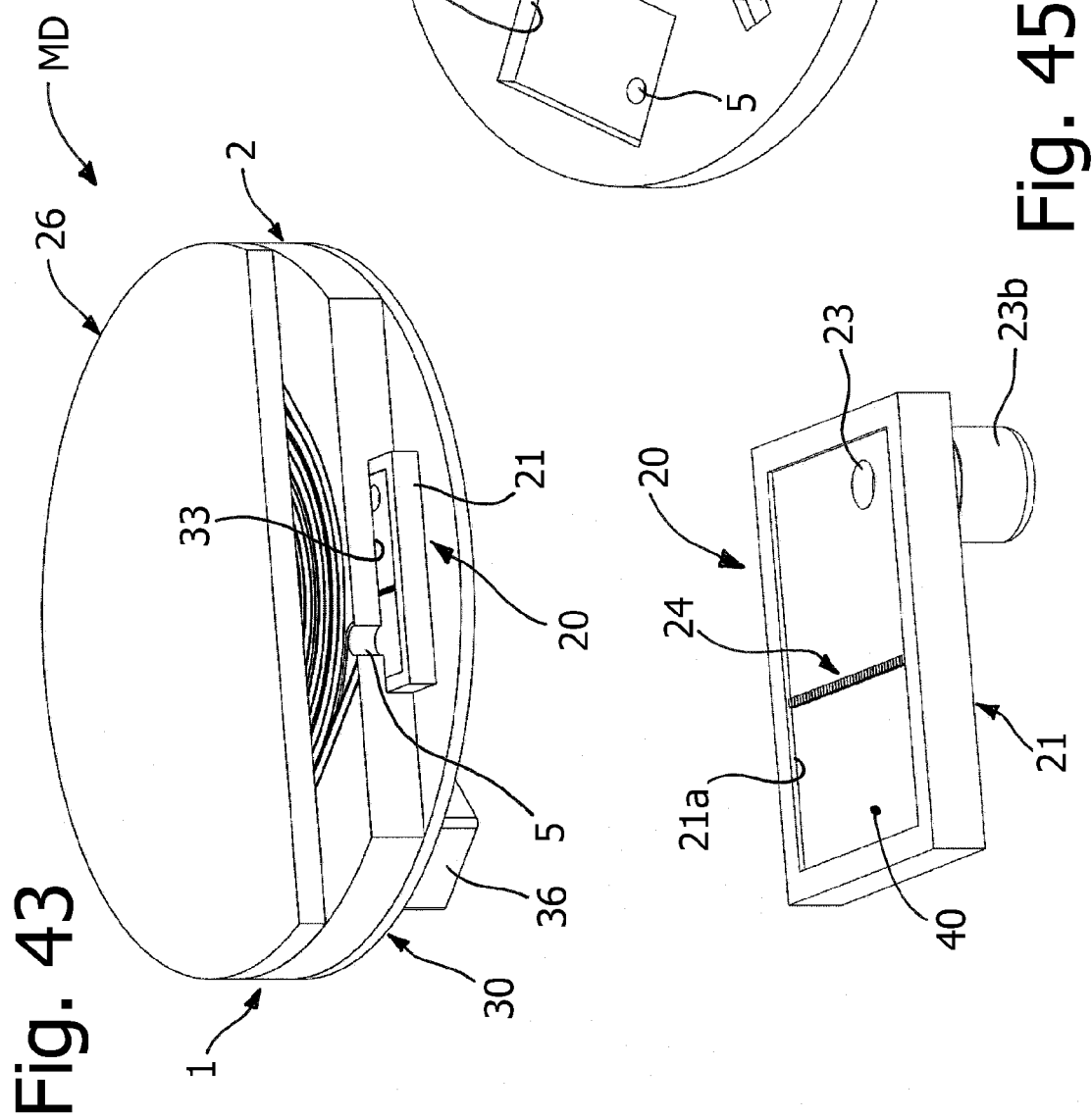

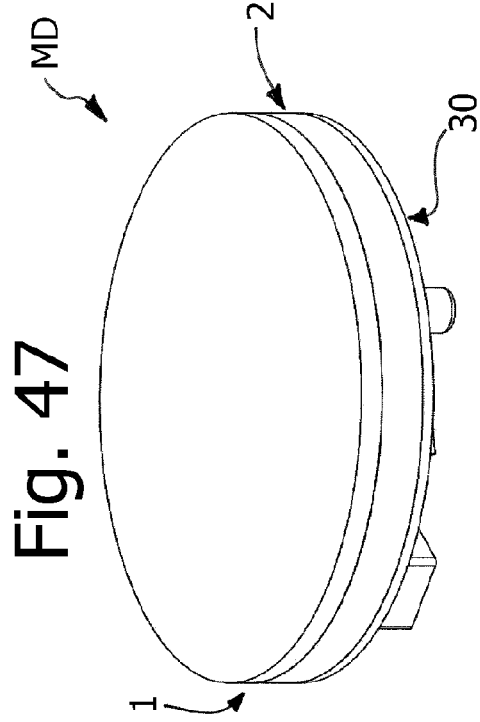
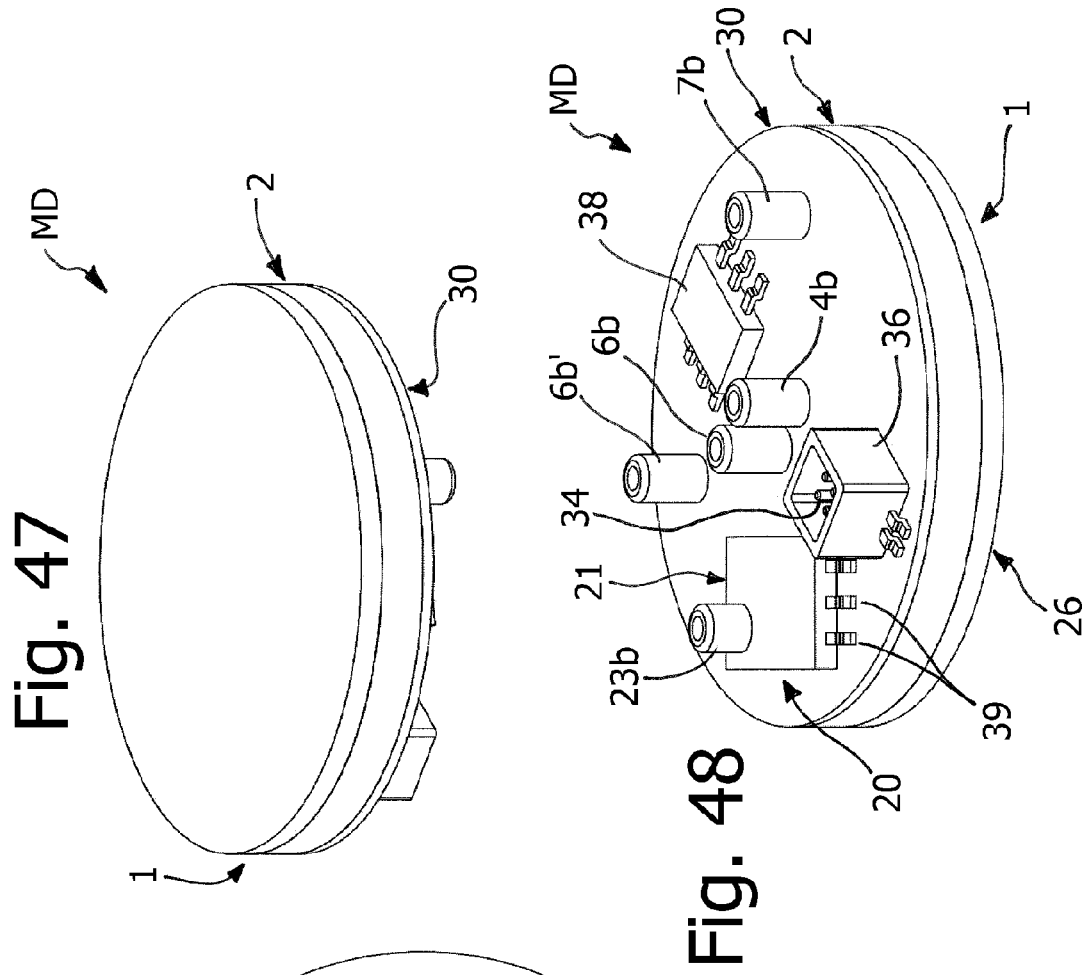
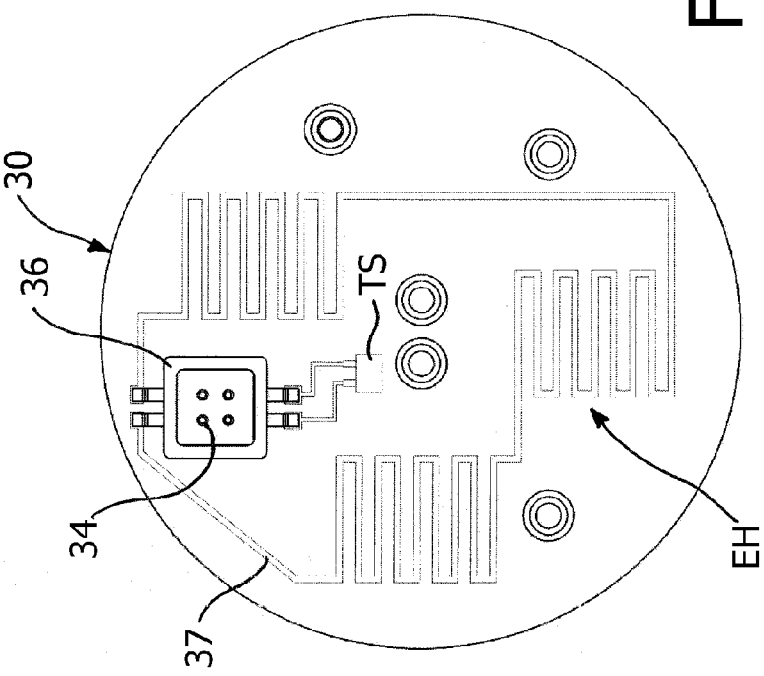

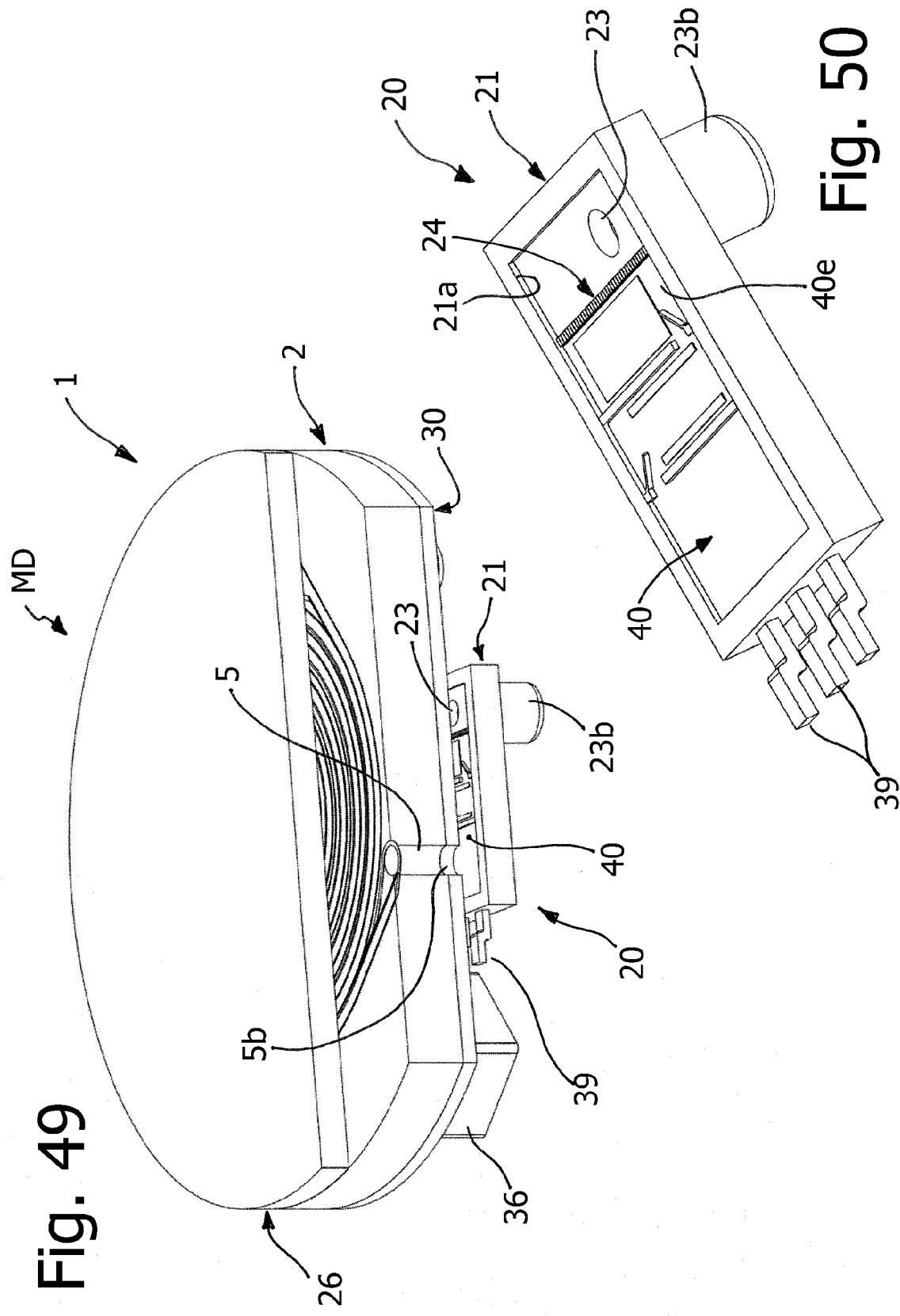

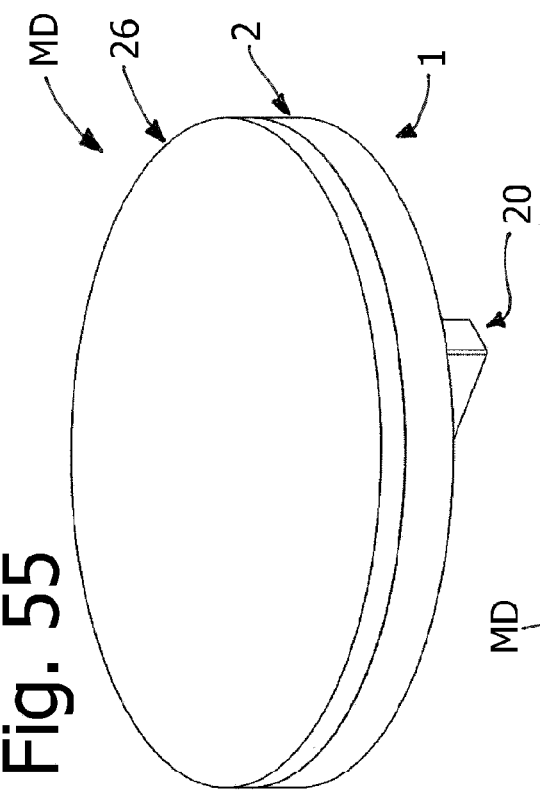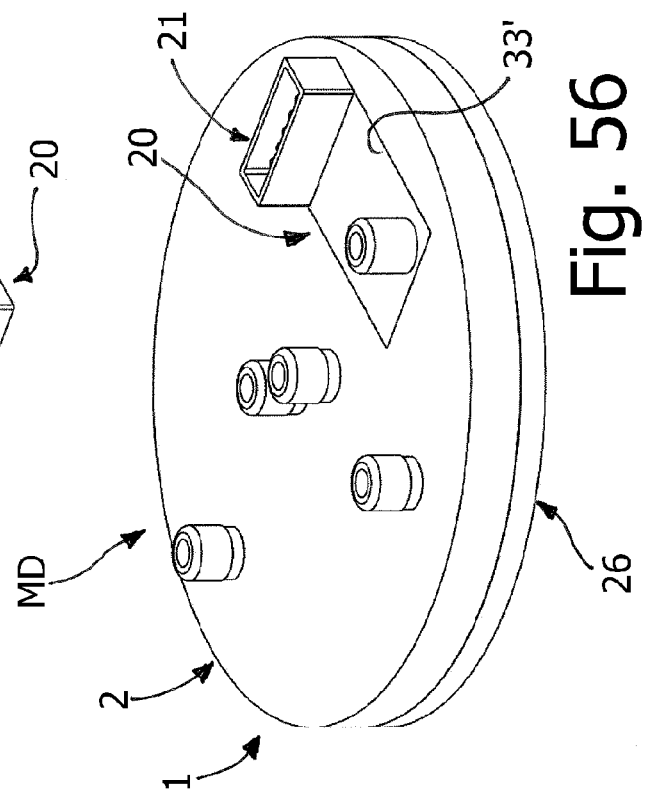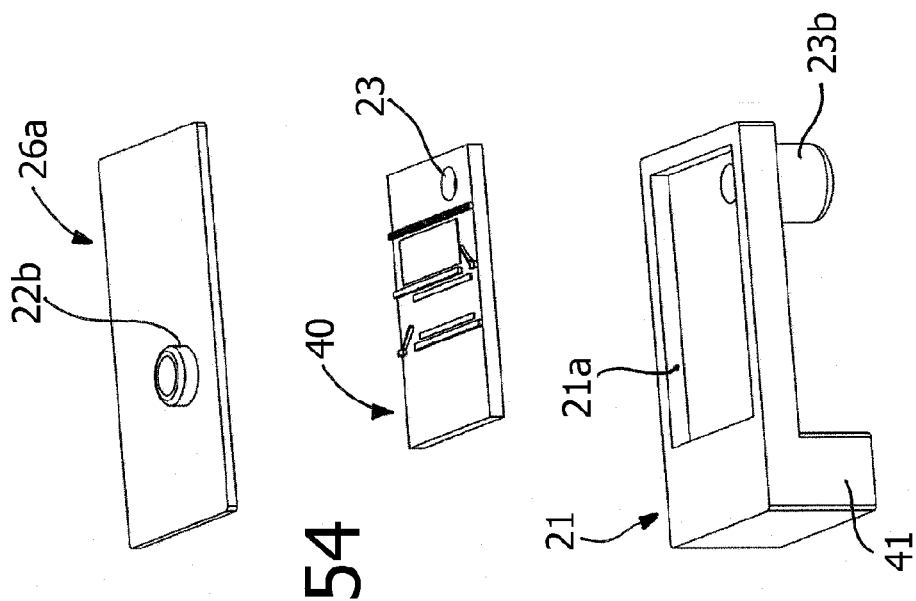

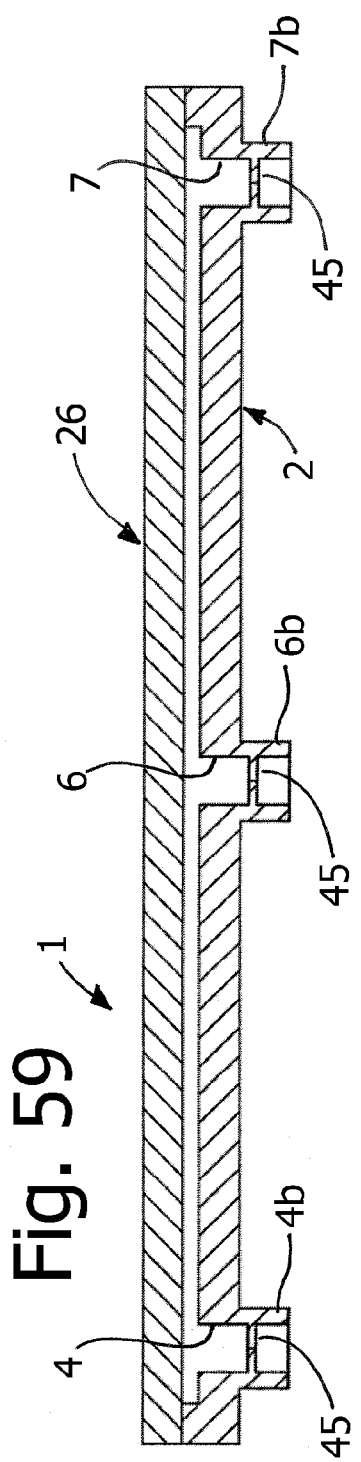
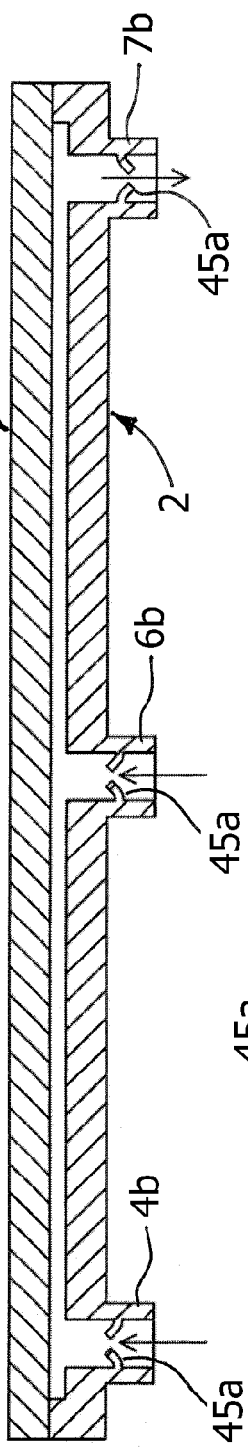
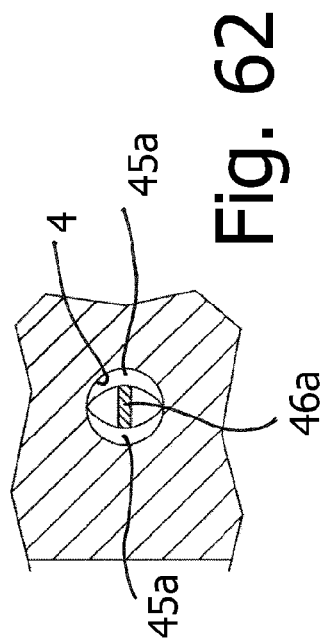
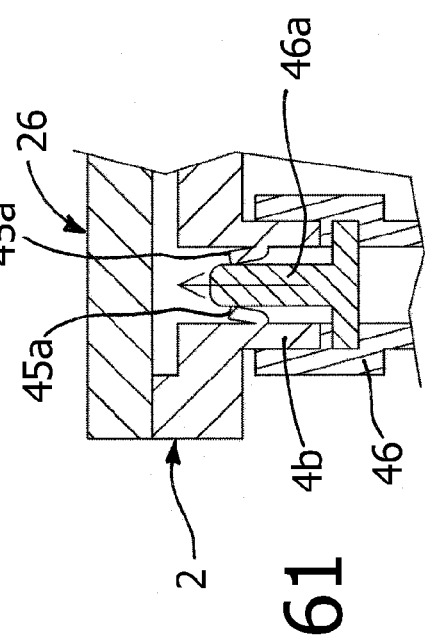

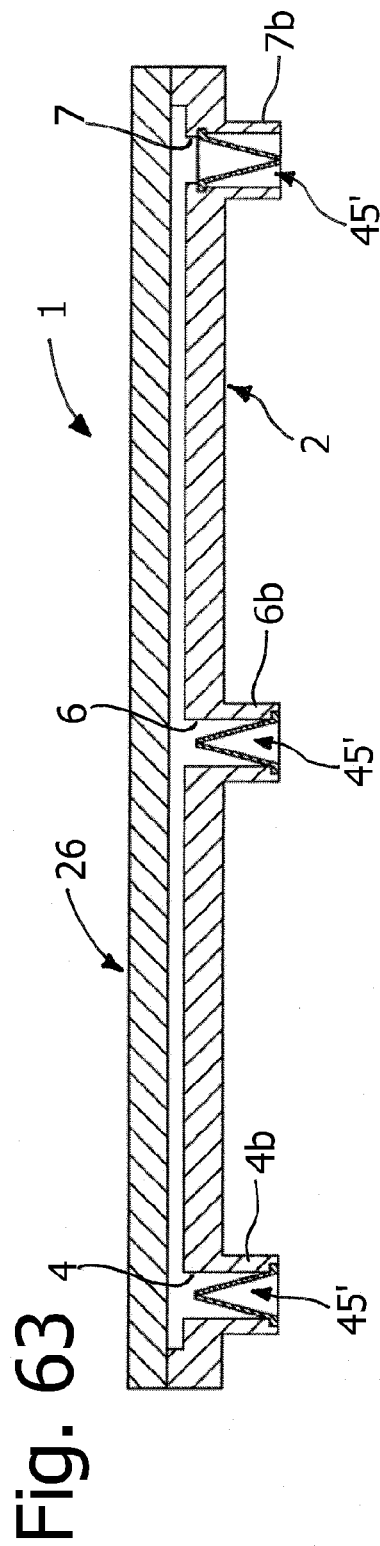
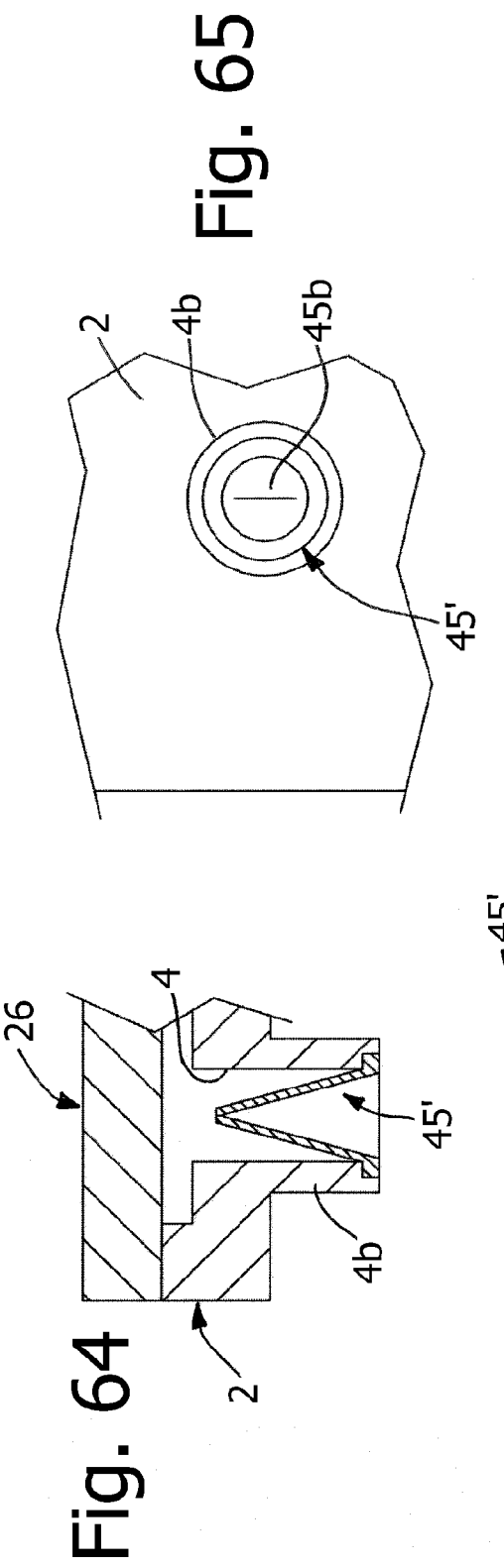
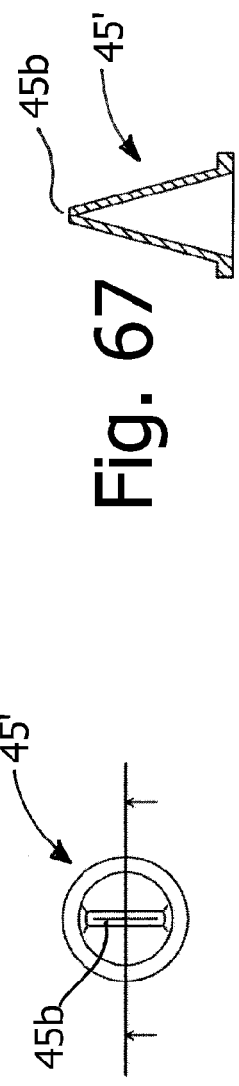
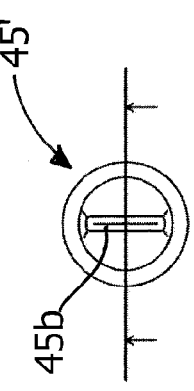

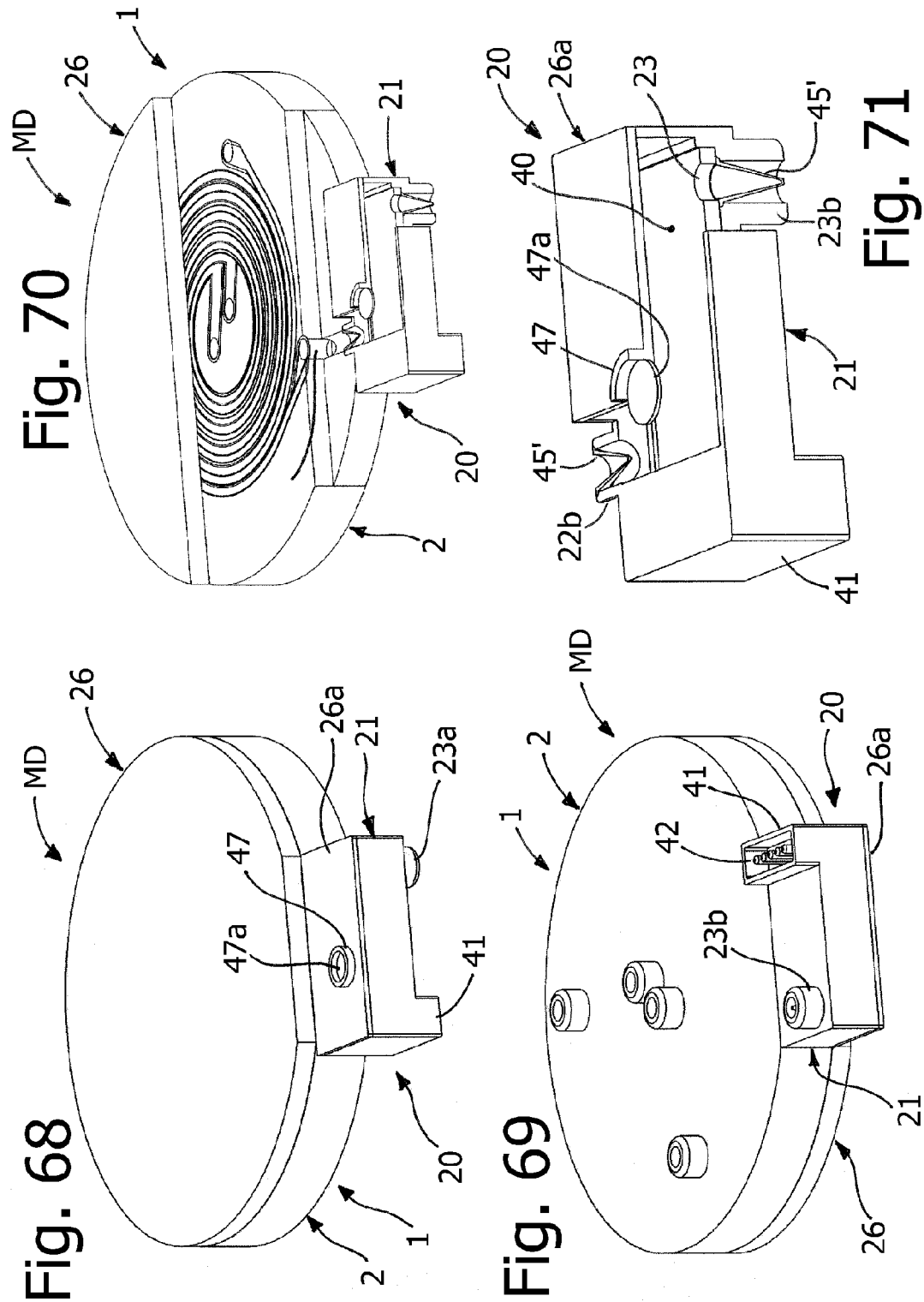

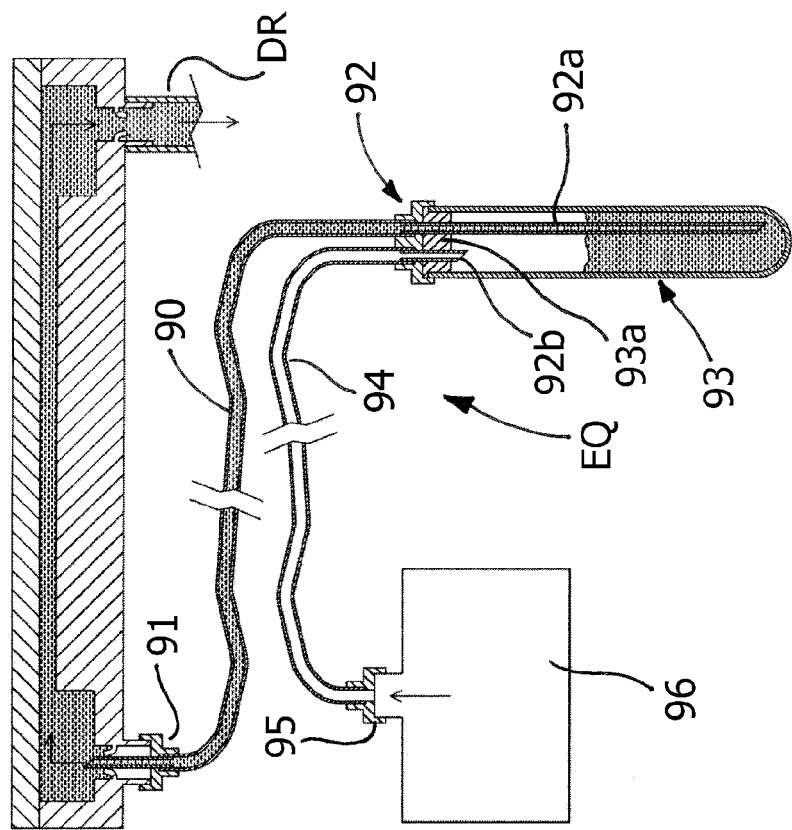
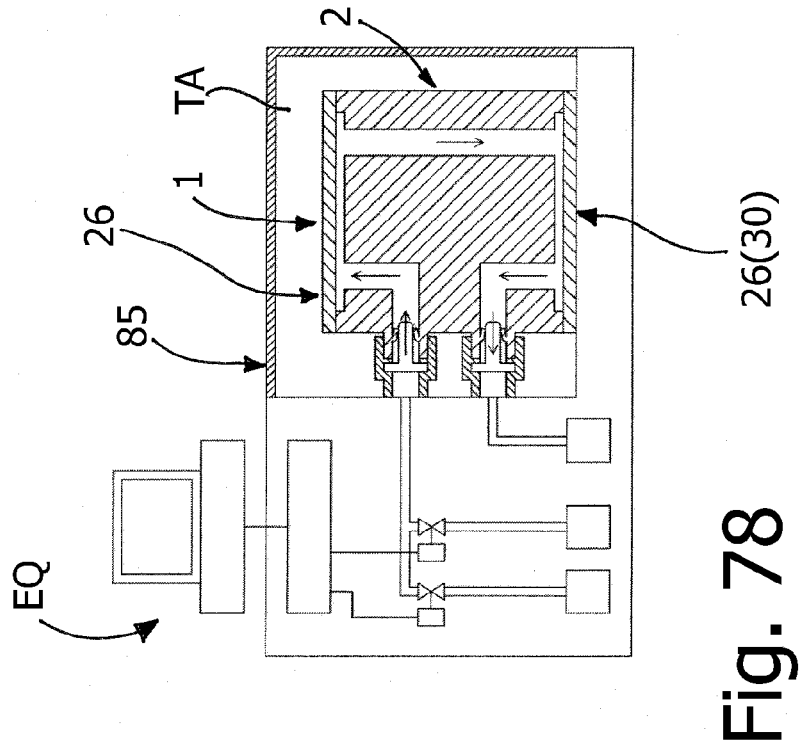

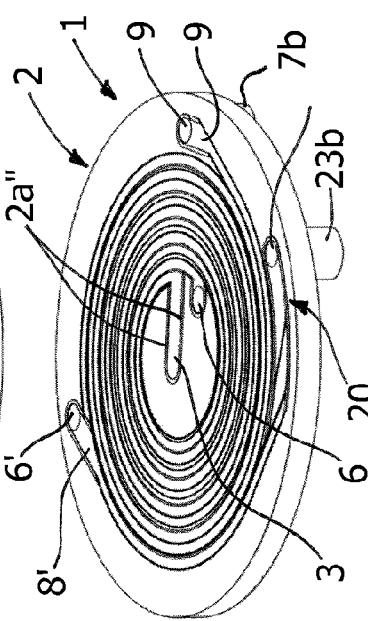
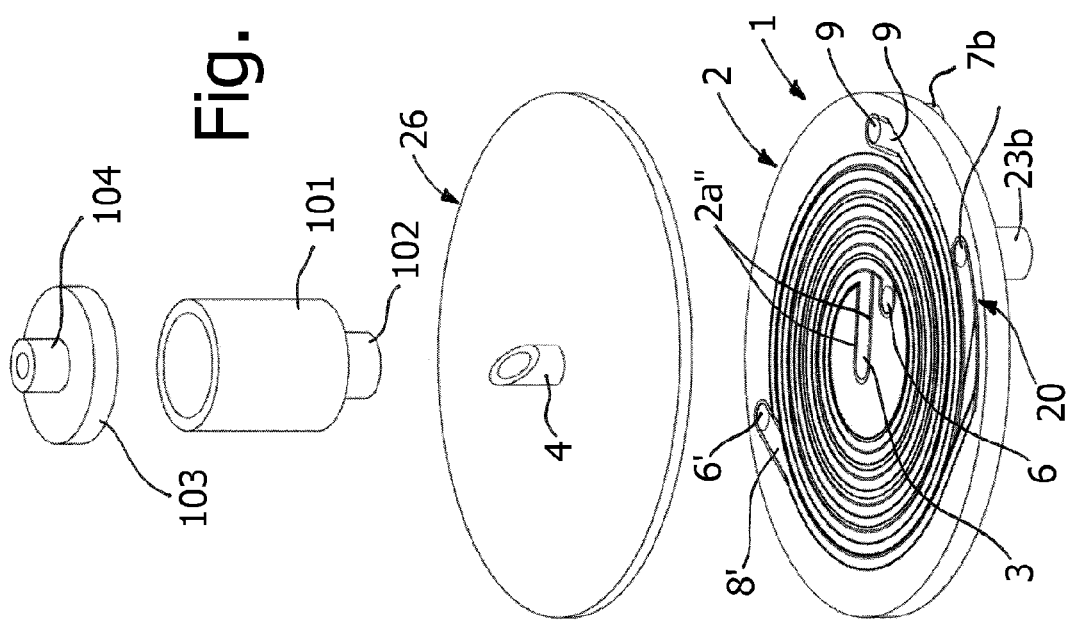
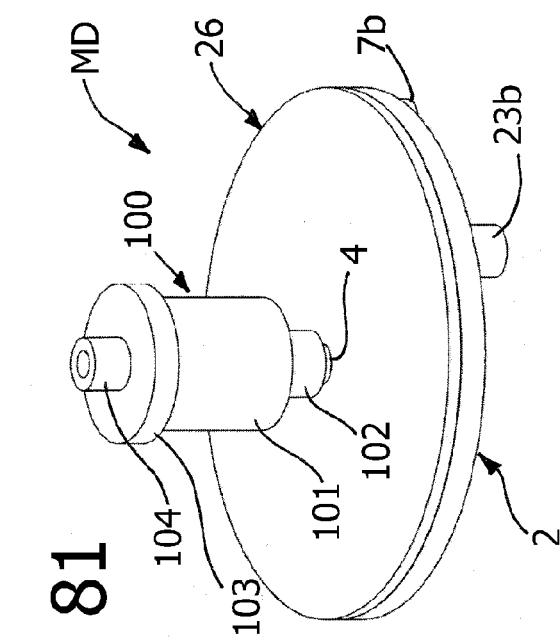
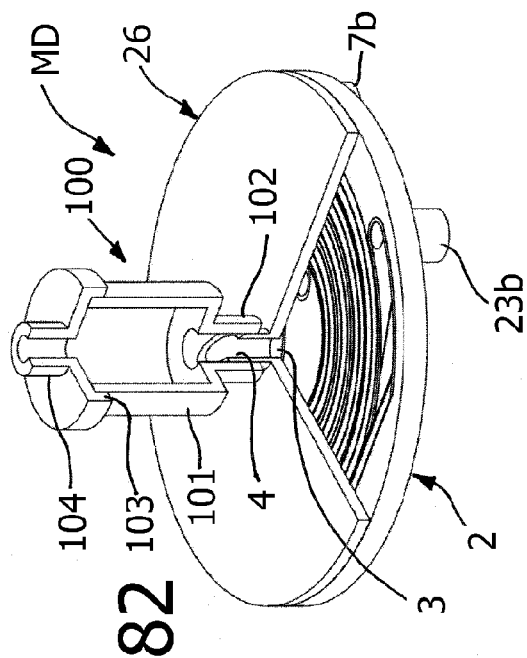

MICROFLUIDIC DEVICES AND/OR EQUIPMENT FOR MICROFLUIDIC DEVICES

CROSS-REFERENCE TO RELATED APPLICATIONS

This application is a 371 National Phase of PCT International Application No. PCT/IB2011/051733 filed on Apr. 20, 2011, and published in English as WO 2011/132164 A1 on Oct. 27, 2011, which claims priority to Italian Utility Model Application No. TO2010U000068 filed on Apr. 20, 2010, the entire disclosures of which are incorporated herein by reference.

FIELD OF THE INVENTION

The present invention relates in general to microfluidic devices, preferably of the type generally identified by terms such as "Lab-On-Chip" or "Lab-On-a-Chip" (LOC) or "Micro Total Analysis Systems" (μTAS), particularly for medical and/or biological (referred to hereinafter for simplicity as "biomedical") applications and/or for diagnostic applications, as well as to equipment that can be used in combination with microfluidic devices.

More in particular, the invention regards a microfluidic device for separating and/or concentrating a sub-population of particles from a biological fluid, the device comprising at least one first microfluidic path having an inlet, for introduction of the biological fluid into the first path, and an outlet, for release from the first path of a sample of fluid enriched in the aforesaid sub-population of particles.

PRIOR ART

For the purposes of diagnosis and study of certain diseases, for example of the blood, of the bone marrow, and of the corresponding tissues and organs, it proves useful to identify and analyse specific cells or particles present in a biological fluid.

Blood is a biological fluid basically made up of a corpuscular part and a fluid part. The corpusculate part typically comprises erythrocytes, leukocytes, and platelets, whereas the fluid part is constituted by plasma. Erythrocytes and leukocytes are cells, whereas the platelets are cellular fragments. The most numerous cells are the erythrocytes, or red blood cells, which basically perform the exchange of oxygen and carbon dioxide between the lungs and the body tissues. Leukocytes, or white blood cells, represent the smaller population of blood cells, and basically have the function of controlling the response of the immune system of the body and defending it from infectious organisms and foreign agents, both in the tissues and in the blood stream. The platelets basically have the function of bringing about coagulation of the blood.

The leukocytes population comprises cells of various types, which play distinct roles in immune response. The leukocytes can be divided into granulocytes and lymphoid cells. The granulocytes are in turn distinguished into neutrophils, eosinophils, and basophils. The lymphoid cells are, instead, distinguished into lymphocytes and monocytes. In general, erythrocytes and platelets are the particles of the blood of smallest dimensions. Indicatively, erythrocytes have a discoidal shape, with a diameter of approximately 6-8 μm and a thickness of approximately 2 μm, whilst the platelets have a diameter of approximately 2-4 μm. The cells that constitute the leukocytes have on average larger dimensions, ranging from 7 to 20 μm. Purely by way of indication, neutrophils have a diameter of approximately 12-14 μm, eosinophils a diameter of approximately 10-15 μm, basophils a diameter of approximately 14-16 μm, lymphocytes a diameter of approximately 7-15 μm, and monocytes a diameter of approximately 16-20 μm. These dimensions are purely indicative, given that, by way of example, erythrocytes have been observed with a diameter of more than 9 μm (macrocytes) or less than 6 μm (microcytes). In the same way, given that blood cells are subject to a certain degree of deformability, their dimensions may be smaller than the ones indicated above, on account of their dynamic behaviour in a flow of liquid. Moreover, cells affected by disease (for example, tumoural epithelial cells) may on average have dimensions that differ from those of healthy cells and/or have dimensions larger than 15 μm.

Leukocytes, as other particles present in the blood, can furnish important information on various illnesses. The identification of these illnesses hence involves the identification and isolation of certain cells or particles in a blood sample. Isolation may be conducted using non-invasive techniques, employing separation devices, which isolate the particles of interest on the basis of their biophysical characteristics, for example, their dimensions.

For this purpose, there is known the use of miniaturized devices, obtained with micromachining techniques, into which a blood sample is introduced. Certain of these microfluidic devices, generically known as "Lab-On-Chip" or "Lab-On-a-chip" (LOC) or "Micro Total Analysis Systems" (μTAS), also have functions of analysis on the separate particles. These devices are defined as "microfluidic devices" since they integrate one or more miniaturized hydraulic components, such as paths, passages, valves, filters, and obstacles for particles, which have at least one characteristic dimension (length, width, height, thickness, section of passage, etc.) of less than 1 mm.

In combination with the above devices it is known to use functionalized particles, prearranged for interacting with target cells or substances. These particles, also known as beads, have in general an approximately spherical shape and nanometric or micrometric dimensions, and have a nucleus sensitive to applied magnetic fields. Typically, these beads bind to a target cell, giving rise to an aggregate of particles, which, by means of a magnetic field, can be separated from the rest of the solution analysed.

SUMMARY OF THE INVENTION

Miniaturization techniques enable microfluidic devices for separating cells to be obtained that are on average efficient and presuppose the use of modest amounts of blood. Known microfluidic devices, however, are frequently relatively complicated to produce or far from practical to use, or present low reliability.

The object of the present invention is in general to provide microfluidic devices that are simple to produce and/or practical to use.

Another object of the present invention is to provide microfluidic devices and/or corresponding equipment suitable for improving and/or facilitating the separation and/or enrichment and/or identification and/or transformation and/or analysis of particles, where:

"identification of particles" refers both to the case of a marking of individual target cells or particles, for example with fluorescent beads, and to the case of a more generic identification and/or analysis, via suitable means, of a microfluidic device or a part thereof containing target particles;

by "transformation of particles" is meant at least the possible cultivation of cells and/or an extraction of parts of cell, effected directly in at least one part of the microfluidic device itself that has previously carried out a separation.

Another general object of the invention is to provide equipment that can be used advantageously in combination with microfluidic devices.

The above and further objects that will emerge more clearly hereinafter are achieved according to the invention by devices having the characteristics indicated in the attached claims. The claims form an integral part of the technical teaching provided herein in relation to the invention.

BRIEF DESCRIPTION OF THE DRAWINGS

Further purposes, characteristics and advantages of the present invention will emerge clearly from the ensuing detailed description and from the annexed drawings, which are provided purely by way of explanatory and non-limiting example, and in which:

FIGS. 3A, 3B and 3C are, respectively, a first detail and a second detail, at an enlarged scale, of the device of FIG. 3, and a partial perspective view of a variant of the device of FIG. 3;

FIGS. 4A and 4B are schematic illustrations of examples of aggregates of particles that can be separated by means of a device according to the invention;

FIG. 6 is a view similar to that of FIG. 5, with the addition of a body for closing the device;

FIGS. 7-11 are perspective views, at an enlarged scale, of some details of the device of FIGS. 5 and 6;

FIGS. 12-14 are perspective views, at an enlarged scale, of further details of the device of FIGS. 5 and 6;

FIG. 15 is a perspective and schematic view of a further microfluidic device according to the invention;

FIGS. 18 and 19 are perspective views, at an enlarged scale, of respective details of the device of FIG. 19;

FIGS. 20 and 21 are perspective views from different angles of another microfluidic device according to the invention;

FIG. 23 is an enlarged perspective view of a portion of the device of FIG. 22;

FIGS. 24 and 25 are details at an enlarged scale of FIG. 23;

FIG. 26 is a perspective view at an enlarged scale of a portion of the device of FIGS. 20-26;

FIG. 27 is an enlarged perspective view of a portion of the device of FIG. 22;

FIGS. 28 and 29 are details at an enlarged scale of FIG. 27;

FIGS. 30 and 31 are perspective views from different angles of a main body according to a variant of the device of FIGS. 20-29;

FIGS. 32 and 33 are a perspective view and a side view of another microfluidic device according to the invention;

FIG. 34 is an enlarged detail of FIG. 32;

FIGS. 40 and 41 are perspective views from different angles of another microfluidic device according to the invention;

FIGS. 42 and 43 are an exploded view and a partially sectioned perspective view, respectively, of the device of FIGS. 40 and 41;

FIG. 44 is a perspective view similar to that of FIG. 41, with a part of the device removed;

FIG. 45 is a perspective view of a part of the device of FIGS. 40-44;

FIG. 46 is a plan view from beneath of another fluidic device according to the invention;

FIGS. 47 and 48 are perspective views from different angles of another microfluidic device according to the invention;

FIG. 49 is a partially sectioned perspective view of the device of FIGS. 47-48;

FIG. 50 is a perspective view of a part of a microfluidic device according to the invention, such as the device of FIGS. 47-49;

FIG. 54 is an exploded view of the part of microfluidic device according to FIGS. 52 and 53;

FIGS. 55 and 56 are perspective views from different angles of another microfluidic device according to the invention;

FIGS. 59 and 60 are two schematic sections of another device according to the invention, in two different operating conditions;

FIG. 61 is a cross section, at an enlarged scale, of a variant of the device of FIGS. 59-60;

FIG. 62 is a cross section of FIG. 61;

FIGS. 63 and 64 are a schematic section and a corresponding enlarged detail, respectively, of another device according to the invention;

FIG. 65 is a plan view of the detail of FIG. 64;

FIGS. 66 and 67 are a plan view and a view in cross section of a valve means of the device of FIGS. 63-64;

FIGS. 68 and 69 are perspective views, respectively from above and from beneath, of a part of a microfluidic device according to the invention;

FIG. 70 is a partially sectioned perspective view of the device of FIG. 68;

FIG. 71 is a partially sectioned perspective view, at an enlarged scale, of a part of the device of FIG. 70;

FIGS. 77 and 78 are simplified representations of further apparatuses of the same type as that of FIG. 76;

FIG. 79 is a schematic representation of equipment according to the invention, of a disposable type that can be used in combination with a microfluidic device;

FIG. 81 is a perspective view of another microfluidic device according to the invention;

FIGS. 82 and 83 are a perspective view in partial cross section and an exploded view, respectively, of the device of FIG. 81;

DETAILED DESCRIPTION OF PREFERRED EMBODIMENTS OF THE INVENTION

Figure 1:
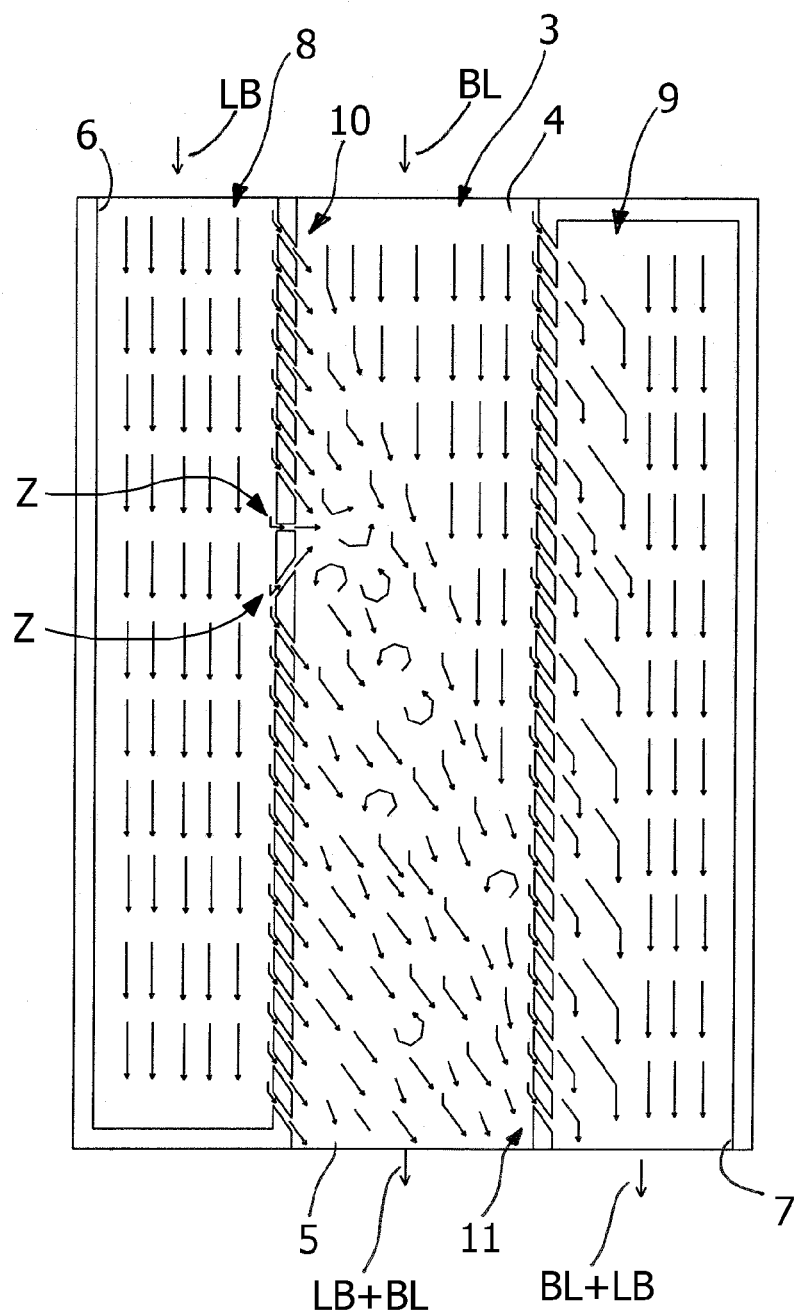
FIG. 1 is a schematic representation in plan view of a microfluidic arrangement, aimed at illustrating the general working principle of a methodology of micro-filtering or micro-separation envisaged in a preferential embodiment of the invention.

Reference to "an embodiment" or "one embodiment" in the framework of the present description is meant to indicate that a particular configuration, structure, or characteristic described in relation to the embodiment is comprised in at least one embodiment. Hence, the phrases such as "in an embodiment" or "in one embodiment" and the like that may be present in different points of the present description do not necessarily all refer to one and the same embodiment. In addition, the particular configurations, structures, or characteristics may be combined in any adequate way in one or more embodiments. The references used herein are provided merely for convenience and do not define the sphere of protection or the scope of the embodiments.

Where not otherwise indicated, in the present description and in the attached claims:

by "bead" is meant functionalized particles or microparticles and/or generic vectors of ligands, such as antibodies, in particular prearranged for interacting with target cells, substances, or particles, said beads preferably having an approximately spherical shape and/or nanometric or micrometric dimensions;

by "particle" and derivatives is meant any solid object not dissolved in a biological fluid, such as cells, aggregates of cells, beads, aggregates of cells and beads, etc.;

by "buffer" and the like is meant a liquid substance designed to dilute the biological fluid or blood and/or facilitate and/or modify the flow of the biological fluid or blood within a microfluidic device, or more in general a liquid designed to interact with the biological fluid for the purposes of the invention; the buffer may, for example, be distilled water or a physiological or saline solution, possibly containing an anticoagulant and/or bead.

The microfluidic devices described hereinafter are preferably of the type envisaged at least for concentrating target particles in an organic fluid, or else to obtain, from an organic fluid at inlet containing a population of particles, a sample enriched in a sub-population of target particles, or else devices designed at least to separate particles of specific interest.

Examples of target particles are leukocytes, foetal erythrocytes, carcinogenic cells, infectious organisms, as well as beads and aggregates of particles, such as for example a bead to which one or more cells are bound, or a cell to which a number of beads are bound.

Preferably, the devices described in what follows include separation or filtering means, such as means of a substantially mechanical type, set along a path or between an inlet and an outlet of a path for the fluid containing the population of particles. In particular, the separation means are configured so as to withhold or separate at least the target particles, for example ones having a certain shape, size or deformability, or given physical characteristics, whereas other particles are evacuated from the device. These separation or filtering means are preferably defined directly in the body of the device, via micromachining and/or microdeposition techniques, and hence without having to mount or fix components for said purpose, such as membranes or sieves configured as additional parts.

The devices described in what follows may moreover be used for removing excess fluid from a sample of particles, without this entailing a substantial loss of target particles in the fluid removed.

The invention will be described in what follows with reference to enrichment of target particles or elements contained or dispersed in a biological fluid, in particular to enrichment of tumour cells and/or leukocytes and/or other target cells in a blood sample. Consider, however, that the invention is in general applicable also to particles of a different type and nature, present also in fluids different from biological fluids; consequently, in the ensuing description, the term "blood" may be considered, if necessary, as indicating also a generic fluid.

There follows a description of inventive embodiments of microfluidic devices and inventive embodiments of equipment that can be used in combination with microfluidic devices. The microfluidic devices described are of particularly advantageous use in combination with the equipment described, but this does not exclude either use of the aforesaid devices in combination with equipment different from the one described herein, or use of the aforesaid equipment in combination with microfluidic devices different from the ones described herein.

As will emerge clearly in what follows, in a preferential embodiment of the invention, the microfluidic device is conceived for carrying out a micro-filtering or micro-separation of a type here defined as "mixed flow", which will now be briefly described with reference to FIG. 1.

In general terms, in accordance with such an inventive principle, a first fluid BL, in particular a biological fluid under analysis, is made to flow in a first path or channel 3, here defined as "main path", between at least one inlet 4 and at least one outlet 5. This main path 3 extends at least in part between a first path or channel and a second path or channel, here defined as "auxiliary paths" and designated by 8 and 9, which are delimited with respect to the main path 3 by a first lateral delimitation 10 and a second lateral delimitation 10 and 11, each provided with respective passageways, where the path 8 has at least one inlet 6 and the path 9 has at least one outlet 7. Preferably, these lateral delimitations or dikes define the minor dimension of the cross section of the path 3.

Introduced through the inlet 6 into the first auxiliary path 8 is an auxiliary fluid LB, such as a liquid buffer (or else a portion of the biological fluid being analysed itself), which is to mix with the first fluid BL.

The second auxiliary path 9 basically performs functions of discharge channel for a part of the mixture BL+LB of the two fluids, that in particular contains particles different from the target particles, with the corresponding second lateral delimitation 11, provided with the corresponding passageways, that performs to functions of micro-filtering or micro-separation.

Via the passageways of the first lateral delimitation 10 the auxiliary fluid LB penetrates laterally into the main path 3, mixing with the first fluid BL.

In this way, in general, the auxiliary fluid LB imparts on the flow of the first fluid BL and/or on particles contained therein a component of thrust or movement, preferably towards the second lateral delimitation 11 and/or towards the outlet 5 of the main path 3. The particles of dimensions smaller than those of the passageways of the second lateral delimitation 11 are in this way induced to pass into the second auxiliary discharge path 9, together with a part of the mixture, designated by BL+LB, whereas the particles having dimensions larger than those of the passageways of the second lateral delimitation 11 remain in the main path 3 so as to converge towards the outlet 5 in a part of the mixture that is enriched with said target particles, designated by LB+BL.

The passageways of the auxiliary fluid LB from the path 8 to the path 3 are preferably configured, for example in terms of dimensions and/or orientation, so as to cause the auxiliary fluid to bring about an albeit minimal deviation or turbulence in the flow of the first fluid. In particular, the purpose of this is to cause the first fluid BL and/or particles contained therein to flow in the proximity of the passageways of the second lateral delimitation 11 in order to favour an optimal separation. The modes of introduction or mixing of the auxiliary fluid LB are hence preferably such as to change the direction of the threads of the first fluid BL that flows in the main path—as indicated by the small arrows within the main path 3—in order to prevent in said path 3 the flow of the first fluid from being prevalently laminar or oriented in just the direction of flow of the main path. The flows in the paths 3 and 8—and consequently in the path 9—are preferably continuous flows in order to produce continuous perturbations of the flow in the path 3; said flows could, however, be at least in part of a pulsed type.

Hence, basically, in accordance with the methodology of separation or concentration here proposed:

a) a first microfluidic channel 3, a second microfluidic channel 8, and a third microfluidic channel 9 are provided, having at least respective mutually adjacent parts, in particular adjacent in length, with a said at least one part of the first channel 3 that is delimited laterally, with respect to a corresponding said at least one part of the second channel 8 or of the third channel 9, by a first lateral delimitation 10 or a second lateral delimitation 11, respectively, said lateral delimitations having respective passageways for connecting the second channel 8 to the first channel 3 and the third channel 9 to the first channel 3, respectively; and b) introduced into the first channel 3 is a biological fluid BL and introduced into the second channel 8 is an auxiliary fluid LB, in such a way that a flow of the auxiliary fluid LB at outlet from the passageways of the first lateral delimitation 10 forms, in the first channel 3, a mixture LB+BL with the biological fluid BL, with a first fraction of this mixture LB+BL that flows in the third channel 9 through passageways provided at a filtration and/or separation part of the second lateral delimitation 11a and with a second fraction of the mixture LB+BL that remains in the first channel 3. At least part of the auxiliary fluid LB at outlet from the passageways of the first lateral delimitation 10 is in particular such as to obtain at least one of the following effects:

imparting on the flow in the first channel 3 and/or on particles contained therein at least one from among a component of thrust or movement, a transverse component, a turbulence, and an irregular motion;

forcing particles or aggregates of particles having a dimension smaller than a dimension of the passageways of the second lateral delimitation 11 to pass into the third channel 9; and forcing towards an outlet 5 of the first channel 3 particles or aggregates of particles constituting a sub-population of interest.

The modes of introduction of the fluids into the channels 3 and 8 may be different, and comprise, for example, at least one from among:

introducing in a continuous way the biological fluid and the auxiliary fluid;

introducing in a pulsed way the biological fluid and the auxiliary fluid;

introducing in an alternating way the biological fluid and the auxiliary fluid;

introducing in an alternating way the biological fluid and introducing in a continuous way the auxiliary fluid.

Figure 2:
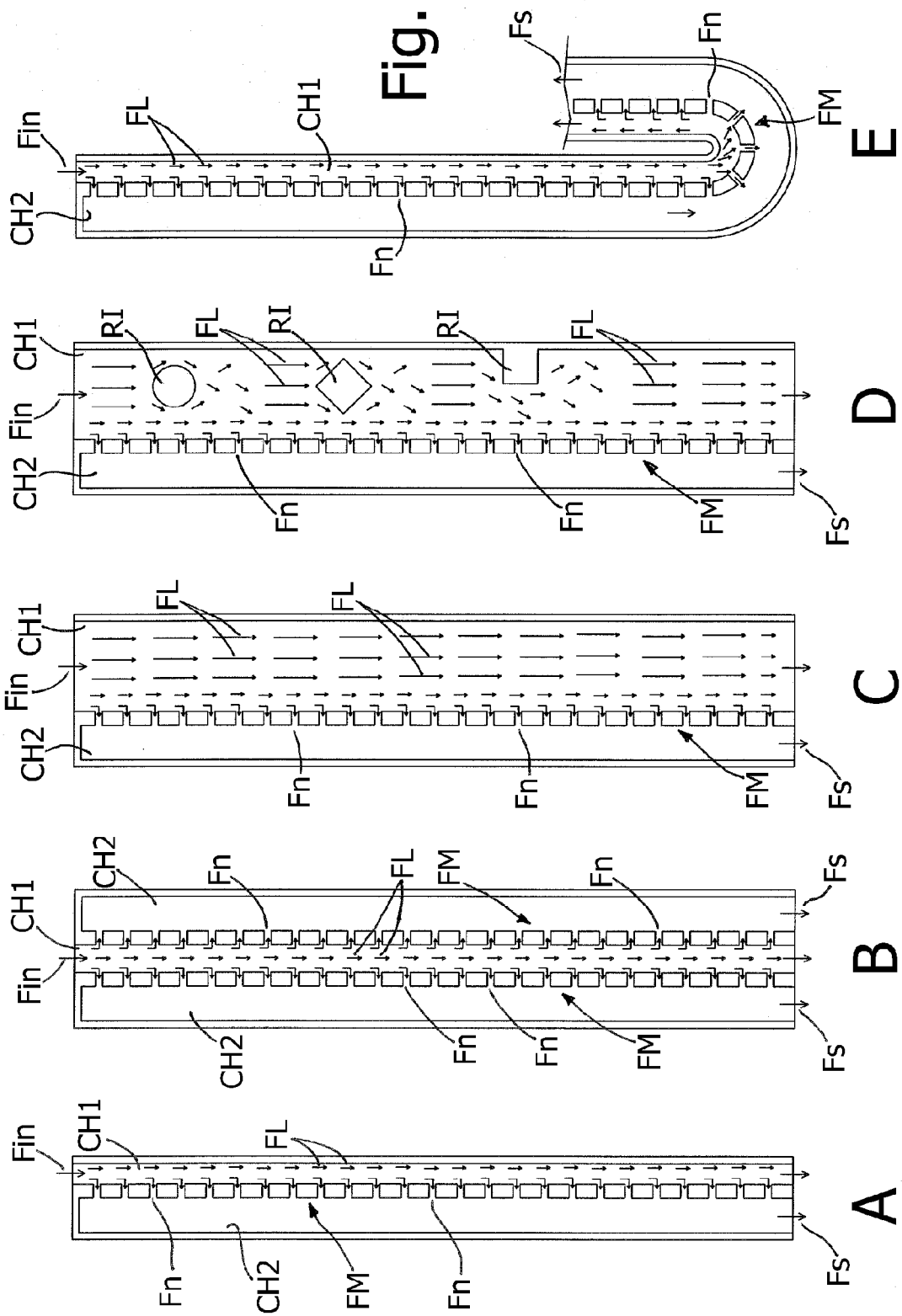
FIG. 2 is a schematic representation of some micro-filtering or micro-separation arrangements according to the known art.

It should be emphasized that the system and the methodology of mixed-flow micro-filtering or micro-separation described herein are not functionally and constructively comparable to known systems and methods of tangential filtering or separation, some of which are schematically illustrated in FIG. 2.

Visible in part A of FIG. 2 is a first typical example of tangential filter, in which a first channel CH1 is provided, introduced into which is the fluid Fin to be treated. Designated by CH2 is a second, discharge, channel, separated from the channel CH1 by filtering means FM, constituted by a wall provided with passageways Fn. Flowing in the channel CH2 is a flow Fs, constituted by a reject portion of the fluid being analysed itself.

The channel CH1 has to be typically very narrow in order to possibly cause all the fluid Fin to pass against the filtering wall FM and in order to prevent the risk of a portion of fluid—designated by FL—from flowing in the form of laminar flow in an area at a distance from the wall FM, such as the wall of the channel CH1 opposite to the wall FM, thus causing a reduced filtering capacity.

In order to reduce said risk, according to a known technique represented in part B of FIG. 2, both of the walls FM that delimit the channel CH1 laterally can be configured as tangential-filtering means; in this case, then, two reject channels CH2 are envisaged. Also in a solution of this sort, however, it is in any case necessary to provide a very narrow channel CH1 in order to prevent central areas of laminar flow FL from being created, with the consequent risk of a part of fluid flowing from the inlet to the outlet of the channel CH1 without coming into contact with the filtering means FM, i.e., with the risk of not all the fluid Fin being treated appropriately.

Consider that, in said type of microfluidic filter, the dynamics of the fluid is regulated by known phenomena, such as the Reynolds number (Re), which substantially identifies ratios between certain physical quantities of the fluid and of the device (for example, speed and viscosity of the fluid, section and/or dimensions of the channel, etc.). For Reynolds numbers $Re \leq 2000$ a flow is typically considered as stable or laminar, such as a flow formed by thin laminas that flow in a direction parallel to the walls or to the direction of the channel. For Reynolds numbers Re>2000 but Re<3000 the flow is, instead, considered as being in a transitional regime, in which small undulations start to form. For Reynolds numbers Re≥3000 the flow is instead considered as being in a turbulent regime, i.e., characterized by a disorderly motion of the fluid threads.

Considering a tangential filter of the type illustrated in part C of FIG. 2, which is substantially equivalent to that of part A but with a duct CH1 for the fluid to be treated that is far wider, it is evident that there is an increased risk of having a laminar flow FL that passes undisturbed between the inlet and the outlet, without coming into contact with the filtering means FM, i.e., without being treated. In said configuration, to prevent said drawback, the speed of the fluid is typically increased considerably in order to increase the Reynolds number and obtain a turbulent motion, which would bring all the fluid into contact with the means FM. Said solution should, however, be avoided in the treatment of biological fluids, such as blood, in so far as the increase in speed brings about an immediate damage to the cells on account of phenomena of lysis. Moreover, to obtain such an increase of speed, given the same cross section of the channel CH1, the pressure of the fluid Fin at inlet should be increased considerably: also this solution is unadvisable in the presence of a biological fluid in so far as the high pressure would damage the cells present in the fluid.

In an attempt to overcome the aforesaid drawback, tangential-filtering devices have been proposed of the type illustrated in part D of FIG. 2, provided with channels made in which are considerable mechanical alterations of the path of the fluid Fin, for example, by introducing restrictions and/or widened areas in the path and/or inserting projections RI that divert the flow. Also said solutions are, however, unsuited to preventing the drawbacks referred to above in so far as they determine mechanical obstructions and/or extensive surfaces against which the cells strike, or restrictions in which local increases in speed are brought about that lead to lysis of the cells. Consider, in this regard that there typically exists the need to be able to treat relatively large amounts of fluid (for example, 5-10 ml) in relatively short times (for example, 15-30 minutes); in this case, the aforesaid restrictions or alterations of the section of passage bring about a deceleration in the flow of the fluid and hence a longer treatment time.

Part E of FIG. 2 illustrates another known technique used in order to possibly cause all the fluid Fin to pass in contact with the filtering wall FM, which exploits the centrifugal forces that are created when the fluid flows in a curved channel CH1, at a relatively high speed. Also in this case it should be noted that the aforesaid high speed entails the risk of lysis, due to the cells that strike against the walls. To obtain said high speed the pressure of the fluid at inlet Fin must moreover be increased, with the risk of further damage to the cells. The path of the fluid to be treated cannot in any case have a significant width or cross section, and consequently it does not enable a high flow rate of blood to pass. Conversely, with very wide ducts, the centrifugal force alone is not sufficient to cause the particles or the threads of fluid to be displaced until they come into contact with the filtering means FM.

In this regard, it should be considered that in microfluidic circuits there typically exist constraints or difficulties in providing relatively deep channels, on account of the processes that typically allow a maximum depth of tens or some hundreds of microns to be reached. In addition, given that the filtering elements should be provided along the side walls of the ducts, according to the known art an increase in the section of flow of the duct should be obtained principally by widening the duct, with the consequent drawbacks indicated above, i.e., worsening of the circulation of the fluid along the filtering walls, and hence inefficiency or ineffectiveness of filtering or separation.

As will emerge also more clearly in what follows, the methodology of mixed-flow micro-filtering or micro-separation proposed according to the aforesaid preferential embodiment of the invention overcomes the limits indicated above of the known art, enabling an efficient and effective treatment of adequate amounts of the fluid under analysis, in relatively short times, at modest pressures and with paths for the fluid having a relatively wide section, and hence with speeds of the flow accordingly reduced, to the advantage of quality of filtering and/or separation, including the integrity of the target particles.

Figure 3:
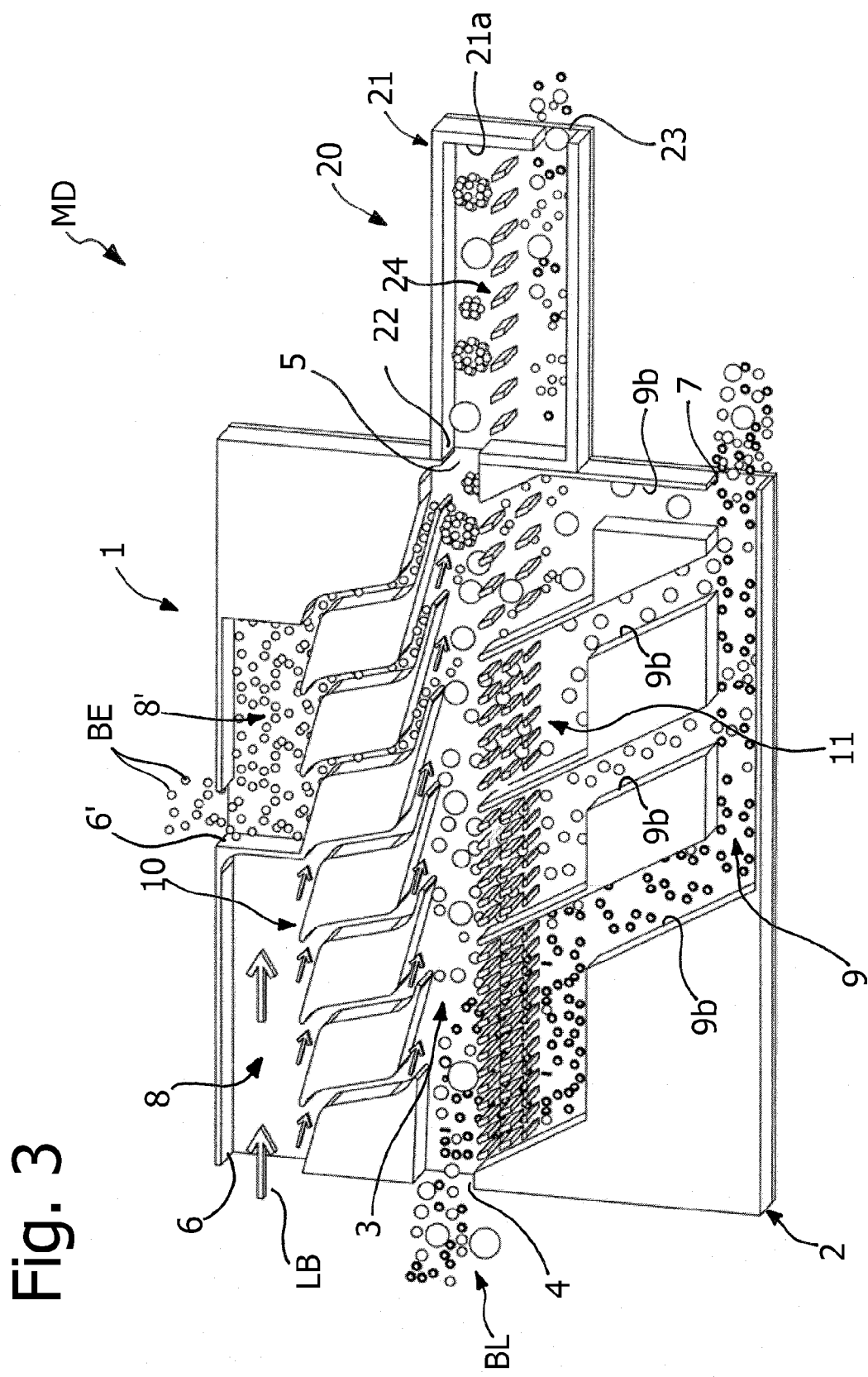
FIG. 3 is a partial and schematic perspective view of a microfluidic device according to the invention.

FIGS. 3, 3A, and 3B represent an example of embodiment of a biomedical microfluidic device according to the invention, substantially a LOC or a µTAS, which is configured for separating a sub-population of particles from a biological fluid. The device in question, designated as a whole by MD, is represented in an extremely schematic form, merely by way example of its working principle, based upon a micro-filtering structure of the type here defined as "mixed-flow". The device MD is represented without a top closing body, or lid, thereof, which is preferably made of transparent material.

The structure of the device MD includes a first section 1, having a first body or main body 2, for example made of at least one from among an elastomeric or silicone material, a vitreous material, a semiconductor material. In what follows, it will be assumed that the material in question is a silicone material, for example polydimethylsiloxane (PDMS), and hence at least slightly yielding and/or preferably transparent. Defined in the body 2—via micromachining techniques—are various functional elements on a nanometric or micrometric scale, comprising at least means for mechanical separation or filtering of the fluid. These means include a first microfluidic channel 3 defined in the body 2. In what follows, also with reference to other embodiments of the invention, the channels provided in the microfluidic devices will be also referred to as ducts or paths.

In one embodiment, at least one inlet portion of the channel 3 has a width greater than 100 µm, preferably between 500 and 20000 µm. Preferably, said inlet portion defines at least one passageway designed to allow at least one type of target particles or tumour cells to pass.

In one embodiment, at least an outlet portion of the channel 3 has a width greater than 20 µm, preferably between 20 and 100 µm. Preferably, said outlet portion defines at least one passageway designed to allow at least one type of target particles or tumour cells to pass.

According to a preferred embodiment, the shape or cross section of the channel 3 is such as to allow a relatively large amount of fluid to flow, preferably of between 2 ml and 10 ml, in a relatively short time, preferably of between 10 and 30 minutes, in particular without significant increase in pressure and/or speed of the fluid in order to prevent phenomena of lysis or damage to the particles or cells.

In the case exemplified, in the body 2 of the device MD the aforesaid inlet portion defines a passageway or first inlet 4 for the introduction of a biological fluid, i.e., a first fluid, into the channel or path 3, and an outlet portion, defining a passageway or first outlet 5 for release from the path 3 of a sample of fluid enriched in the sub-population of target particles. As may be seen, the path 3 extends in length between the portion including the inlet 4 and the portion including the outlet 5 so as to define at least one direction of flow.

In one embodiment, at least one portion of the channel 3 has a depth or height greater than 20 μm, preferably between 30 and 300 μm.

Preferably, the aforesaid inlet portion or the at least one first inlet 4 of the channel 3 has a depth or height greater than 20 μm, preferably between 30 and 100 μm, and the aforesaid outlet portion or the at least one outlet 5 of the channel 3 has a depth or height greater than 30 μm, preferably between 50 and 300 μm, in particular in order to enable also flow of target particles associated to beads in at least a terminal part of the channel 3.

In what follows, it will be assumed that the biological fluid is blood and that the target particles are certain monocytes M and/or tumour cells TC (FIG. 3A).

The device MD further includes at least one second inlet 6, defined at least in part in the body 2, for introduction of a second liquid, i.e., an auxiliary fluid, that is to mix with the first fluid, i.e., the blood, in the first path 3. In the non-limiting example considered, the auxiliary fluid is a liquid buffer agent LB, preferably transparent, for example constituted by a physiological or saline solution, that performs the function of diluting the blood in the path 3 and/or facilitating flow thereof and/or favouring separation of particles. The buffer can contain an anticoagulant and/or other substances designed for the purpose.

The buffer preferably has a predefined conductivity or other physical, chemical and electrical characteristics also in view of operation of electrical arrangements of the microfluidic device, such as a particle counter, a device for alignment of particles, electrical separation means, etc.

The device MD has a second outlet 7, which is also defined at least in part in the body 2, for discharge of a fraction of the blood, in particular a fraction enriched in particles different from the target particles, such as erythrocytes, platelets, and part of the leukocytes (i.e., the leukocytes different from the target leukocytes). The aforesaid discharge fraction of blood forms part of a mixture including also the buffer.

In one embodiment, based upon the aforesaid mixed-flow filtering or separation technique, the first path 3 is at least in part defined in the body 2 between a second microfluidic channel or path and a third microfluidic channel or path, designated by 8 and 9, which are in fluid communication with the inlet 6 and the second outlet 7, respectively. The paths 8 and 9 are substantially adjacent, in particular adjacent in length, to at least a significant part of the path 3. In the example illustrated, the first path 3 is delimited laterally from the second and third paths 8 and 9 by at least one first separation element or lateral delimitation and one second separation element or lateral delimitation, respectively. The three paths and the corresponding lateral delimitations are hence directly made in or deposited on one and the same face of the body 2, which defines the bottom of the paths themselves. Preferably, these lateral delimitations define the minor dimension of the cross section of the first path 3.

In one embodiment, at least one portion of the channel or path 8 and/or of the channel or path 9 has a depth or height greater than 20 μm, preferably between 30 and 30000 μm.

In one embodiment, at least one portion of the channel or path 8 and/or of the channel or path 9 has a width greater than 100 μm, preferably between 200 and 50000 μm.

The first lateral delimitation, designated by 10, has first passageways 10a (FIG. 3A), which connect the first path 8 to the second path 3: in this way, the liquid buffer LB can pass from the path 8 to the path 3 and mix with the blood, preferably with a gradual introduction of buffer along the path 3, i.e., in such a way as to mix the buffer with the blood in a gradual or distributed way along the entire path 3. As has been seen previously, said mixing between the fluid of the path 8 (here the buffer LB) with the fluid of the path 3 (here the blood BL) constitutes an inventive characteristic underlying operation of mixed-flow micro-filtering. For this purpose, as has been seen, the aforesaid mixing occurs preferably in a gradual and/or proportional way and/or along at least a part of the path 3. For said purpose, the passageways 10a are distributed along at least a substantial part of the path 3. Preferably, hence, the liquid buffer is made to penetrate laterally from the path 8 to the path 3, tending to traverse it in the direction of its width (i.e., in the major dimension or major side of the cross section of the path 3).

The second lateral delimitation, designated by 11, has second passageways 11a (FIG. 3A), which connect the first path 3 to the third path 9. Preferably, also the second passageways 11a are distributed along a substantial part of the path 3. In this way, part of the blood-buffer mixture can pass from the path 3 to the path 9 and then be evacuated through the discharge outlet 7.

In one embodiment, inserted into the microfluidic device MD are functionalized particles, such as beads, preferably in a dispersed or non-aggregated form, that are bound to adhere to target particles. The aforesaid beads are bound to aggregate or fix to the target particles within the microfluidic device MD. The beads BE, or rather the ligands that they carry, preferably have a specific affinity with the targets, such as cells, nucleic acids, proteins, or other bio-molecules, giving rise to an aggregate of at least one target particle and at least one functionalized particle. The beads BE used according to the invention can have at least one part sensitive to applied electrical fields so as to enable a fast and effective separation thereof from the rest of the solution analysed, together with the target particles. Preferably, the beads are of a fluorescent type or are functionalized in order to enable a convenient detection, for example of an optical and/or electrical type.

For said purpose, in one embodiment, provided in the body 2 of the device MD is a further inlet, designated by 6', in fluid communication with a further microfluidic path designated by 8'. In the example, also the further path 8' is adjacent in length to the path 3 and is delimited with respect thereto via the lateral delimitation 10, preferably with characteristics substantially equivalent to those described with reference to the path or duct 8. This further path 8' is provided for introduction from the corresponding inlet 6' of a further buffer agent—which may be similar to the one already indicated—containing beads BE, i.e., particles functionalized so as to adhere to target particles, such as tumour cells TC, in order to obtain aggregates of particles. FIG. 4A illustrates for said purpose one such aggregate, as well as a bead BE, schematically highlighted in which are the respective ligands AB, in particular of the antibodies AB.

In the example, the paths 8 and 8' are distinct from one another and are each provided with a respective inlet 6 and 6'; however, said two paths could be replaced by a single path that extends adjacent to the path 3, through an inlet of which there can be introduced indifferently a buffer without beads or a buffer containing beads.

Preferably, also with a view to the possible use of beads, the buffer used is of a type designed to not damage the corresponding functionalized bonds and/or the antibodies. Preferably, the buffer has a predefined conductivity and characteristics such as to not damage said functionalized bonds and/or antibodies, in particular for the purposes of separation and/or detection of the particles.

It should be noted that, according to the known art, the beads are added preliminarily to a blood sample to be analysed, i.e., prior to introduction of the blood into a microfluidic device.

In the case of use of beads BE, the passageways 10*a* will preferably have at least one characteristic dimension—such as the width (horizontal cross section) or the height (vertical cross section) greater than the characteristic dimension or diameter of the beads.

The passageways 11*a* have, instead, at least one characteristic dimension—such as the width or the height—that is smaller than the characteristic dimension or diameter of the target particles, whether these be leukocytes, such as for example altered monocytes M, tumour cells TC, or aggregates of particles, constituted for example by beads BE and tumour cells TC. Merely by way of example, the following cases of target particles may arise:

tumour cells TC, such as epithelial tumour cells, and/or leukocytes, such as monocytes M, having dimensions greater than the section of passage of the passageways 11*a*;

altered leukocytes and/or tumour cells TC, such as epithelial tumour cells, having dimensions smaller than the section of passage of the passageways 11*a*, in which case the beads BE increase the dimensions thereof beyond those of the aforesaid section of passage.

The beads BE used for the purposes of the invention can present electrical characteristics, or a electrical polarity, in order to be attracted and/or repelled electrically, in particular for the purposes of a separation or electrical displacement thereof, and hence a separation or displacement of the particles or target cells TC attached to said beads. As will be seen, the beads BE and/or corresponding target cells TC can be displaced or separated via an electrical field, for example generated via electrodes. For said purpose, the beads BE can advantageously be of an anionic type.

As has already been explained, in one embodiment, the passageways 10*a* are configured for introducing the liquid buffer LB from the path 8 and/or 8' into the path 3 in such a way as to create an albeit minimal deviation or turbulence in the biological fluid that flows in the path 3, in particular in order to cause all the fluid and/or the particles contained therein to flow in the proximity of the passageways 11*a*, for the purposes of an optimal separation. The introduction or mixing of the buffer LB is preferably designed to change the direction of the threads of biological fluid of the path 3 in order to prevent the flow in the path itself from being prevalently laminar or oriented in just the direction of the path 3.

For example, in a preferential embodiment, the passageways 10*a* and 11*a* are oriented in a direction generally transverse to the direction of the flow of the blood-buffer mixture in the path 3, preferably in such a way that the buffer LB leaving the passageways 10*a* of the lateral delimitation 10 imparts on the flow itself and/or on particles contained therein a component of thrust towards the opposite lateral delimitation 11 and/or towards the outlet 5. In this way, the particles or possible aggregates of particles of a dimension smaller than the aforesaid characteristic dimension of the passageways 11*a* are forced to pass into the path 9. Conversely, the particles or aggregates of particles having a dimension larger than the aforesaid characteristic dimension of the passageways 11*a*, which constitute a sub-population of target particles, remain in the path 3, preferably entrained by the buffer and/or by the blood-buffer mixture along the duct 3, and/or towards the outlet 5 that constitutes in itself a area of concentration of the target particles.

It is to be noted in this regard that the passageways 10*a* are preferably distributed along the path 3 and are at least in part oriented so as to have each a direction transverse or angled with respect to the portion of the path 3 into which the single passageway 10*a* gives. The angle between the single passageway 10*a* and the portion of duct 3 into which said passageway gives is preferably between 1° and 89°, in particular between 5° and 45°.

Consider moreover that the path 3 preferably has a section of passage that narrows towards the outlet, in particular in order to compensate for the progressive reduction in the flow rate in the path 3 due to the fluid that exits from the discharge path 9, and/or in order to facilitate passage of a part of the mixture present in the path 3 towards the passageways 11*a*, i.e., towards the discharge path 9.

Likewise consider that the passageways 11*a* and/or the third discharge channel or path 9 are preferably shaped in such a way as to prevent any return of the fluid mixture or reject particles from the path 9 to the path 3, i.e., preferably shaped in such a way as to facilitate the discharge flow towards the outlet 7.

In a preferred embodiment, the device MD includes at least one unit or second section, for collecting or concentrating the sample of target particles, designated as a whole by 20, visible in FIGS. 3 and 3B.

This section has a casing or collection body of its own, designated by 21. The collection body 21 can be configured as a distinct part appropriately coupled, in particular mechanically and hydraulically, to the main body 2, or else it may be constituted by a portion of the same body 2.

The body 21 of the section 20 defines at least one cavity 21*a* with at least one inlet 22, in fluid communication with the outlet 5 of the first path 3. The outlet of the path 3 can—as in the example—correspond to the inlet 22 of the section 20, and vice versa. The body 21 has also a discharge outlet 23, where between the inlet 22 and the outlet 23 separation or filtering means 24 are provided, i.e., means for withholding within the section 20 a sub-population of target particles. In the example, the means 24 basically consist of a filter or sieve, formed by a series of barriers or obstacles 25, which rise from a bottom of the cavity 21*a* of the section 21. In addition and/or as an alternative there may be envisaged other separation means, such as separation means of an electrical type, for example in the form of electrodes for a electrophoresis or a dielectrophoresis (DEP) or for the already mentioned separation via electrical attraction and/or repulsion of the beads BE. In the case illustrated, the means 24 extend longitudinally substantially parallel to the direction of the flow.

The obstacles 25 define between them passageways, designated by 24*a* in FIG. 3B, having a characteristic dimension smaller than the characteristic dimension or diameter of the target particles. In this way, the target particles remain withheld within the section 20, in its part upstream of the separation means 24; at least part of the blood-buffer solution that penetrates into the body 21 can flow out from the outlet 23, with the possible particles not of interest contained therein.

The bottom of the cavity 21*a* can be defined by the body 21 or else by an additional element, such as a substrate made of glass, plastic, or semiconductor material, preferably at least in part transparent. In such a case, underneath the aforesaid substrate there can be provided and/or integrated a lighting source or an optical sensor, designed to irradiate the target particles to facilitate optical analysis thereof; in the case of a semiconductor material, the lighting source can be at least in part integrated or associated to said semiconductor material.

Obviously, in the device MD, i.e., in the section 1 and/or in the section 20, there can be provided also other electrical devices, such as sensor means and/or actuator means and/or electrical separation means, for example, obtained with MEMS (microelectromechanical systems) technology or NEMS (nanoelectromechanical systems) technology, as will emerge from what follows: for such cases, the section 20 can be conveniently provided with electrical-interconnection means. As already mentioned, in one embodiment, at least one part of the section 20, such as its bottom, can be constituted by a substrate made of semiconductor material, for example silicon. Such a substrate can integrate, in addition to the means 24, also devices obtained with MEMS or NEMS technology.

In one embodiment the device, the section 1 and/or the section 20, comprises a sensor or a device—hereinafter referred to for reasons of brevity as "particle sensor" or "particle counter"—configured for detecting and/or counting particles, such as the target particles.

A particle counter of this sort may be of the type comprising electrodes, in particular arranged along at least one part of the path 3 and/or in substantial correspondence or proximity of the outlet 5 and/or of at least part of the section 20, preferably electrodes in the proximity of or in contact with the fluid. In one embodiment the particle counter comprises an electrical circuit designed to detect electrical variations or perturbations, such as variations of impedance or capacitance, caused by the presence or passage of particles or cells in the proximity of an active part of the electrical circuit, represented, for example, by two detection electrodes. The particle counter can possibly be of an optical type, for example provided with a transmitter and a receiver of light radiation, in particular of the type designed to detect an optical variation caused by the presence or passage of at least one cell or particle. The particle sensor could in any case be of some other type and/or designed to detect also other physical quantities, in particular characteristics of the particles, such as dimensions and/or shape.

Preferably, the means of the particle counter that are designed to detect the passage of particles are located in an area of passage or in a duct of capillary dimensions, indicatively comprised between 2 and 100 μm, in particular between 10 and 50 μm, such as, for example, the terminal part of the path 3 or the outlet 5 and/or the inlet portion or duct of the section 20. The provision of a capillary passage or duct may prove useful for aligning or setting in a row the target particles in order to facilitate their detection.

In a preferred embodiment, as represented in FIG. 3, the passageways 10*a* and 11*a* are substantially distributed in a continuous way for at least a significant part of the entire length of the respective lateral delimitations 10 and 11.

In the example illustrated, the lateral delimitation 10 is basically constituted by a series of barriers or obstacles, designated by 12 in FIG. 3A, separated from one another by the passageways 10*a*. The shape of the obstacles 12 can be chosen according to the shape to be assigned to the passageways 10*a*. For example, in a particularly advantageous embodiment, the passageways 10*a* have at least one terminal stretch inclined in such a way that the buffer leaving said passageways imparts on the flow in the first path 3 a component of thrust that facilitates flow thereof towards the outlet 5. Preferably, the passageways 10*a* have the aforesaid terminal stretch inclined in such a way that the buffer leaving said passageways imparts on the flow in the first path 3 also a component of thrust and/or a transverse component and/or a turbulence and/or an irregular motion that will facilitate at least in part flow thereof towards the separation means that include the passageways 11*a*.

An example of said conformation is clearly visible, for example, in FIG. 3A, where the obstacles 12 of the lateral delimitation 10 are shaped in such a way as to define a terminal stretch of the passageways 10*a* that is at least approximately tangential, i.e., almost parallel or slightly inclined, with respect to the main direction of flow in the path 3.

Preferably, the path 3 is without significant obstacles, in order to facilitate flow of the blood from the inlet 4 towards the outlet 5, albeit with relatively low speeds and pressures. The mixed-flow microseparation device MD is hence preferably designed to allow the blood to flow in a gentle way and without any mechanical stresses at least in the path 3 and/or in the means designed to separate and/or withhold the target particles.

As has been said, also in the case of a relatively large width of the path 3, the passageways 10*a* of the mixing fluid, here represented by the buffer, considerably reduces the risk of causing passage of a fair amount of the biological fluid from the inlet 4 towards the outlet 5, without this reaching the separation means or passageways 11*a*.

Also the lateral delimitation 11, in the example represented, is constituted by a series of obstacles, designated by 13 in FIG. 3A, basically configured as vertical projections or appendages, which define between them the passageways 11*a*. The lateral delimitation 11 can hence be configured basically as a wall provided with ducts or passages of predefined or calibrated section.

In one embodiment, at least the passageways 11*a* comprise a number of passageways that are differentiated from one another as regards the dimensions of section or width, in particular a cross section that increases from the inlet 4 to the outlet 5 of the first path 3, as may be clearly seen, for example, in FIGS. 3 and 3A.

The more or less narrow width of the passageways 11*a* of the lateral delimitation 11 depends upon the distance between the obstacles 13 in a direction substantially parallel or inclined with respect to the flow of the path 3.

Merely by way of indication, the distance between the obstacles 13 of at least one stretch of the path 3, i.e., the width of at least some passageways 11*a*, can be of between 2 and 8 μm, in order to enable outlet of erythrocytes when they are oriented horizontally and/or vertically.

In one embodiment, at least the lateral delimitation 11 comprises a number of arrays of obstacles 13 and/or of passageways 11*a*, preferably substantially parallel to one another, as may be clearly seen in FIGS. 3 and 3A. As has been said, the obstacles 13 define between them—in a direction substantially parallel or inclined with respect to the flow of the path 3—the passageways 11*a*. Defined, instead, between the various arrays of obstacles 13 are intermediate channels, one of which is designated by 11*b* in FIG. 3A. The lateral delimitation 11 may in each case comprise just one array of obstacles 13, i.e., be without the aforesaid intermediate channels 11*b*.

From FIGS. 3 and 3A it may likewise be noted that, in one embodiment, the number of the arrays of obstacles 13 differs in different portions of the lateral delimitation 11. In the example illustrated, the lateral delimitation 11 has four portions (not indicated). The first three portions starting from the left (with reference to the figure) consist of three arrays of obstacles 13, whereas the terminal portion, which is closest to the outlet 5, consists of just two arrays of obstacles 13. The distance between the obstacles 13 and between the arrays of obstacles of the various portions increases, in the example, from the inlet 4 to the outlet 5.

Of course, the dimensions of the obstacles 12 and 13 and of the passageways 10*a* and 11*a*, as well as the distances between to the obstacles 12, 13 is chosen as a function of the dimensions of the target particles that are to be withheld within the path 3 and/or according to the dimensions suitable for bestowing an appropriate mechanical strength on the obstacles (in order to confer a higher mechanical strength on the obstacles, these could, for example, be wider than the ones represented, albeit given the same width of the passageways, i.e., maintaining the same distance between the obstacles).

It should moreover be noted that it is possible to provide lateral delimitations 10 and/or 11 that are involved in just a part thereof by respective passageways 10a and/or 11a, or else lateral delimitations 10 and/or 11 that comprise sets of respective passageways 10a and/or 11a distributed along the path 3, but set at a distance from one another (i.e., lateral delimitations 10 and/or 11 that have, for example, at least one part without passageways set between two parts provided with passageways). In embodiments of this sort, the stretch or stretches of a lateral delimitation provided with passageways may also be more or less staggered with respect to the stretch or stretches of the opposite lateral delimitation provided with passageways, and/or one or more stretches of a lateral delimitation provided with passageways can have a development in length different from that of one or more stretches of the opposite lateral delimitation provided with passageways.

Operation of the device MD, as regards separation of the particles, is very simple and occurs according to the principle of the mixed-flow separation already explained previously.

Delivered to the inlet 4, preferably in a continuous way, or possibly in a pulsed way, is a sample of fluid to be analysed, such as a blood sample already partially diluted with a buffer solution and/or an anticoagulant, preferably with the fluid or blood under slight pressure. Likewise, delivered to the inlet 6 is the buffer LB, preferably in a continuous way, or possibly in a pulsed way, and preferably at a pressure slightly higher than that of the blood. If the use of beads BE is envisaged—as in the example—also delivered to the inlet 6' is the corresponding buffer with beads, preferably at a pressure similar to that of the buffer introduced through the inlet 6.

The buffer at outlet from the passageways 10a forces the flow of the biological fluid into the path 3, in part towards the outlet 5 and in part towards the lateral delimitation 11. As has been said, in this way, induced in the flow of the biological fluid in the path 3 is a component of thrust and/or a transverse component and/or a turbulence and/or an irregular motion of the fluid itself.

Possibly the shapes and dimensions of the passageways 10a and/or the pressure of the buffer are such as to induce also a component of suction of the flow of the buffer entering the channel 3 due to the Venturi effect.

The buffer at outlet from the passageways 10a forces the biological fluid and the particles contained in the flow of the path 3 in part towards the lateral delimitation 11, so as to cause particles other than the target particles to penetrate into the passageways 11a and to pass into the path 9, and in part towards the outlet 5, to cause the target particles to arrive at their destination. In other words, the buffer forces the particles and/or the fluid of the path 3 in such a way as to cause them to pass in the proximity of the separation means represented by the passageways 11a.

The fact that the section of the passageways 11a increases along the development of the path 3 means that—tendentially—from the flow passing in the path 3 there will be first evacuated the particles of smaller dimensions and, proceeding along the path 3, there will be evacuated particles of progressively larger dimensions, but in any case of dimensions smaller than those of the target particles.

The residual part of the blood-buffer solution not eliminated through the outlet 7 reaches the inside of the section 20. This residual part is evidently enriched in target particles, even though it can still contain particles that are not of interest. The preponderant part of the solution hence exits from the outlet 23 of the section 20, entraining along with it the particles not withheld by the separation means 24, in particular, those having dimensions smaller than the ones defined by the passageways 24a. The target particles remain, instead, withheld within the section 20, thanks to the separation means 24. This sample enriched in the sub-population of target particles can subsequently be subjected to analysis, according to techniques in themselves known, even without having to extract the particles from the device (for example, for an analysis of an optical type).

As mentioned previously, the channels or paths 3, 8 and 9 are formed in one and the same face of the body 2, which also defines the corresponding bottom surfaces thereof. In one embodiment, at least one of the aforesaid paths has at least two stretches of different depth.

FIG. 3C illustrates such a variant in relation to the first path 3 and to the third path 9. In said figure, it may in particular be noted how a terminal portion of the bottom of the two paths in question is lowered with respect to a corresponding portion of bottom upstream. This stretch of bottom that is lowered or with increased depth, which is substantially in common between the two paths 3 and 9, is designated by 14. Its depth is preferably greater than 30 μm, more preferably, at least 100 μm.

This measurement reduces the risk of clogging of the device, considering the fact that, in the terminal stretch of the path 3, the flow has a increased concentration of particles of larger dimensions: in said area, in fact, there converge the beads BE, which tend to bind to the cells or target particles TC, thus increasing the dimensions thereof.

Moreover, a number of aggregates of particles—for example, each comprising a tumour cell TC and a number of beads—could bind to one another via one or more beads that function as "bridge", as exemplified in FIG. 4B. In this situation there may form a sort of lump, with consequent clogging of the device. The larger section of passage determined by the presence of the stretch 14 having a greater depth or lowered bottom limits the risks of clogging, enabling outflow of lumps and preventing accumulation of particles. To prevent formation of lumps also along the path it is advantageous, as in the case represented in FIG. 1, to inject the beads in a terminal part of the path 3.

It should be noted that the portion 14 with increased depth preferably corresponds to a portion provided with passageways 11a having a greater width, such as passageways 11a having a width equal to or greater than 10 μm. This entails the advantage of enabling the use of a stronger mould, such as a mould with stronger projections, i.e., the projections corresponding to the aforesaid passageways 11a, given that said projections of the mould have dimensions corresponding to the width and depth of the passageways 11a (hence a height greater than 30 μm, but also a width equal to or greater than 10 μm). To a greater height of the projections of the mould corresponds a larger width, and hence a greater strength, preventing the risk of damage to the mould during moulding of the body of the device.

As has been seen, according to one embodiment, the device MD is configured for enabling introduction and/or passage of beads BE, and envisages for the purpose a corresponding dedicated inlet 6'. As has been said, in any case, the beads BE can be introduced within the device MD exploiting the inlet 6 for the buffer, and consequently the prevision of a dedicated inlet 6' and a dedicated duct 8' is not indispensable. It will likewise be appreciated that the beads BE—as likewise the buffer that constitutes the auxiliary fluid—are introduced into the device MD separately from the flow introduced into the first path 3, here the flow of blood, preferably dispersed in another flow, here the flow of the buffer, and that these bind to particles or target cells within the device MD. As has been said, moreover, the device MD and the beads BE can be configured in such a way that the beads can be subjected to forces of attraction or repulsion by means of electrical fields in order to separate particles.

According to a feature that constitutes an autonomous aspect of the invention, the beads BE may be used in order to improve mixing and/or the agitation of the fluid, such as the blood that flows in the path 3. For example, the beads BE can be subjected to forces of attraction or repulsion, designed to determine displacements thereof in the fluid, with consequent agitation or turbulence in the fluid itself, which—as has been said—facilitates separation. It should be noted that the beads aimed at such a use can also being without ligands or antibodies.

FIGS. 5-11 are schematic representations of a biomedical microfluidic device according to the invention, of a general configuration slightly different from those of FIGS. 3, 3A, 3B, 3C, but based upon the same principle of mixed-flow separation, of a continuous or pulsed type. In FIGS. 5-11 there are hence used the same reference numbers as those used in the previous figures to indicate elements that are technically equivalent to the ones already described. In these FIGS. 5-11 the collection section in communication with the outlet 5 is not represented, as neither are connector members at the inlets and outlets of the device.

Figure 5:
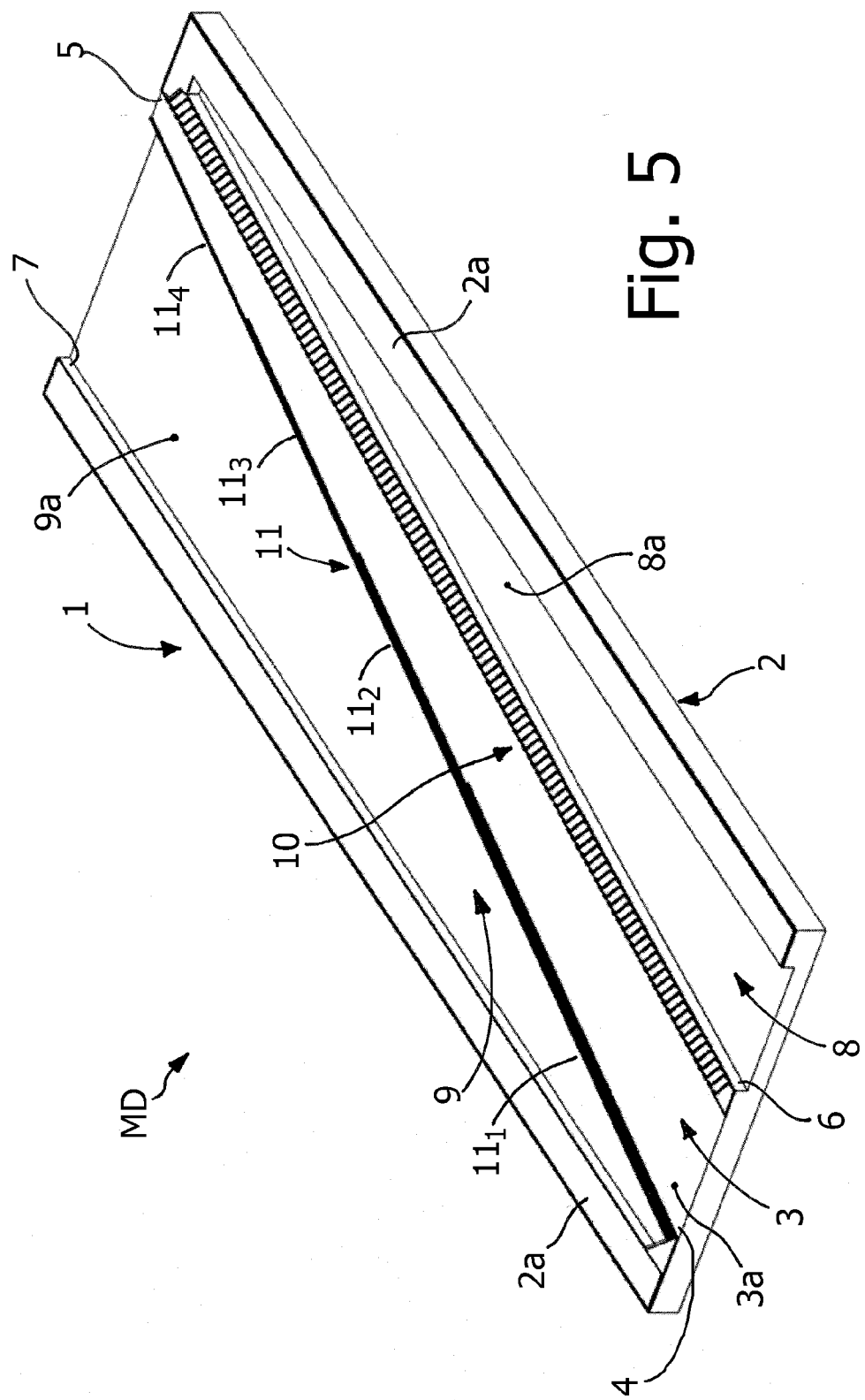
FIG. 5 is a partial and schematic perspective view of another microfluidic device according to the invention.
Figure 11:
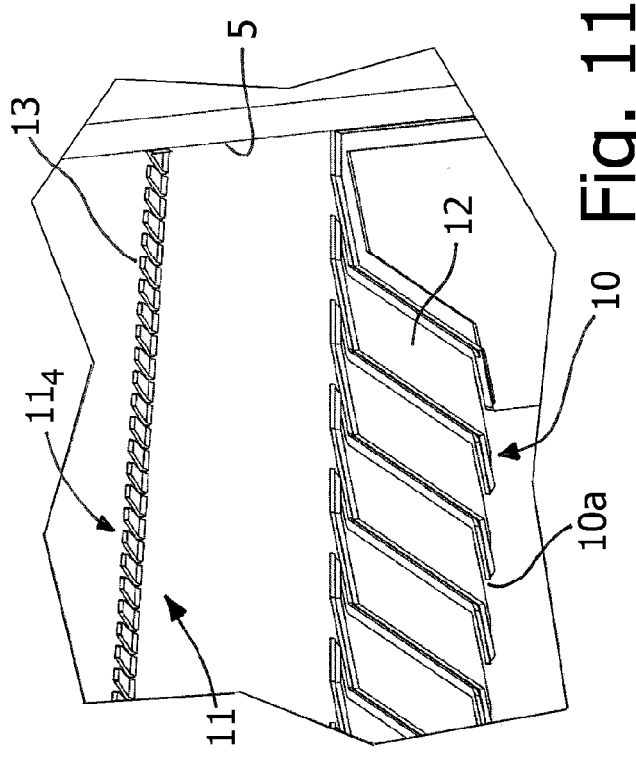

As may be seen for example in FIG. 5, in this device the three paths 3, 8 and 9, as the corresponding lateral delimitations 10 and 11, present a substantially rectilinear development, as in the embodiment of FIGS. 3, 3A, 3B, 3C. Also in this case, the paths and the lateral delimitations are formed in one and the same face of the body 2. In the specific case, at said face, the body 2 has a generally hollowed region, delimited laterally by two walls 2a, and defined within said hollowed region are the paths 3, 8 and 9 with the corresponding lateral delimitations 10 and 11.

Designated by 3a, 8a and 9a in FIG. 5 are the bottom surfaces of the paths 3, 8 and 9. In a possible embodiment the bottom 8a, 9a of at least one of the second and third paths 8, 9 has at least one stretch lowered with respect to the bottom 3a of the path 3. At least one portion of the duct 8 and/or 9 can have, for example, a depth or height greater than 100 µm, such as a height comprised between 500 µm and 30000 µm.

FIG. 5 highlights the specific case in which both the bottom 8a and the bottom 9a are lowered, throughout their development, with respect to the bottom 3a, with the paths 8 and 9 that are hence deeper than the path 3. This feature enables increase in the flow rate of the buffer fluid and of the discharge fluid, at the same time maintaining a contained width of the device.

In the example, the paths 8 and 9 have constant depth. However, a variable depth is not ruled out, for example a path 8 for the buffer with a greater depth towards the inlet 6 and a smaller depth towards the opposite end, and/or a discharge path 9 with a greater depth towards the outlet 7 and a smaller depth towards the opposite end.

In one embodiment, at least a longitudinal portion of the first path 3 has a decreasing cross section and is adjacent in length to at least one of a longitudinal portion with decreasing cross section of the second path 8 and a longitudinal portion with increasing cross section of the third path 9. FIG. 5 highlights the specific case of a path 3 that has a decreasing cross section throughout its development, of a path 8 with a decreasing cross section throughout its development, and of a third path 9 with an increasing cross section throughout its development.

This embodiment, which must be understood as alternative or complementary to the one for the lowered portion of the bottom surfaces 8a and 9a, is useful for a better distribution of the flows and/or of the corresponding pressures. Very schematically, the particular decreasing shape of the path 8 tends to guarantee an optimal flow rate and/or pressure in all the first passageways 10a; also the particular decreasing shape of the path 3 tends to guarantee an optimal flow rate and/or pressure in all the second passageways 11a. The increasing shape of the path 9 tends, instead, to facilitate outflow of the discharge substances and/or to prevent anomalous distributions or increases in the pressure at outlet.

The shape of the path 9 could, however, be different, in the perspective of facilitating outflow of the discharge substances and preventing anomalous distributions or increases in the pressure at outlet, in particular to prevent any return of fluid from the path 9 to the path 3.

Consider that, preferably, at least the paths 3 and 9 are designed to enable maintenance of a pressure in the path 3 that is slightly higher than the pressure of the discharge duct 9, in particular in order to have a minimal difference of pressure, i.e., such as not to induce a damage to the cells or particles, at the same time preventing a return of fluid from the path 9 to the path 3: this is made possible by using the mixed-flow micro-separation system, which, as has already been said, enables use of low fluid pressures.

The decreasing or narrowing shape of the path 3 is moreover suited for the aforesaid integration of a particle counter or particle sensor, i.e., for the definition thereon of appropriate capillary ducts, preferably in the stretch in the proximity of the outlet 5 or corresponding thereto.

Once again in FIG. 5, designated by $11_1$, $11_2$, $11_3$ and $11_4$ are different portions of the lateral delimitation 11, each distinguished by a different cross section of the respective passageways 11a and/or by a different number of arrays of obstacles 13 (see also FIGS. 7-9).

As has been explained previously, in fact, the lateral delimitation 11, or its portions, can be formed by a number of arrays of obstacles 13. In the case represented in FIGS. 5-11, for example, the portions of lateral delimitation designated by $11_1$, $11_2$ and $11_3$ (FIG. 7) and $11_4$ (FIG. 11) consist respectively of four arrays, three arrays, two arrays, and one array of obstacles 13, it being possible, however, for each portion of lateral delimitation $11_1$, $11_2$, $11_3$ and $11_4$ to comprise even just one array of obstacles 13. As has been said, moreover, the cross section of the passageways 11a can decrease from the inlet 3 to the outlet 5 of the path 3.

In one embodiment, at least one first portion of lateral delimitation, for example the portion $11_1$, defines respective passageways 11a, having a calibrated section of a width preferably of between 2 and 8 µm, where in particular said first portion of lateral delimitation extends for at least one third of the length of the entire duct 3 for the fluid; preferably, said first portion of lateral delimitation defines respective passageways 11a designed to allow erythrocytes to pass.

In one embodiment, at least one second portion of lateral delimitation, for example one of the portions $11_2$-$11_4$, defines respective passageways 11a, having a calibrated section of a width preferably of between 2.1 and 25 µm, in particular between 3 and 13 µm. Preferably, said second portion of lateral delimitation defines respective passageways 11a designed to allow at least one type of leukocytes to pass.

In one embodiment, at least one third portion of lateral delimitation, for example one of the portions $11_3$-$11_4$, defines respective passageways 11a, having a calibrated section of a width preferably larger than 5 µm, in particular between 6 and 25 µm. Preferably, said third portion of lateral delimitation defines respective passageways 11a, 5 designed to allow at least one type of target particles or tumour cells to pass.

Also visible in FIG. 9 are the intermediate channels 11b defined between various arrays of obstacles 13. The presence of intermediate channels 11a can prove useful to bring back into the path 3 any possible particles of interest that have accidentally passed beyond the first array of obstacles 13, but not the subsequent array or arrays.

Once again in FIG. 9, it may be noted how, in one embodiment, obstacles 13 of the lateral delimitation 11 can have a lateral profile that narrows from the first path 3 to the third path 9. In this way, the passageways 11a have a generally flared or divergent shape in the direction the channel 9, and this reduces the risk of adhesion of particles, i.e., the risk of clogging. In said embodiment, it may be noted that the obstacles 13 of the lateral delimitation 11 can have a substantially trapezial shape, i.e., side walls inclined with respect to one another, in particular in order to provide passageways 11a having a variable cross section. Preferably, the second passageways 11a have a first inlet section, substantially facing the path 3, having a predefined or calibrated section in order to enable passage or otherwise of given particles or cells present in the fluid. The opposite end of said second passageways 11a, i.e., the end facing the discharge channel 9, has, instead, a larger cross section, in particular in order to facilitate the outflow of the particles towards the discharge and/or to prevent risks of clogging of the passageways 11a. The passageways 11a preferably have a rounded profile or edges at least in the aforesaid first inlet section, substantially facing the path 3, in particular in order to prevent damage to the cells or particles that circulate in the path 3 itself.

Partially visible in FIG. 6 is an upper closing body or lid 26 of the device MD, designed to delimit the paths 3, 8 and 9 at the top. In the example illustrated, the lid is substantially planar, preferably made of a transparent material, for example a plastic or glass, and is applied in a fluid-tight way, for example via gluing or sealing, on the upper surface of the walls 2a (FIG. 6). In one embodiment (not illustrated), the lid 26 can be of an openable or removable type.

In one embodiment, at least one of the lateral delimitations 10 and 11 integrates sealing elements, which are bound to co-operate with the lid 26. Advantageously, at least some of these sealing means are provided integral with the lateral delimitations 10 and 11, and more in particular, with the obstacles 12 and 13 that constitute them. Preferably, the sealing means referred to above have a shape or are made of a material at least in part yielding or deformable. Even more preferably, at least part of the body of the device according to the invention, for example at least the lateral delimitations 10 and 11 and/or the aforesaid sealing means, are made of elastic or elastomer material, such as a silicone or a PDMS (polydimethylsiloxane) or a polysiloxane. In particular, the aforesaid sealing means are made of a single piece or integrated with at least part of the body of the device and/or are made of the same material, preferably integrated or made of a single piece with the lateral delimitations 10 and 11. Additionally, as is visible, the lateral dikes 10 and/or 11 are preferably formed integrally or as a single piece with at least part of the body of the device and/or made of the same material.

From FIG. 9 it may be noted how, in one embodiment, the obstacles 13 are provided at the top with appendages 13a, preferably having a progressively decreasing thickness, such as a substantially triangular or trapezial or semicircular cross section, i.e., having a shape designed to provide respective predefined-deformation seal lips, which are designed to co-operate with the inner surface of the lid 26. Likewise, as may be seen in FIG. 10, in the obstacles 12 that constitute the lateral delimitation 10 there may be integrally made respective upper lips 12a, preferably predefined-deformation ones, in particular having a progressively decreasing thickness, such as a substantially triangular or trapezial or semicircular cross section, that are designed to co-operate in a fluid-tight way with the lid 26.

The seal lips or projections 12a and 13a preferably have a shape such as to be mouldable with movements of the mould in a single direction, i.e., without any undercut, said direction being preferably the same as direction of moulding of the lateral delimitations 10 and 11 and/or of the body 2. The sealing elements 12a guarantee that the flow of the buffer fluid will be oriented in the desired direction, preventing any leakage from the sides.

The obstacles 12 and 13 preferably have a cross section or dimensions larger than those of the sealing elements 12a and 13a, in particular in order to enable the aforesaid calibrated deformation of the sealing elements 12a, 13a without causing any significant deformation of the respective obstacles 12, 13 and hence prevent alterations or deformations of the calibrated passageways 10a and/or 11a. It follows that, even in the presence of stresses and deformations of a part of the aforesaid obstacles, such as the upper sealing portion integrated therein, the calibrated width of the passageways, and in particular of the passageways 11a, remains in any case intact. As may be noted for example in FIG. 9, each fluid-tight element 13a extends between two adjacent passageways 11a and comprises two lateral end edges substantially coinciding with the walls of the passageways 11a defined by the obstacles 13; the lateral edges of two adjacent elements 13a are preferably set at a distance apart as are the obstacles 13. During compressive deformation of the sealing elements 13a, the aforesaid lateral edges could undergo deformation, but the calibrated section of passage of the passageways 11a remains in any case guaranteed thanks to the main body of the underlying obstacles 13, which have a structure such as to not allow deformation in the course of the aforesaid compression.

In the example of FIGS. 5-11, the sealing elements 13a are substantially oriented in the direction of the path 3; i.e., they are substantially transverse to the passageways 11a. Likewise, the sealing elements 12a are at least in part substantially oriented in the direction of the path 3 and/or of the path 8, and in part set alongside the passageways 10a, preferably extending at least along a side of a fair share of the respective passageway 10a.

Sealing elements made in a way similar to the ones previously described are preferably present also in other parts of the device, such as the outer perimeter of the body 2 or the perimeter of the various channels or paths, preferably made of a single piece or integrated in the body 2 of the section 1. Also these further sealing elements are configured to prevent any leakage of fluid towards the outside of the device and/or between the different paths. Elements of this type, configured preferably as seal lips or projections, are designated by SM, for example, in FIGS. 8 and 9.

In a preferred embodiment, in particular in a device with a mixed-flow separation structure, the sections of passage of the paths 3, 8 and 9 and of the passageways 10a and 11a are sized in such a way that:

given the same pressure, the flow rate of the fluid of the path 8 is higher than the sum of the individual flow rates of the passageways 10a, and/or given the same pressure, the sum of the individual flow rates of the passageways 10a is greater than the sum of the individual flow rates of the passageways 11a, and/or given the same pressure, the sum of the individual flow rates of the passageways 10a and of the flow rate of the fluid in the path 3 is higher than the sum of the individual flow rates of the passageways 11a.

Figure 13:
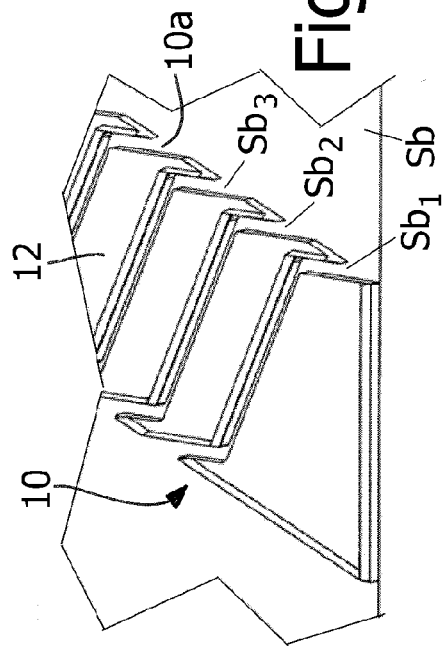
Figure 10:
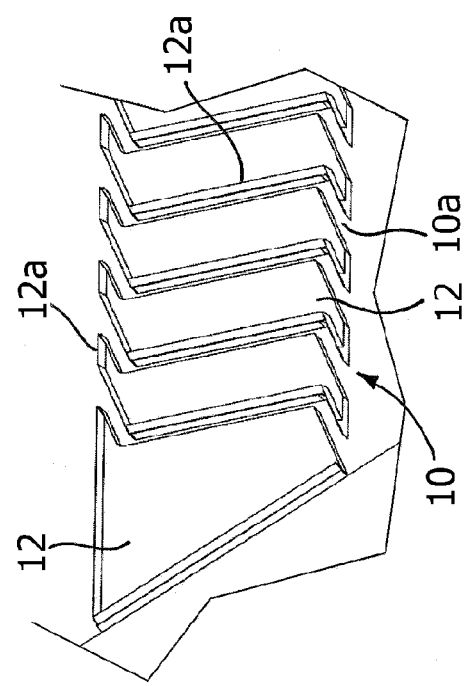
Figure 12:
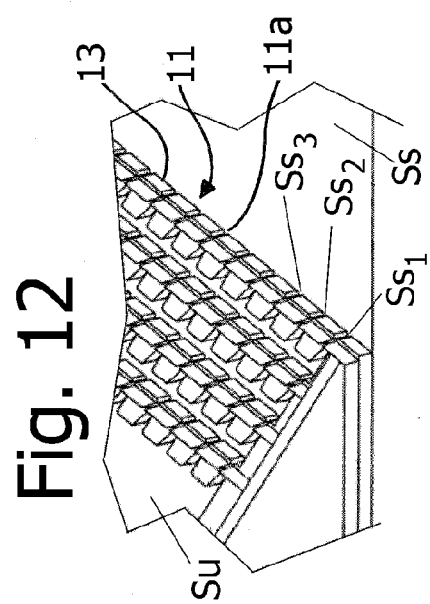

To clarify the above concept, FIGS. 12-14 illustrate portions already highlighted above of the device MD of FIGS. 5-11, with the further indication of some of the sections of passage of interest. In particular, in said figures, Ss is the section of the path 3, Sb is the section of the path 8, $Sb_1$, $Sb_2$, $Sb_3$ . . . are the sections of the passageways 10a, Su is the section of the path 9 and $Ss_1$, $Ss_2$, $Ss_3$ . . . are the sections of the passageways 11a.

In order to prevent any reflux from the path 3 towards the path 8, i.e., to guarantee a uniform flow rate in the passageways 10a, it is preferable for the section of the path 8 to be larger than the summation of the sections of the passageways 10a, i.e.: $Sb > Sb_1 + Sb_2 + Sb_3 + \ldots Sb_n$.

Likewise, in order to prevent any reflux from the path 9 to the path 3, i.e., to guarantee a uniform flow rate in the passageways 11a, it is preferable for the sum of the cross section of the path 3 and of the passageways 10a to be greater than the summation of the sections of the passageways 11a, i.e.: $(Ss + (Sb_1 + Sb_2 + Sb_3 + \ldots Sb_n)) > Ss_1 + Ss_2 + Ss_3 + \ldots Ss_n$.

The above considerations apply in general, given the same pressure, since in this case what carries the most weight is the section of the paths and of the passageways: formulas similar to the ones indicated could, on the other hand, refer also to the flow rates of the paths and of the passageways.

Preferably, in any case, the pressure ($P_8$) in the path 8 will be slightly higher than the pressure ($P_3$) in the path 3, which in turn will be slightly higher than the pressure $P_9$ in the discharge path 9, i.e.: $P_8 > P_3 > P_9$. In this way, it is possible to prevent any fluid present in the path 3 from flowing back into the path 8 and, in the same way, prevent any fluid present in the path 9 from flowing back into the path 3. Said formulas or preferential conditions may be preferably referred also to portions or sections of the device described, such as for example a first half or a second half of the device; this is in particular obtained via the use of said variable dimensions of the paths and passageways.

FIG. 15 regards an embodiment in which the body 2 is set between a lid 26 and a lower body 30. The presence of the lower body 30 can be useful for stiffening the device as a whole—in particular when the body 2 is made of silicone material or some other elastomer—and bestowing a precise planarity for requirements of fluid-tightness. The body 30 is preferably made of a relatively rigid material, such as a plastic material, a metal material, a glass-reinforced plastic, a ceramic material, etc.

In one embodiment, associated to the lower body 30 are at least two electrodes, and in particular a cathode 31 and an anode 32, via which it is possible to apply an electrical field to the fluid that flows in the path 3, which is designed to induce a displacement of particles of the blood and/or of beads BE present in the flow. The electrodes 31, 32, which in the case exemplified are rectilinear, can be used for example to facilitate displacement of particles from the path 3 to the path 9 via techniques of electrophoresis of an insulated type (without contact with the fluid) or of electrophoresis or of the aforesaid attraction and/or repulsion of beads BE, such as beads BE associated to particles or cells TC. As has been said, an attraction or repulsion of beads, performed via appropriate excitation means, can also be used for inducing agitation or turbulence aimed at improving displacement of the fluid towards the lateral delimitation 11 provided with the passageways 11a.

In the embodiment illustrated, in the assembled condition of the bodies 2 and 30, the electrodes 31 and 32 are set substantially corresponding to the lateral delimitations 10 and 11, respectively. Preferably, the electrodes extend parallel to the lateral delimitations, but with the electrode 32 lying underneath the bottom 3a of the path 3 and the electrode 31 lying underneath at least part of the bottom of the path 9.

It should be noted that the electrodes could involve only part of the path 3 and of the path 9, for example a terminal portion thereof. Possibly, electrodes for electrophoresis or dielectrophoresis or separation of beads BE could be provided in the collection section 20.

FIGS. 16-19 are schematic illustrations of a biomedical microfluidic device according to the invention, of a general configuration similar to that of FIGS. 5-11 and provided with the collection section 20. Hence, also in FIGS. 16-19 the same reference numbers are used as those of the previous figures to designate elements that are technically equivalent to the ones already described.

Figures 16, 17:
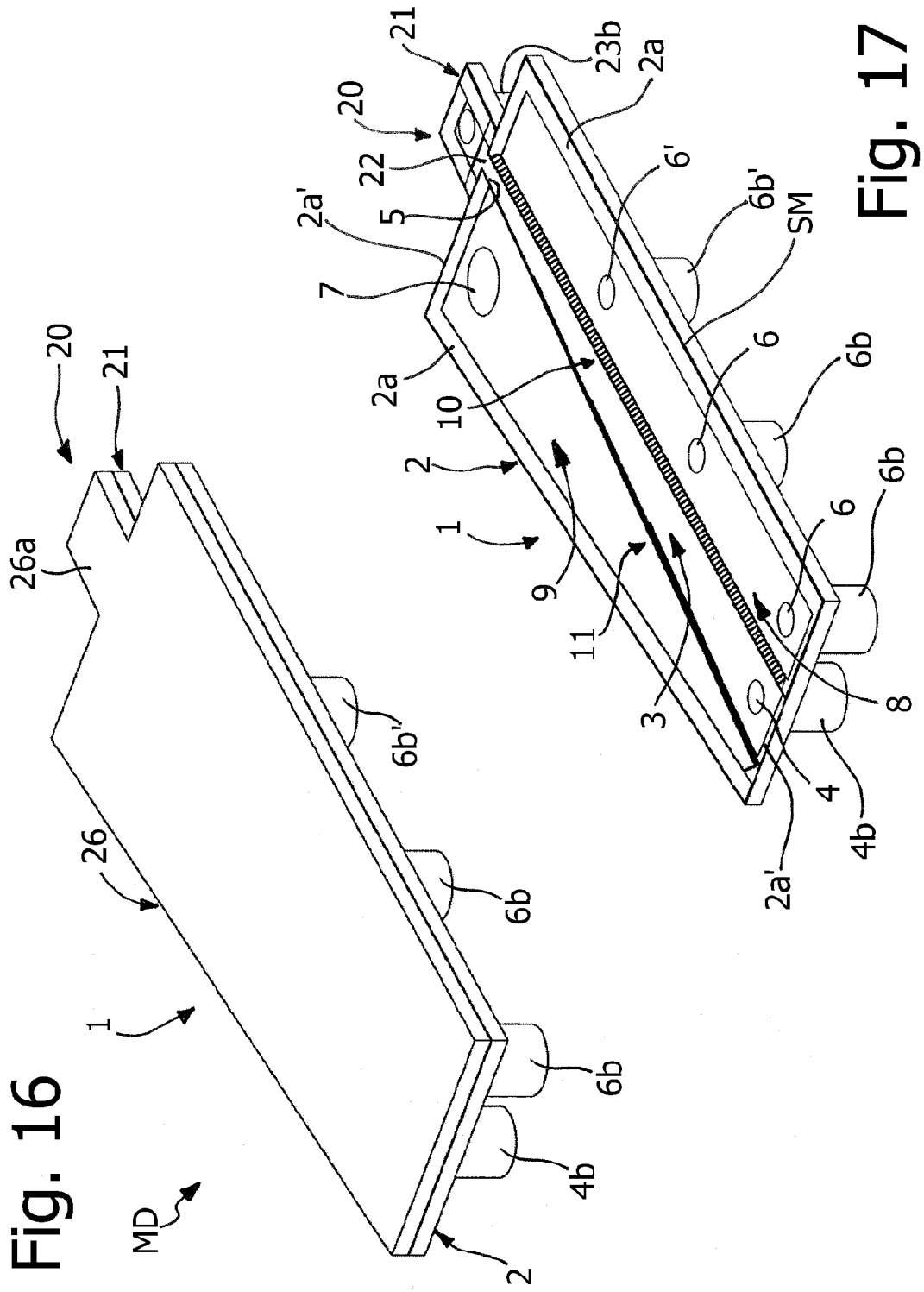
FIGS. 16 and 17 are perspective views of another microfluidic device according to the invention, with and without lid, respectively.

From FIGS. 16 and 17 it may be noted how, in one embodiment, the lid 26 can include a respective portion 26a that functions as top closing also for the collection section. In said embodiment, the body of the lid 26 is preferably made of transparent material, such as glass or transparent rigid plastic. It should be noted that the lid 26a can also be configured as a distinct part with respect to the lid 26, possibly of an openable or removable type, for example for taking out target particles and/or for introducing into the section 20 a culture medium.

In one embodiment, the body 2 has a first face and a second face, defining a thickness of the body itself, and at least one of the inlets and the outlets of the device includes a duct that extends between the two aforesaid faces. FIGS. 16 and 17 represent the specific case in which the inlet 4, the at least one inlet 6, 6', and the at least one outlet 7 are configured as through holes or ducts of the body 2, which open at the top end and, respectively, at the bottom 3a, 8a and 9a of the paths 3, 8 and 9. In the specific case, moreover, also the outlet 23 of the section 20 includes a similar through hole or duct formed in the collection body 21. In the exemplified embodiment, moreover, the aforesaid inlets and/or outlets are in communication with corresponding hydraulic attachments or connectors 4b, 6b, 23b, which can be conveniently formed integral with the body 2 and/or 21; also the outlet 7 is conveniently connected to a similar connector, not visible in the figure.

The presence of the aforesaid connectors, preferably in a lower position, facilitates connection of the device MD, for example on a laboratory apparatus designed for circulation of the fluids and/or analysis of the target particles in the section 21, as well as enabling containment of the lateral overall dimensions of the device itself.

In the embodiment of FIGS. 16 and 17 end walls 2a' are provided (see FIG. 17) that close the paths 3, 8 and 9 at the longitudinal ends.

In one embodiment, a number of inlets 6, 6' for the liquid buffer are provided, positioned in different points along the development of the corresponding path 8. FIG. 17 illustrates the specific case of three inlets set along the path, of which one inlet 6 is in its initial area, one inlet 6 is in its intermediate area, and one inlet 6' is in its terminal area. This arrangement is useful in the case of a relatively narrow path 8, that is shallow and long, i.e., with as small section, in order to guarantee a uniform flow rate of the buffer in the path itself and to prevent areas of negative pressure or non-uniform flow rate, which might cause possible reflux of blood into the path 8. FIG. 17 moreover illustrates the case of a path 8 for the buffer having a substantially constant cross section. As has been explained previously, it is moreover preferable to introduce buffer containing beads in a terminal stretch of the path 3, whence the positioning the inlet 6' in the terminal stretch of the path 8 as represented in FIG. 17. In this configuration, from the inlets 6 there could be introduced buffer, whereas from the inlet 6' there could be introduced a buffer added with beads.

Visible in greater detail in FIGS. 18 and 19 is the collection section 20, with the corresponding area of connection to the path 3. In this case, the mechanical-separation means 24 extend substantially orthogonal to the flow. Also in this embodiment the obstacles 25 preferably integrate sealing elements in the form of upper lips or projections, having functions similar to the lips previously designated by 12*a* and 13*a*; moreover visible are stretches of elements or lips of the type already designated previously by SM.

FIGS. 20-28 are schematic illustrations of another biomedical microfluidic device according to the invention, having a layout of the corresponding paths different from that of the embodiments of the previous figures, but based in any case on the same working principle. Also in FIGS. 20-28 the same reference numbers are used as those used in the previous figures to designate elements that are technically equivalent to the ones already described.

Also in this embodiment, the section 1 of the device preferably comprises a main body 2, defined in which are the microfluidic paths, as well as a lid 26. The device MD comprises a collection section 20, with the corresponding body 21 integral to the body 2 or configured as distinct part with respect thereto. Likewise, the lid 26*a* of the section 20 can be constituted by a portion of the lid 26 or be distinct with respect thereto.

In one embodiment, the first path 3, the second path 8, and the third path 9 present a development that is at least in part substantially spiral-shaped or wound on itself, or in any case preferably have at least in part a curved development. Said shape or development of the paths is principally aimed at containing the overall dimensions of the device.

Figure 22:
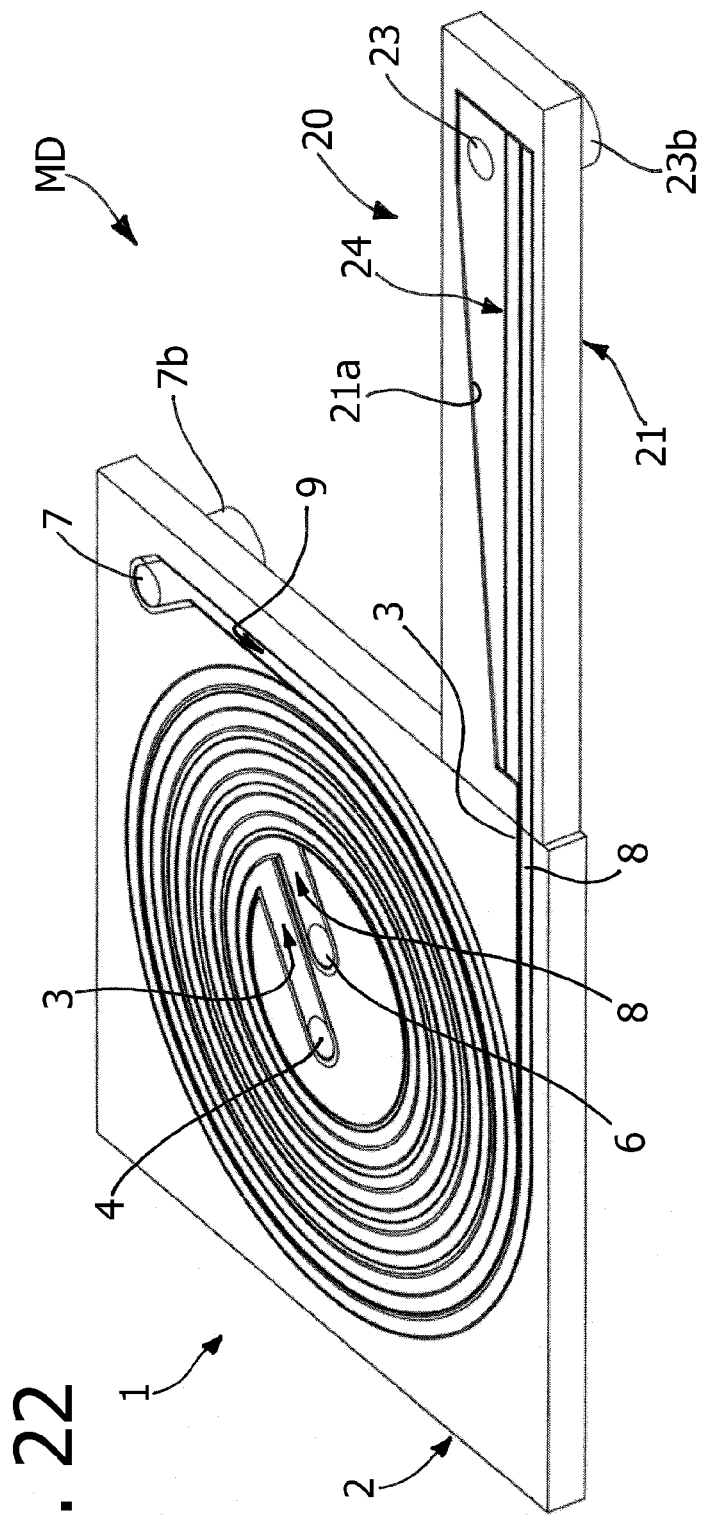
FIG. 22 is a perspective view of the device of FIGS. 20-21, without a respective lid.

FIG. 22 illustrates a configuration of the above sort, where the paths in question are defined on a face of the body 2, with the inlets 4, 6 and the outlet 7 that include a through duct or hole between the two faces of the body 2. Likewise, the outlet 23 includes a through hole of the body 21 of the section 20. Also in this embodiment lower hydraulic attachments or connectors 4*b*, 6*b*, 23*b* are envisaged, which can be conveniently formed integral with the body 2 and/or 21. In FIGS. 20-22 a similar connector 7*b* is also visible, in communication with the outlet 7.

In one embodiment, moreover, the three paths 3, 8 and 9 have a main stretch that is substantially spiral-shaped or wound on itself, or at least in part curved, and at least one of them has a substantially rectilinear stretch. Also said shape or development of the paths is basically provided for containing the overall dimensions of the device.

This specific case is illustrated in FIG. 22, where all three paths have at least one respective substantially rectilinear stretch at the corresponding initial and/or terminal portions.

With reference to a preferred embodiment, the first inlet 4, for the blood, and the second inlet 6, for the buffer, are located in a region of the body 2 around which the first, second, and third ducts 3, 8 and 9 develop in a spiral, i.e., are wound along a curved path, preferably number of times on themselves. As may be noted, the example of embodiment of FIG. 22 also presents said preferential characteristic, which enables simplification and reduction of the dimensions of the device MD as a whole, in particular enabling reduction of the overall dimensions of relatively long paths, albeit maintaining a relatively constant profile along the entire path. Consider, however that the paths of the device according to the invention could also have a different development, albeit suited for reducing the overall dimensions thereof, such as a substantially S-shaped development, or else a development wound along a substantially square or rectangular path, preferably with rounded corners. In this case, the development of the paths would present respective alternations of rectilinear stretches and curved stretches.

It should be emphasized that in the devices considered herein the curved or spiral development of the paths is not exploited for inducing phenomena of separation by centrifugal force. As explained previously, in fact, in the case of the present invention, flows at low speed are preferably adopted to prevent damage to the particles.

The device according to the invention preferably envisages relatively long paths. In particular, a preferred length of the paths 3, 8, 9 is at least 50 times the average width of the path 3; more preferably, the length of the paths 3, 8, 9 is more than 200 times the average width of the path 3.

In other embodiments, once again in the case of a spiral or wound development of the paths, the inlets for the fluids, such as the inlets 4 and/or 6, can be made on the periphery of the spiral (for example, in positions the like the ones of the outlets 5 and 7 of FIG. 22), whereas the corresponding outlets, such as the outlets 5 and/or 7 can be made in the central region of the spiral (for example, in positions like the ones of the inlets 3 and 4 of FIG. 22). In said perspective, it is also possible to provide a configuration with the inlet 6 or 6' for the buffer "opposed" to the inlet 4 for the blood, i.e., with an inlet 4 at the centre of the spiral and an inlet 6 or 6' on the outer perimeter.

Visible in the details represented in FIGS. 23-26 are the various paths, where the path 3 is adjacent in length to the paths 8 and 9 and is laterally delimited with respect to them by the lateral delimitations 10 and 11, with the corresponding passageways 10*a* and 11*a* and the obstacles 12 and 13. In this embodiment, walls 2*a*'' are provided that delimit laterally the ensemble of the three paths and that have a development that is for the most part spiral-shaped. Also the walls 2*a*'' can be provided at the top with seal elements or lips having functions similar to those of the elements previously designated by SM.

From FIG. 25 it may be noted in particular how the path 8 of the buffer is delimited in length between a wall 2*a*'' and the lateral delimitation 10, whilst the discharge path 9 is delimited in length between the lateral delimitation 11 and a wall 2*a*'' wound in a spiral.

Also in this embodiment the sections of the various paths are preferably variable, and in particular the cross sections of the paths 3 and 8 narrow from the inlet 4 to the outlet 5, whereas the cross section of the path 9 widens progressively.

Shown in the non-limiting example illustrated is a spiral configuration with uniform development, i.e., with a constant total width given by the set of the three paths 3, 8, 9. In possible embodiments, not shown, however, there may be envisaged windings in a spiral of a different type, in particular with non-uniform development, for example similar to a hyperbolic or logarithmic spiral, or to the case where paths with variable sections are wound in a spiral (like the paths 3, 8 and 9 of a device of the type shown in FIG. 17, where the total width of the sum of the paths 3, 8 and 9 is not constant, and in fact increases from the end having the inlet 4 to the end having the outlet 5).

The distance between the obstacles 13 can likewise increase in order to define passageways 11*a* of cross section increasing from the inlet 4 to the outlet 5.

The solution with paths wound in a spiral enables containment of the dimensions of the device MD, at the same time guaranteeing the presence of sufficiently long paths for treatment (i.e., it enables, also given the same dimensions with respect to a body configured as in FIGS. 3 to 19, paths 3, 8 and 9 that are decidedly longer to be provided).

The at least in part curved development of the paths tends to keep the larger particles along the path 3, preventing them from being pushed excessively towards the lateral delimitation 11, with the risk of getting stuck in the passageways 11a. In fact, the at least in part curved development of the paths, together with the fact that the obstacles 12 of the lateral delimitation 10 are shaped so as to define a terminal stretch of the passageways 10a that is at least approximately tangential or slightly inclined with respect to the main direction of the flow in the path 3, enables a thrust to be impressed on the particles in a direction that is preferably substantially tangential to the lateral delimitation 11, hence facilitating flow of the larger particles along the duct 3 also in the proximity of the passageways 11a, as shown schematically in FIG. 26, where it may be noted that the buffer LB that exits from the ducts 10a, tends to push the particles towards the lateral delimitation 11, albeit in a direction substantially tangential or very inclined with respect thereto.

With this configuration, certain particles (the smaller ones) pass more easily in the passageways 11a, which have a width such as to let them through, whereas other particles (the larger ones) proceed along the path 3 just as easily, being kept along the stretches of the lateral delimitation 11 provided with passageways 11a that have a width smaller than in the previous stretching, it thus being possible for these particles to flow more easily along the path 3 towards the outlet 5.

Consider in this regard, that, in the example of embodiment exemplified, the passageways 11a are set substantially facing the inside of the spiral, i.e., the flow containing the particles or cells to be rejected moves from the channel 3 to the channel 9 in a direction substantially from the outside to the inside of the spiral, and hence in contrast with the centrifugal force. For this purpose, in the embodiment exemplified, the flows preferably have a speed such as to prevent or contain effects due to centrifugal forces. As in the previous examples, the particles and/or the flow of the first fluid (blood) in the channel 3 are/is subject to the action of the auxiliary fluid (buffer) of the channel 8, which imparts on the flow in the channel 3 also a component of thrust and/or a transverse component and/or a turbulence and/or an irregular motion that facilitates at least in part flow or passage thereof towards the separation means represented by the passageways 11a.

Visible in FIGS. 27-29 is the region of union between the body 2 and the body 21. In FIG. 29 it may be noted in particular how, in one embodiment, both the path 3 of the blood and the path 8 of the buffer are in communication with the inlet 22 of the collection section 20. In this figure it may moreover be noted how the lateral delimitation 10 and the path 8 can extend as far as within the section 20. In this way, the buffer can be used to improve the movement of the flow of blood and/or of the target particles also for the purposes of final filtering or separation, via the separation means 24, of the blood that arrives in the section 20 through the path 3. In FIG. 27 there may moreover be noted a terminal portion of the path 3 having a capillary section of passage, in particular in order to improve the flow of cells or target particles and/or enable improved implementation of the possible means for detection of the particles, such as a particle counter and/or a device for aligning or displacing the particles.

FIGS. 30 and 31 are perspective views of a body 2 according to a variant of the device of FIGS. 20-29. The variant in question is basically distinguished by the presence of the inlet 6' for a buffer containing beads, as described above with reference to previous embodiments. In this case, also the inlet 6' is basically configured as through duct or hole between the two main faces of the body 2, with a corresponding hydraulic connector 6b'. It should be noted, in particular from FIG. 31, how in this case also the path 8' for the buffer containing the beads will have an initial stretch that is substantially rectilinear, a curved stretch adjacent in length to the path 3 of the blood, and a final stretch, once again rectilinear, which extends as far as within the collection section 20. The path 8, for just the buffer, terminates substantially in an area corresponding to the aforesaid initial rectilinear stretch of the path 8'. In particular, the flow of buffer in the path 8' is substantially the continuation of the flow of buffer in the path 8, i.e., the two flows of buffer in the paths 8 and 8' are in series with respect to one another or continuous in order to maintain a uniform flow or action or thrust on the flow of liquid or particles in the path 3.

FIGS. 32-34 are schematic representations of another example of microfluidic device according to the invention, having a configuration substantially similar to that of the devices of FIGS. 20-29 and 30-31.

In one embodiment, the collection section 20 is configured as element that can be separated from the body 2 in which the path 3 is defined.

As already mentioned, the body 21 of the section 20 can be configured as a component distinct from the body 2, mechanically and hydraulically coupled thereto in a separable way, or else be constituted by a portion of the body 22, which is formed integral with a second portion of the body 22.

The device MD of FIGS. 32-34 is obtained according to the second case referred to above, with the body 22 that is pre-arranged for enabling separation between the two aforesaid portions of body, in particular via breaking or cutting.

From the figures it may be noted how, in the example shown, the region "I" of interface or union between the main portion of the body 22 and its auxiliary portion that defines the body 21 of the section 20, has weakening, or pre-breaking, means 2b such as a thinned region or a score line. In the example shown, similar weakening means 2b are envisaged, such as a thinned region or a score line, also in the region of interface or union between the body of the lid 26 and its portion that defines the lid 26a of the collection section 20.

In this way, as may be appreciated, the entire section 20 can be easily separated from the rest of the body 2 and of the lid 26, for example by breaking or cutting, in particular for the purposes of subsequent use in analysis or laboratory activities, such as a use on an apparatus of analysis (for example, a microscope or a optical detection system), or else for a culture of the target cells thus separated. This arrangement or structure, then, in addition to simplifying production of the device, facilitates practical use thereof.

In one embodiment, the body 2 and/or the collection section 20 have capillary ducts or of a reduced cross section in the cutting or breaking area, it being possible for said ducts to be closed mechanically via a deformation of the material of the body 2 or 21, for example made of thermoplastic material. In the aforesaid area these ducts can for example be configured for being squeezed or deformed following upon cutting or breaking in order to substantially close the ducts themselves or else reduce the port thereof, forming a sort of lemniscate, and thus prevent leakage thanks to the adhesion between the molecules of the fluid and those of the material constituting the body 2 or 21.

In one embodiment, the microfluidic device according to the invention comprises identification means. These identification means can, for example, be provided on the main body 2, or on the body 21 of the section 20, or else again on the corresponding lids 25 and/or 25a, or on the lower body 30

Figure 35:
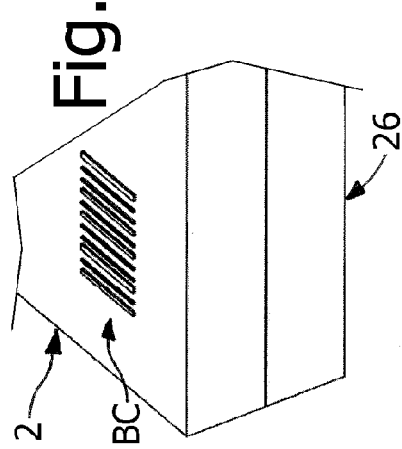
FIG. 35 is a perspective view of a portion of a microfluidic device according to the invention.
Figure 38:
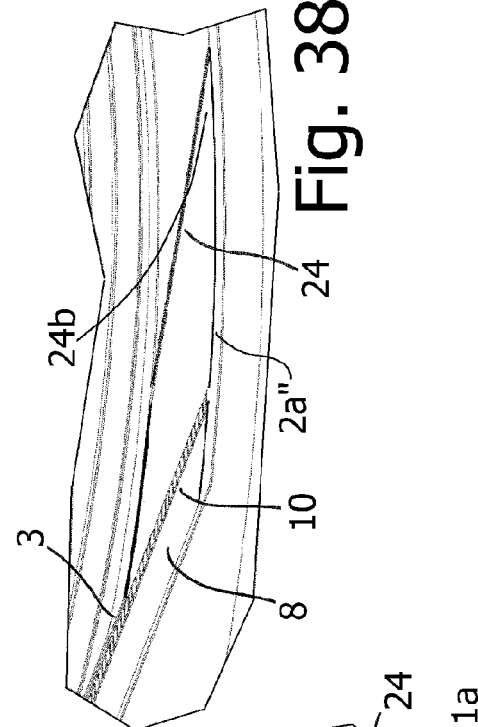
FIGS. 37, 38 and 39 are details at an enlarged scale of the body of FIG. 36.
Figure 37:
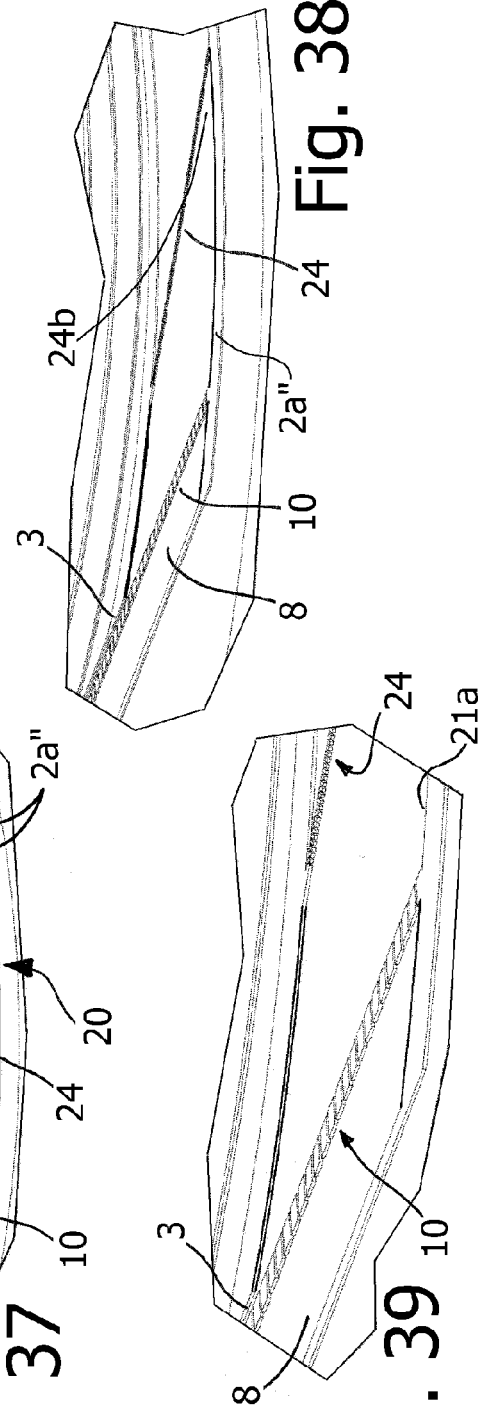

(FIG. 15), for example in the form of labels, or else be printed with a suitable ink, or else be formed integrally in said bodies and/or lids. FIG. 35 regards this second case, and visible therein is a portion of the body 2, integrally defined in which is a barcode BC. A similar barcode can be provided, as has been said, also in the body 21 and/or in the lid 26 and/or in the lid 26a.

The barcode may be obtained for example via printing, deformation, or engraving on at least a part of the body of the device MD, such as the body 2, the body 21, the lid 26, the lid 26a. In this case, the barcode BC can be obtained by providing recesses and/or reliefs on the aforesaid part of body, where each recess and/or relief has a shape corresponding to a corresponding bar of the barcode BC.

In one embodiment, the aforesaid body has, in a point corresponding to a bar of the barcode BC, a thickness smaller than the thickness of areas adjacent to the bars, in such a way that the material that forms the bars can be more easily traversed by an optical ray (basically areas that are transparent and non-transparent to the optical ray are obtained), for the purposes of detection of the barcode BC. In another embodiment, the recesses and/or reliefs are rendered reflecting, for example via reflecting paint or metal inserts, or else are coloured and rendered opaque, with respect to the adjacent areas of the body, which could instead be transparent or reflecting.

In other embodiments, the identification means can comprise an electronic device provided with memory means, such as an RFID device, in particular a device designed to receive and transmit signals and/or data in wired or wireless mode, of the type comprising at least one antenna and/or an appropriate electronic circuit (an example of such an embodiment will be described hereinafter with reference to FIG. 77).

Irrespective of practical implementation, in one embodiment, the identification means contain calibration data or parameters of an apparatus of analysis, on which the device MD or the section 20 are used, such as data or parameters predefined during production of the device according to the invention, in particular designed to enable recognition of the device and/or to provide information to the apparatus of analysis.

In addition or as an alternative, the identification means can be of a type designed to enable modification of the aforesaid data or parameters during at least one step of the cycle of use of the device, for example, via writing of data in a memory of the device, and in particular can contain information identifying the subject to whom the biological fluid belongs and/or the type of sample of fluid and/or the type of analysis to which the sample is to be subjected.

The identification means can then serve to identify the device MD on the basis of the type of measurement for which it is pre-arranged. In this perspective, the apparatus of analysis can advantageously be configured for detecting automatically the identification information, for the purposes of self-calibration and/or for pre-selecting automatically the operation of the apparatus according to the type of device MD (considering the fact that there could exist a number of types of devices MD, for example, ones optimized in terms of shape on the basis of the type of cell to be selected). Such an identification system also enables the control system of the apparatus of analysis to signal a possible erroneous mounting of a device MD, for example, not corresponding to the type of process selected on the apparatus, as in the case of a test selected by the user via a PC program not corresponding to the type of device mounted on the instrument of analysis.

FIGS. 36-39 are schematic representations of another example of microfluidic device according to the invention, of a configuration substantially similar to that of the devices of FIGS. 20-29 and 20-31, in particular a device with mixed-flow separation structure. Also in these figures the same reference numbers are used as the ones already used above to designate elements that are technically equivalent.

According to the embodiment of FIGS. 36-39 (where the lid of the device has not been represented), the body 2 has a substantially circular shape. The collection section 20 is moreover directly integrated in the body 2.

This configuration of the body 2, which could in any case have a shape different from the circular shape, enables placing of the device, possibly without the corresponding lid, on standard supports of analysis used in the bio-technological sector, such as in particular supports of the type known as "Petri dishes" and the like, typically having a cylindrical shape. Alternatively, the device according to the invention can be shaped so that it can be housed in devices or on supports having some other shape, such as Petri dishes of some other type, for example of a squared shape. According to a preferential variant, then, at least a part of the device according to the invention can have a shape similar to or congruent with standard supports of analysis used in the bio-technological sector, such as in particular supports of the Petri-dish type and the like.

This feature facilitates certain operations, such as operations of analysis using standard apparatuses already pre-arranged for the aforesaid supports, such as optical viewing devices (microscopes), or operations of storage, for example using apparatuses already prearranged for said supports.

Said configuration can be particularly advantageous also for the purposes of possible use of the device MD for cell cultures. In such a case the device will be provided, preferably in its section 20, with an inlet or attachment for introduction of a culture medium, as well as at least one aeration duct (not shown).

In the case where an aeration opening is necessary, this will preferably be provided with sealing means that, whilst guaranteeing passage of air, oppose infiltration of foreign substances, such as bacteria. These sealing means can include an air-permeable membrane with calibrated porosity, for example made of Goretex® or similar microporous material. Furthermore, as will emerge hereinafter, the device according to the invention may be provided with valve means between the body 2 and the section 20, and said valve means can advantageously be exploited for the introduction of the aforesaid culture medium. The device according to the invention can also be provided with valve means on the inlets of the body 2, and said valve means can advantageously be exploited to prevent any reflux and/or to enable introduction of fluids—also in a pulsed and/or alternating way—without any reflux by the body 2.

Figure 36:
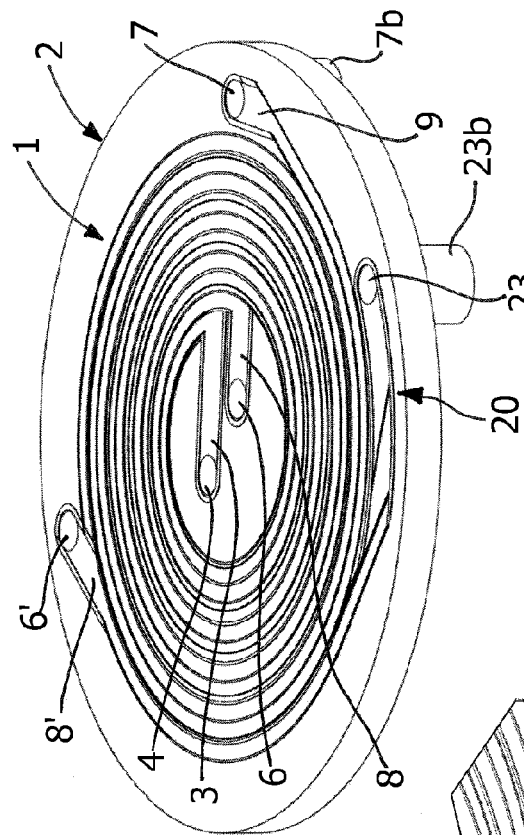
FIG. 36 is a perspective view of a body of another microfluidic device according to the invention.

FIG. 36 illustrates the case of a device MD provided with an inlet 6' and a path 8' for a buffer containing beads, but said elements could of course be omitted, in so far as they are not essential.

In one embodiment, the collection section 20 comprises a terminal stretch of the path 3, defined in the main body 2. This characteristic is included, for example, in the device of FIG. 36 and is visible in particular in the details represented in FIGS. 37-39. In such an embodiment, the section 20 is not separable or distinct from the body 2, but it nevertheless proves useful, both when it is envisaged in devices of a circular configuration (for example, for positioning in Petri dishes), or also in devices of another shape (for example, rectangular), to enable a more convenient positioning on instruments of analysis, such as a microscope.

Figure 39:
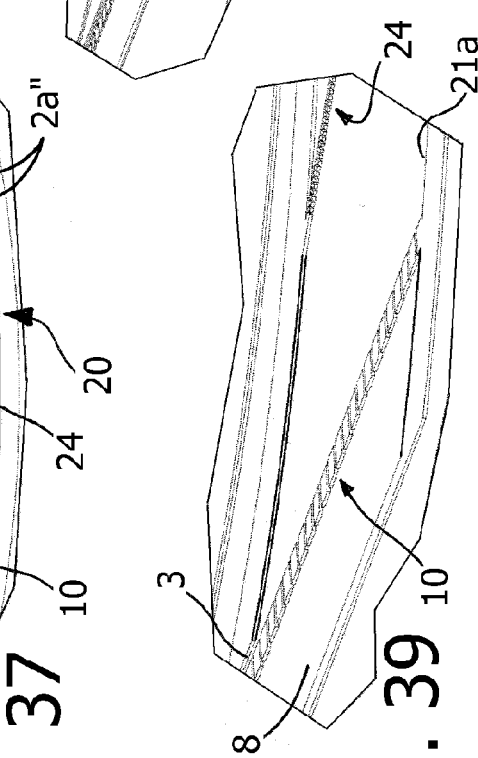

In particular from FIG. 39 it emerges how, also in this case, the path 3 gives out inside the collection section 20, with the lateral delimitation 10 and the path 8 that extend within the section itself.

In one embodiment, or in any case according to a feature that constitutes an autonomous aspect of the invention, at least one portion of the collection section 20 is shaped in such a way as to convey the target cells or particles into a restricted and/or predefined area, in particular in order to improve the concentration thereof and/or facilitate identification thereof. For this purpose, with reference for example to FIG. 38, designated by 24b is such an area for collection of the target particles, which, in this example, is represented by a terminal or restricted portion defined between the separation element 24 and the side wall 2a". As may be seen, the aforesaid collection area can be defined by means of an inclined arrangement of the separation means 24 with respect to the main direction of the flow and/or to a side wall of the collection section, preferably to define substantially an acute angle.

FIGS. 40-45 illustrate a further microfluidic device according to the invention, in particular with mixed-flow structure. Also in these figures the same reference numbers as those of the previous figures are used to designate elements that are technically equivalent to the ones described previously.

In this version of device, and as may be clearly seen from FIGS. 40 and 41, the body 2 is set between an upper closing body or lid 26 and a lower supporting body 30. The body 2 has a general configuration similar to that of the device MD of FIG. 36, even though this is not indispensable.

In one embodiment, the collection section 20 is mounted or at least partially integrated in the lower body 30, with the lower body 30 that is possibly separable from the body 2. FIG. 42 refers specifically to the first case considered, where the body 21 of the section 20—made, for example, of plastic material—is mounted on the lower body 30, in particular but not necessarily in a separable way. It will, however, be appreciated that the body 21 may also be defined integrally in the lower body 30, which is also, for example, made of plastic material or of glass-reinforced plastic. In the non-limiting example illustrated, the lower body 30 is provided with holes, through which respective lower inlet or outlet connectors of the body 2 are to be inserted. These through holes are designated in FIG. 42 by 4c, 6c, 6c' and 7c, respectively, for the connectors designated by 4b, 6b, 6b' and 7b in FIG. 41.

In one embodiment, the collection section 20 is operatively coupled to the lower face of the body 2, and the outlet 5 of the path 3 includes a passage or through hole of the body itself. In one embodiment, the body 2 defines a housing in which the collection section 20 is at least partially received.

The device MD of FIGS. 40-45 includes both of these characteristics, as for example is clearly visible in FIG. 44, where designated by 5 is the through hole of the body 2 that provides the outlet of the path 3, whilst designated by 33 is a housing in which part of the body 21 of the collection section is designed to be received, in particular but not necessarily in a removable way. In this embodiment, the section 20 does not require a respective lid. In this embodiment, the outlet 5 gives out into the housing 33.

The collection section 20 is here configured as a distinct part both with respect to the body 2 and with respect to the lower body 30 and has a respective collection body 21. The bottom of the cavity 21a of the body 20, integrating the separation means 24, can be formed integrally by the body 21 or, as in the case shown, be constituted by a respective substrate 40, for example made of glass or semiconductor material, defined on which are the means 24. In the case of use of a semiconductor material, in the aforesaid substrate there can be integrated electrical and/or electronic and/or electromechanical devices, such as for example lighting means, optical sensor means, electrodes for electrophoresis or separation of particles or cells, electrodes for attraction and/or repulsion of beads BE, electrodes for detection and/or counting and/or alignment of particles or cells, solenoid valves and/or miniaturized electric pumps, etc., preferably obtained with MEMS or NEMS technology. In the case of a glass substrate, electrical and/or electronic devices can be positioned in the body 21 underneath the aforesaid substrate. In the case where the section 20 includes also sensor means for the analysis of the sample of target particles, as mentioned previously, it is not indispensable to envisage the possibility of removal of the section 20 from the section 1.

In one embodiment, such as the one represented in FIGS. 40-45, the section 20 is provided with a respective lower outlet connector. This outlet connector, which is preferably formed integral with the body 21, is clearly visible in FIG. 45, where it is designated by 23b, and is in fluid communication with the outlet 23 of the section 20. In the case where the body 21 of the section 20 is defined integrally in the lower body 30, also the connector 23b will be preferably made of a single piece with the lower body. Furthermore, in the case where the bottom bearing the separation means 24 is configured as substrate apart with respect to the body 21, said substrate will be provided with a suitable passage or through hole for discharge of the fluid in excess from the sample of target particles, with said hole that will come to correspond to, or in any case be in fluid communication with, the outlet 23 formed in the body 21.

As may be appreciated in particular from FIGS. 41 and 42, in the assembled condition of the device, the body 21 of the section 20 is coupled to the lower body 30 with the outlet connector 23b of the section 20 that is fitted through the hole designated by 7c (FIGS. 41 and 42) of the body 30, whilst the top part of the body 21 is received at least in part in the housing 33 (see in particular FIGS. 43 and 44).

In one embodiment, the collection section 20 is mechanically and hydraulically coupled to the body 2. Said characteristic is, for example, present in the case of the device MD of FIGS. 40-45, where the housing 33 enables both a hydraulic connection and a mechanical connection of the body 21 to the body 2. In a preferred embodiment, as has been said, the body 2 is made of an at least slightly elastic material, such as a silicone material, and this facilitates precise coupling in a fluid-tight way of the section 20 to the body 2; obviously, there is nothing to rule out providing specific sealing means, for example one or more gaskets, which operate along the periphery of the body 21 at a part thereof operatively inserted in the housing 33.

In the assembled configuration (see FIG. 43), the section 20 is set underneath the outlet hole 5 of the path 3. It may be noted that, as has been explained previously, in the hole 5 there may possibly converge also the duct 8 or 8' for the buffer. In particular, underneath said hole 5 there will be located the portion of the section 21 that is set upstream of the separation means 24.

In one embodiment, mounted on the lower body 30 are electrical and/or electronic components. This is, for example, the case of the device of FIGS. 40-45, in which, in addition to the section 20, mounted on the lower body 30 are electrical components, comprising the electrodes 31, 32 for carrying out a dielectrophoresis along at least one stretch of the path 3, as well as terminals 34.

In one embodiment, at least one of the upper body 26 and the lower body 30 is configured at least in part for performing printed-circuit functions. Also said characteristic is present in the case of the device of FIGS. 40-45. As may be clearly seen from FIG. 42, the electrodes 31 and 32 are here configured as electrically conductive paths deposited or in any case directly formed (for example, via serigraphy or etching) on the face of the lower body 30 facing the body 2. The electrodes 31 and 32 are electrically connected to the terminals 34 of a connector, which provide means for electrical interconnection of the device MD, for example, to an analysis or control apparatus. The terminals 34, which are substantially of a pin type, pass right through the thickness of the lower body 30, with respective parts projecting from both faces of said body 30. Hence, preferably provided in the lower face in the body 2 is at least one housing designed to receive partially also components other than the section 20, mounted on the body 30. A housing of this sort, which receives part of the terminals 34, is designated by 35 in FIG. 44. Obviously, in the case where on the lower body 30 other electrical and/or electronic components are mounted, such as for example an integrated circuit, the housing 35 can have dimensions larger than the ones exemplified, or there may be envisaged a plurality of housings having a shape and dimensions adequate for the components to be partially received.

On the opposite side of the lower body 30 the terminals 34 project, to a significant extent, within a connector body, designated by 36 in FIGS. 41-43. The connector body 36, here having a quadrangular section, can be formed integral with the lower body 30 or else be configured as a distinct piece.

In the case where the collection section 20 integrates electrical and/or electronic components, on the face of the lower body 30 having functions of printed circuit there can also be provided connection paths, for electrical interconnection of the unit 20. This embodiment is also illustrated in FIG. 42, where the aforesaid connection paths are designated by 37. In this embodiment, the body 21 has respective exposed terminals or contact elements (not visible), which, in the assembled condition, are in electrical contact with the paths 37, for the necessary supply and/or for conveying signals to and from the electrical and/or electronic means present in the section 20.

It should be noted that a printed circuit or PCB can be configured as additional component, for example made in a lower body 30, or in a lid 26, or else can be made directly on the body 2, when this is made of a suitable material, such as, for example, glass or silicon. Also in this latter case, the conductive paths can be obtained, for example, with serigraphic technique directly on the body 2, possibly provided at least in part with an appropriate insulating layer.

Also the lid 26 may possibly be configured at least in part for performing printed-circuit functions, as has been described for the lower body 30, with electrical and/or electronic components mounted thereon.

In one embodiment, between the body 2 and the body 21, i.e., the collection section 20, there may be provided an electrical interconnection. For example, with reference to embodiments like the ones of FIG. 16-17 or 20-21, the device MD can comprise a printed circuit or PCB with a portion that extends astride of the body 2 and of the body 21, said PCB performing functions of interconnection between electrical/electronic parts belonging to the body 2 and electrical/electronic parts belonging to the body 21. In such a case, possibly, in the area of interface between the bodies 2 and 21 the aforesaid printed circuit can be pre-arranged for enabling breaking or cutting, as has been described previously with reference to FIGS. 32-34 for the bodies 2 and 21.

Of course, also with reference to other embodiments illustrated, an interconnection between electrical/electronic parts of the body 2 and electrical/electronic parts of the body 21 could be obtained via a corresponding connection system, for example of the male-female type.

In one embodiment, the device according to the invention comprises at least one of an electric heater and a temperature sensor. Said means can be useful for keeping the biological fluid at a pre-set temperature (for example, approximately 37° C.) during analysis.

The heater and/or the temperature sensor can be mounted directly on the body 2 or, as in the case exemplified in FIG. 46, in a lower body 30 of the device. FIG. 46 regards precisely the case of positioning of a temperature sensor TS, for example, of a PTC or NTC type, and of an electric heater EH, for example in the form of a serigraphed resistor, positioned on a lower body 30 like the one described previously with reference to FIGS. 40-45, for example made of glass. It should be noted that also the heater HE could be of a PTC type, which can also be possibly obtained with the serigraphic technique. In the case of a PTC heater, it is not necessary to purposely provide a temperature sensor TS, owing to the characteristics of self-regulation in temperature of a positive-temperature-coefficient resistor. The temperature sensor TS could in any case being useful also for other functions and/or for a more correct processing of the data.

FIGS. 47-49 illustrate another microfluidic device according to the invention, in particular a with mixed-flow microseparation structure. Also in these figures the same reference numbers as those of the previous figures are used to designate elements that are technically equivalent to the ones described previously.

As has been seen previously, in the device of FIGS. 40-45 the body 21 of the collection section 20 is configured as component mounted or made at least in part on the upper face of the body 30, i.e., the one facing the body 2. FIGS. 47-49 refer to a device conceptually similar to that of FIGS. 40-45, but in the case of mounting or integration of the body 21, and hence of the section 20, on the bottom face of the body 30.

As may be seen in FIG. 48, the bottom face of the body 30 may possibly be configured as a printed circuit, mounted on which are, in addition to the section 20, also other electrical and/or electronic components, such as the terminals 34 of the connector 36 and an integrated circuit 38. It should be noted that in FIG. 48 the electrically conductive paths for the connection of the various electrical and/or electronic components have not been represented.

It should be noted, in particular in FIGS. 48 and 49, how projecting from the body 21 of the collection section 20 are terminals or contact elements 39 for connection with corresponding paths made on the bottom face of the body 30, said collection section 20 being substantially configured as an electronic component of the surface-mount type. Also in this embodiment, the bottom body 30 has a respective connector body 36, projecting within which are the interconnection terminals 34 of the device MD towards the outside world, for example, towards an apparatus of analysis. The body 30 has a passage or through hole 5b that, in the assembled condition of the device MD, occupies a position corresponding to the outlet hole 5 of the path 3; via said hole 5b the fluid reaches the section 20.

In one embodiment, the collection section of the microfluidic device according to the invention includes a substrate made of semiconductor material, in particular silicon, integrating at least one of a fluidic device, an electro-mechanical device, an electrical device, an electronic device in miniaturized form, a device for transmitting and/or receiving data, MEMS or NEMS devices, as already mentioned previously.

Figure 51:
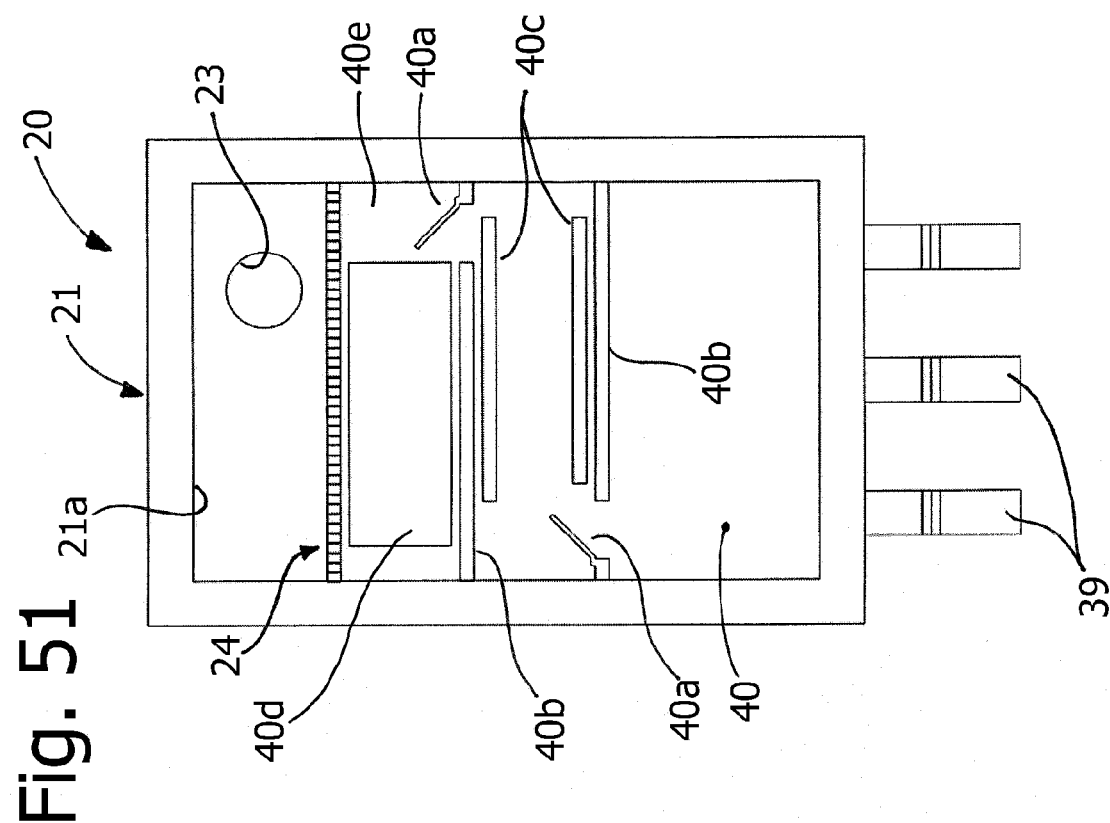
FIG. 51 is a plan view, at an enlarged scale, of the part of device of FIG. 50.
Figure 58:
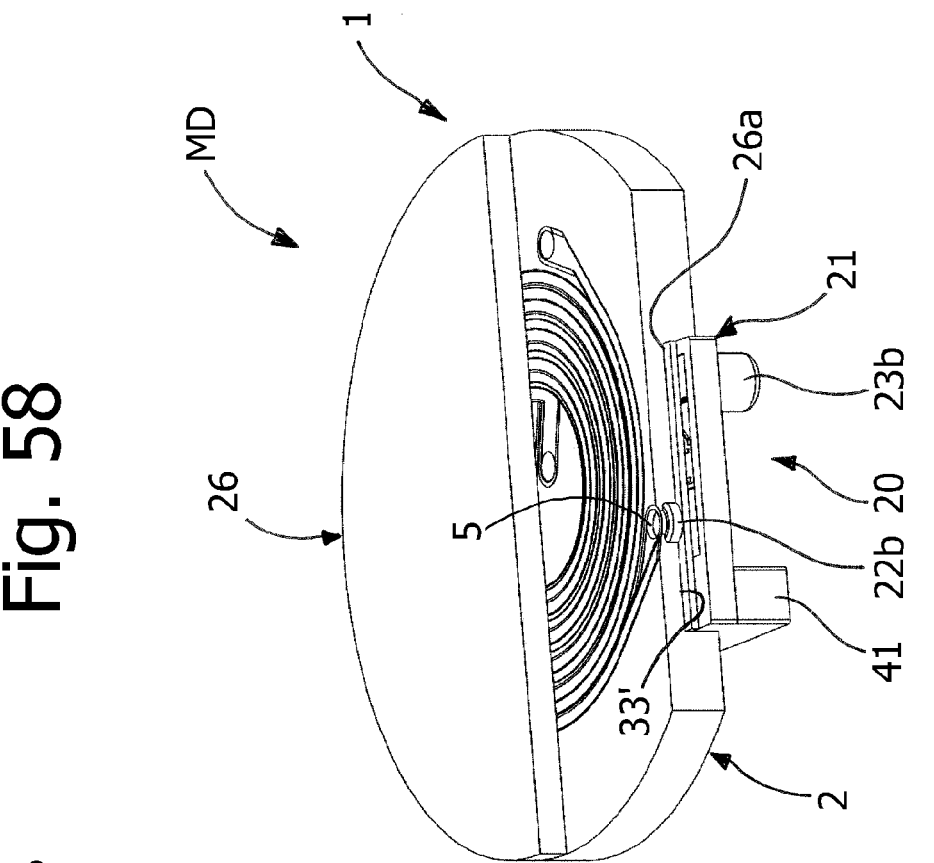
FIGS. 57 and 58 are an exploded view and a partially sectioned perspective view, respectively, of the device of FIGS. 55 and 56.
Figure 57:
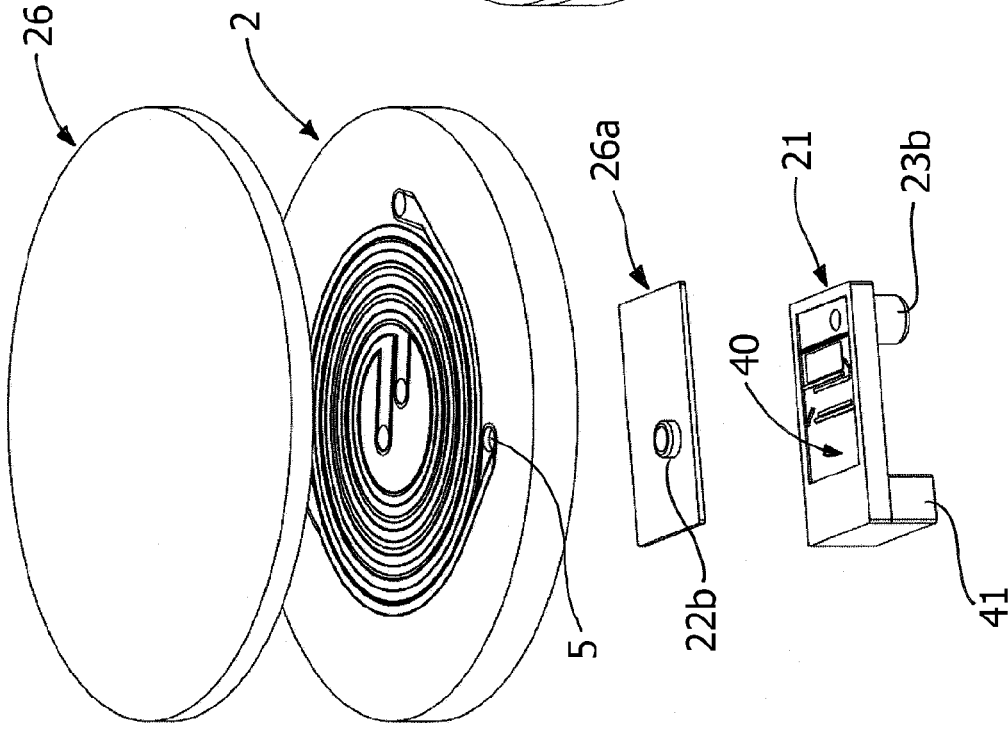

Such a case is exemplified in FIGS. 50 and 51, which regard a collection section 20 that can be used, for example in combination with the devices MD of FIGS. 40-45 or of FIGS. 47-49. The idea of providing a substrate made of semiconductor material, and in particular silicon, integrating electrical and/or electronic and/or electromechanical devices can in any case be applied also to other embodiments of the invention, by providing the section 1 or the section 20 with electrical-interconnection means.

In the embodiment of FIGS. 50 and 51, the section 20 has a respective collection body or casing 21, made, for example, of plastic material, which defines at least in part the cavity 21*a*. The bottom of said cavity is, in the example, formed from a silicon substrate, designated as a whole by 40. The body 21 that houses the substrate 40 integrates at least partially hydraulic ducts, such as the outlet hole 23 and the corresponding connector 23*b*. Moreover associated to the body 21 are the electrical-connection means 39, connected to the substrate 40, for example via wire bonding, in an area protected from the flow of fluid.

In the example, the substrate 40 is then microprocessed to define one or more miniaturized devices. In general terms, these devices can comprise a filter or separation means, an integrated circuit, a device for measuring and/or processing information and/or physical quantities, a lighting device, an optical detection device, a storage device, a device for counting and/or alignment and/or detection of characteristics and/or of the type of particles, or a sensor device in general.

In the specific case represented, in addition to the means 24, in the substrate 40 there may be identified two MEMS micro-valves 40*a*, walls 40*b* that form a microfluidic channel, a pair of electrodes 40*c* for electrophoresis and/or cell detection, a processing and/or sensor part 40*d*, which can hence integrate microcontroller and memory functions, as well as lighting means and sensor means. In the example, this unit is represented schematically upstream of the means 24, but the same unit, or a similar unit, may be provided downstream of the means 24. In one embodiment, the part 40*d* comprises lighting or excitation means and/or means designed to highlight the cells or particles, present in particular in the chamber 40*e* that is comprised between the microvalve 40*a* and the separation means 24. The aforesaid lighting means, for example comprising one or more light-emitter elements of a LED or solid-state type, are preferably designed to generate at least one wavelength of the electromagnetic spectrum suited for the purpose, such as a wavelength designed to excite appropriately beads BE attached to cells TC, or designed to highlight predefined characteristics of the particles or cells, such as the shape.

In the part 40*d*—which can be obtained according to techniques known in the sector of manufacture of silicon-wafer microcontrollers—may be in part insulated and in part in contact and/or in a position corresponding to the fluid, preferably by integrating transmitter and/or receiver means for exchange of information with an external transmitter and/or receiver device, for example provided on an apparatus of analysis. In such an embodiment, then, the identification means of the device previously described and exemplified in the form of a barcode, can be of an electronic type and include means for transmitting (and possibly receiving) signals, for example for sending data identifying the device MD and/or results of measurements/analyses conducted within the section 20 and/or other information or data, and for possibly receiving identification information, configuration and/or setting parameters, or specific commands for electrical/electronic components internal to the same section 20.

Given that in the silicon substrate 40 there may conveniently be provided nonvolatile-memory means, in the substrate itself there may also be advantageously implemented an RFID device, for example of the type mentioned previously, preferably containing identification data, regarding, for example, information representing the sample under analysis, the type of analysis to which the sample is to subjected, data or parameters for calibration of an apparatus of analysis, data identifying the subject to whom the biological fluid belongs, etc.

The sensors integrated in the silicon substrate 40 may comprise means for counting particles, for example obtained with electrodes that change their behaviour, such as the electrical resistance or the capacitance or the oscillation, in proportion to the cells with which they come into contact. There could advantageously be integrated in the substrate 40 also microfluidic devices or miniaturized sensors designed to control the flow rate and/or pressures of the circulating fluids, as also the corresponding temperature and/or other relevant physical parameters.

In one embodiment, the collection section 20 comprises a casing body 21 configured as a distinct part with respect to the body 2, which integrates at least partially hydraulic ducts and electrical-interconnection means. Such an embodiment is, for example, represented in FIGS. 52-54, where the same reference numbers are used as those of the previous figures.

In this embodiment, the section 20 has a respective body 21, for example made of plastic material, which defines both a lower outlet connector 23*b* and a connector body 41, within which respective electrical terminals 42 project. These terminals 42 are connected to electrical and/or electronic components present within the body 21, for example integrated in miniaturized form in a silicon substrate like the one previously designated by 40, as may be seen for example in the exploded view of FIG. 54, provided with the corresponding outlet hole 23 in fluid communication with the outlet connector 23*b*. Alternatively, the bottom of the cavity of the body 21 can be defined by a glass substrate, in which case the electrical and/or electronic components of the section 20 may at least in part be positioned underneath said glass substrate (see, for example, the foregoing part of description in relation to the collection section of FIG. 45).

Figure 52:
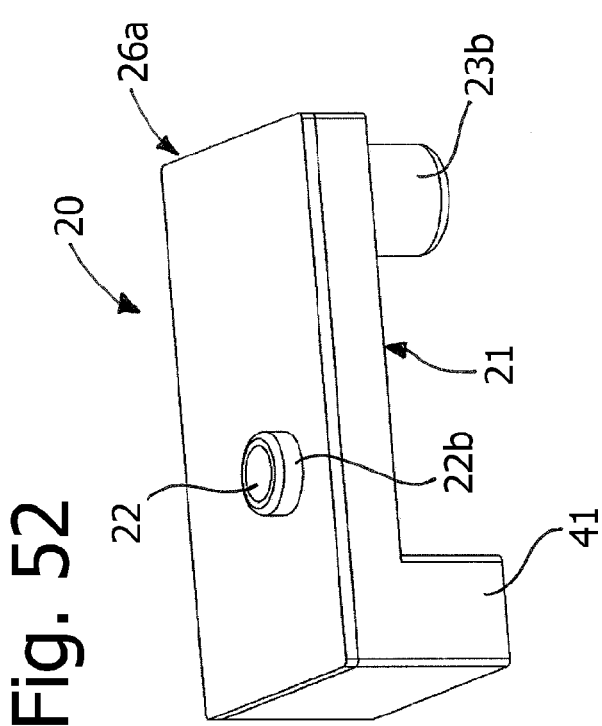
FIGS. 52 and 53 are perspective views from different angles of a part of a microfluidic device according to the invention.
Figure 53:
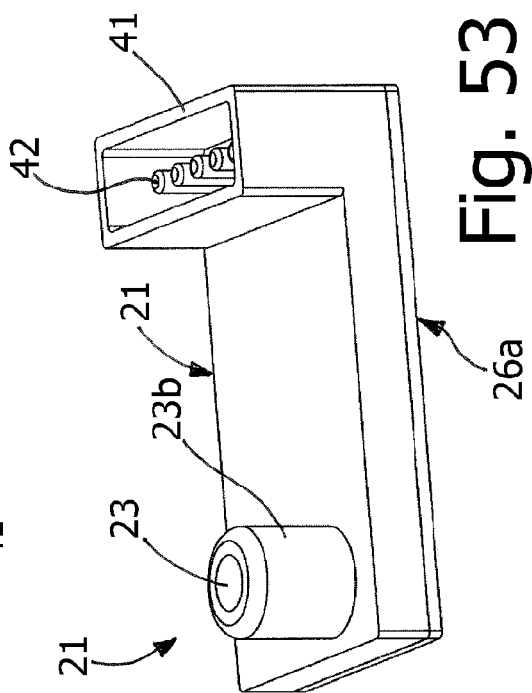

In one embodiment, such as the one represented in FIGS. 52-54, the body of the section 20 can also include a respective closing element, which integrates hydraulic-connection means. Also such an embodiment may be seen in FIGS. 52 and 54, where it may be noted how the lid 26*a* of the section 20 defines an upper connector 22*b*, which provides the inlet 22 of the section 20. The connectors of the section 20 could be arranged differently, just as the connector 41, and be in a number different from the one exemplified.

In one embodiment, the entire collection section 20 is configured as a unit that can be separated from the body 2 and is operatively coupled to the face of the body 2 opposite to the one in which the path 3 is defined. In such an embodiment, the outlet of the path 3 is preferably configured as through hole 5 of the body 2 and/or as hydraulic connector with respect to the connector 22*b*. In one embodiment, the section 20 has mechanical and hydraulic interconnection means, which can be coupled in a separable way with mechanical and hydraulic interconnection means of the first body 2.

The device represented in FIGS. 55-58 highlights both of these characteristics, which, on the other hand, do not necessarily coexist. In FIGS. 55-58 the same reference numbers as those already used previously are used to designate elements that are technically equivalent to the ones already described.

In the embodiment exemplified, the device MD does not comprise the lower body 30, and the body 2 has a general configuration similar to that of the body 2 of FIG. 36, but without the lower outlet connector 23*b*. In this case, defined in the face of the body 2 opposite to the one in which the path 3 is defined is a housing 33', in which there can be fitted at least partially, in a removable way, the collection section 20, as may be clearly seen from FIG. 56. In the example illustrated, the section 20 has a configuration similar to the one described with reference to FIGS. 52 and 53.

Also in this embodiment, preferably, the body 2 is made of a material that is at least in part elastic, with the section 20 that can then be mechanically and hydraulically coupled, in a fluid-tight way, with the body 2, in particular by exploiting the slight yieldingness or elasticity of the latter. As may be noted, in particular from FIG. 58, in the assembled condition of the device, the inlet connector 22b is fitted in the through hole 5 of the body 2, which provides at the same time both the outlet of the path 3 and a connector means co-operating with the connector 22b. As has been explained previously, in the hole 5 there may possibly converge also a duct 8 or 8' for the buffer, or else there could be provided respective further connectors in the body 2 and in the section 20.

In one embodiment of the invention, at least one of the inlets and the outlets of the microfluidic device has valve means, such as one-way valves and/or retention valves and/or anti-reflux valves. These valve means may be conveniently made integral in a body of the device MD, such as for example the body 2, or else be configured as additional components. FIGS. 59-62 and 63-67 illustrate these two possibilities.

In the case of the embodiment of FIGS. 59-60 the body 2, represented only schematically in cross section, with the corresponding lid 26, has lower connectors, such as the connectors 4b, 6b and 7b, defined within which is a membrane 45 having a transverse cut so as to define two opposite elastically deformable lips 45a, which mate in a fluid-tight way with one another. Membranes 45 of this sort may be provided also in the connectors 6b' and 23b, where envisaged.

The deformation in opening or closing of the lips 45a can be, for example, induced by the positive or negative pressure of the fluid entering the device (blood and/or buffer), or else of the outlet fluid (fluid with target particles and/or reject fluid, such as a mixture of reject blood and buffer).

Once said pressure ceases, or in the case of a negative pressure or counterpressure, the lips 45a tend to reclose automatically, also preventing exit of fluid. The sensitivity of said valves or lips can be predefined on the basis of the type of material and/or thickness of the membrane.

In another embodiment, the membrane 45 can also be without the aforesaid transverse cut, where preferably the membrane 45 has a pre-cut line or area and/or a perforation area. In a further embodiment, as highlighted in FIGS. 61 and 62, the apparatus of analysis, on which the device MD is to be set, may have fluid connectors 46, provided inside with suitable projections or pins 46a, preferably axial ones, having a thin section or in any case one such as to not prevent the flow of the fluid. The aforesaid pins 46a are designed to project inside the connectors 4b, 6b, 7b of the device MD until they bring about breaking or cutting of the membrane 45, with consequent formation and opening of the lips 45a, or else the pins 46a are designed to penetrate between the two lips with pre-formed cut, causing deformation thereof in opening.

In one such embodiment, the removal of the device MD from the apparatus then brings about closing of the lips 45a.

According to the aforesaid variant with breaking or cutting of the membrane 45, the pin 46a could advantageously be configured as a needle, in particular designed to perforate the membrane 45, which automatically recloses upon removal of the pin.

In the case of a use of the aforesaid valves as anti-reflux valves, i.e., ones designed to prevent a reverse flow, the fluid connectors 46 can be without the projections or pins 46a, and/or further valves can be provided, both for retention purposes and for anti-reflux purposes.

The embodiment of FIGS. 59-62 is, for example, advantageous in the case of a body 2 made of elastically deformable material, such as a silicone material. The valves prevent any leakage of fluid following upon removal of the device, after a fluid has been made to pass and/or prevent circulation of fluids in undesirable areas or directions.

FIGS. 63-67 refer, instead, to the case of valves, such as one-way valves and/or retention valves and/or anti-reflux valves, configured as additional components, applied in positions corresponding to lower connectors of the device MD. In this embodiment, the aforesaid valves, designated by 45' have a body made of elastic material, for example, elastomer material, with a flange-like base part, rising from which is a basically conical or frustoconical part, with a flattened top end and provided with a cut 45b (FIGS. 65-67) or with an area of predefined breaking, or cutting, or perforation. Also in such an embodiment, the divarication or closing of the flaps or portions of the membrane can be obtained by exploiting the pressure of the fluid and/or by inserting a pin or a needle.

It should be noted that also the valve means 45' can possibly be obtained integrally by moulding in the body 2.

The embodiments represented in FIGS. 59-62 and 63-67 regard integration of valves in lower inlets and/or outlets of a device MD, but it will be appreciated that the solution can be applied also to the case of a device MD provided with lateral and/or upper inlets and/or outlets.

Valve means are useful in order to prevent any leakage from the device MD when this is removed from an apparatus of analysis. Considering in fact that a biological fluid is made to flow in the device MD, it is preferable for the device itself not to leak during handling, the reason for this also being to maintain an isolated environment within the device, for example in the perspective of preserving the cells or of providing cultures within the section 20. Of course, the specific configuration of the valve means may be different from the one, albeit advantageous, exemplified herein.

Non-return valves or one-way valves can also serve on the inlets of the ducts 4 and 8 to prevent any reflux, for example in embodiments in which flows of blood and buffer are introduced into the device in an alternating way. In said perspective, even if first a part of blood is introduced and then the buffer, the buffer itself cannot "push" the blood backwards, towards tubes and supply reservoirs of the device, owing to the presence of the one-way valve means, for example of the type already described above.

In one embodiment, the collection section 20 is mechanically and hydraulically coupled in a separable way to the body 2 and has valve means, such as one-way valves and/or retention valves, preferably configured at least for preventing exit of material of the target sample from the corresponding inlet 22 and/or from the corresponding outlet 23, following upon removal and/or separation of the section itself from the body 2.

An example of such an embodiment is illustrated in FIGS. 68-71, where the same reference numbers as those of the previous figures are used to designate elements that are technically equivalent to elements already described above.

In this embodiment, the device includes a body 2 and a lid 26, of a configuration generally similar to that of the device MD of FIGS. 55 and 56. In this case, however, the outlet of the path 3 does not pass right through the thickness of the body 2, but consists, instead, of a duct 5 at least in part made in an internal area of the body 2; i.e., it extends between the upper face of the body 2, where the path 3 is defined, and the peripheral face of the body 2 itself.

Preferably, but not necessarily, defined in a position corresponding to the peripheral face of the body 2 in which the duct 5 opens is a positioning or housing seat, such as a flat. It should be noted, in any case, that the shape of the body 2 does not necessarily have to be circular, as in the case exemplified.

The body 21 of the collection section 20 has, by way of example, a shape similar to that of the section 20 of FIGS. 52 and 53, but with an inlet connector 22*b* that projects laterally, instead of at the top, and that is designed to fit into a connector or widened portion (see FIG. 70) defined at the end of the duct 5. The seal between the two coupled parts can be obtained advantageously exploiting the elasticity of the material constituting the body 2, when this is, for example, an elastomer or silicone material. There may in each case be envisaged purposely provided sealing means, such as a gasket.

It will hence be appreciated how, in one embodiment, the collection section 20 can be configured as component separable from the body 2, and have mechanical and hydraulic interconnection means, which can be coupled in a separable way with mechanical and hydraulic interconnection means of the body 2.

The section 20 is provided, at the inlet connector 22*b*, with valve means, preferably of the type previously designated by 45' in FIGS. 63-67. Similar valve means are envisaged at the outlet connector 23*b* of the section 20. Obviously, the valve means can be of a different type from the one exemplified.

It will be appreciated that, in this embodiment, once the sample of target particles has been obtained, the device MD can be removed from the laboratory apparatus that manages the flows (blood, buffer, discharge) and/or controls the device MD, and the section 20 can then be removed from the device MD, i.e., separated from the section 1, for subsequent use, for example analysis to be conducted with other equipment. The presence of the valve means 45' guarantees that, upon removal of the section 20 from the body 2, no material of the sample will be dispersed from the inlet connector 22*b* and outlet connector 23*b*, such as possible residue of the blood-buffer mixture with corresponding target particles. The reduced dimensions of the collection section 20 facilitate handling thereof during analysis.

In one embodiment the collection section 20 has at least one of an aeration passage, preferably mounted at which is an air-permeable membrane having calibrated porosity, and an inlet for introduction of a culture medium.

Also said embodiment may be seen in FIGS. 68-71, where the aforesaid aeration passage is designated by 47, preferably but not necessarily defined on the lid 26*a*, mounted at which is the aforesaid membrane, designated by 47*a*, for example made of Goretex®. In this embodiment, as inlet for the introduction of a culture medium there may advantageously be exploited the connector 22*b* provided with the valve means 45'. Obviously, there is nothing to rule out providing a specific inlet for the culture medium, for example, on the lid 26*a*, provided with suitable valve means, which are also of the type designated previously by 45.

Figure 72:
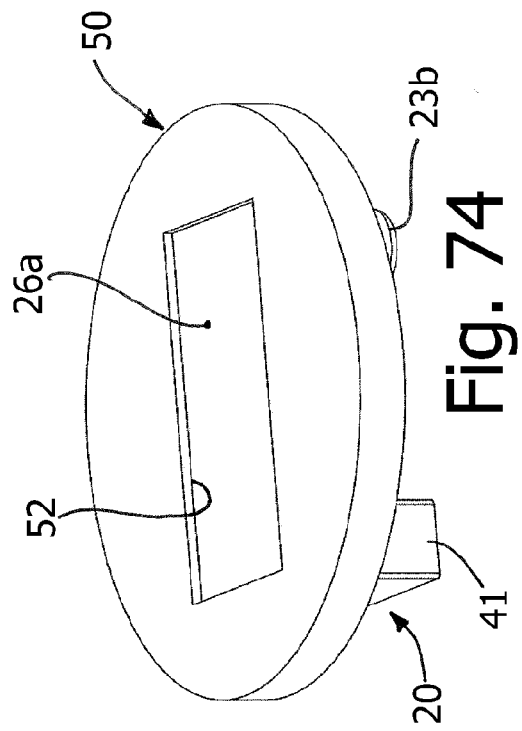
FIG. 72 is a perspective view of a variant of the part of FIG. 71.

FIG. 72 illustrates a variant of the collection section in which the aeration passage 47 is formed directly in the body 21, in a lateral position side, instead of on the lid 26*a*.

In one embodiment, which is particularly useful for the cases where the collection section of the device is separable/removable from or independent of the body 2, there may be provided a support or adapter, aimed at facilitating use and/or handling of the section itself.

Figure 74:
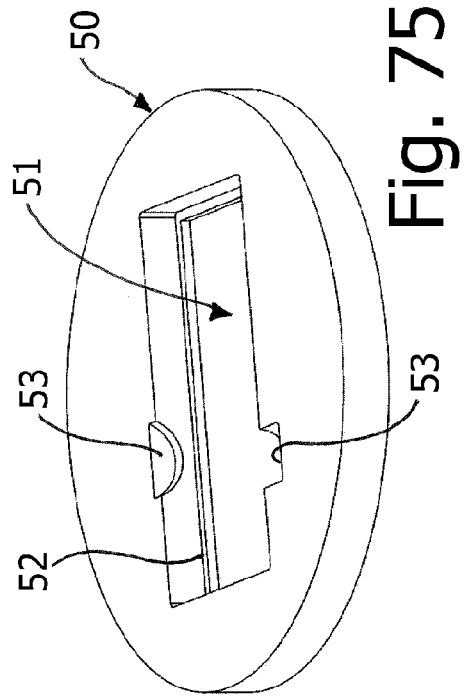
FIGS. 73 and 74 are perspective views, from different angles, of a part like the one illustrated in FIG. 72 coupled to a support or adapter.
Figure 73:
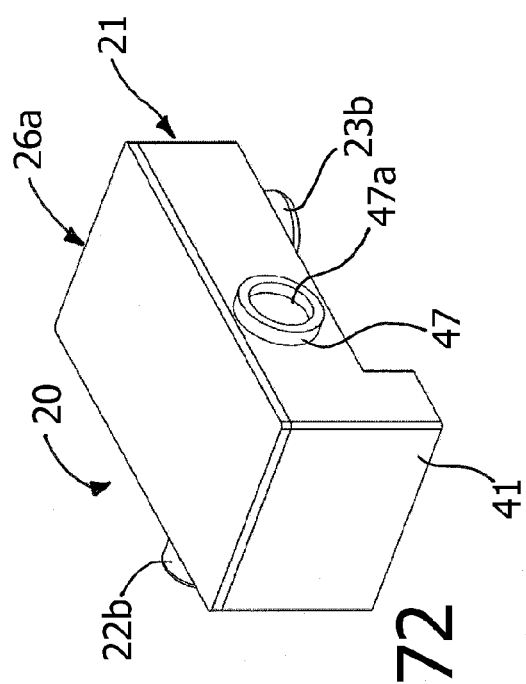
Figure 75:
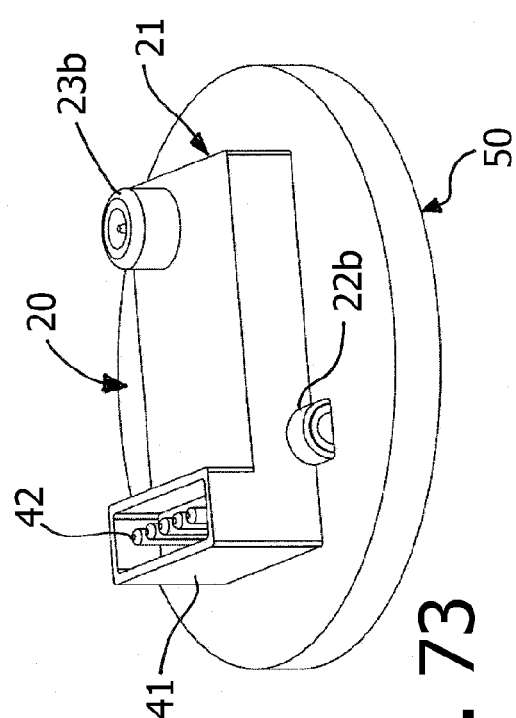
FIG. 75 is a perspective view of the support or adapter of FIGS. 73 and 74.

FIGS. 73-75 illustrate an example of support or adapter that can be used in combination with a separable collection section, such as the section 20 of FIG. 72. The support, designated as a whole by 50 has a body, made for example of plastic material, defined in which is a through cavity 51 having a peripheral profile congruent with that of the section 20 in question, i.e., a seat 51 designed to at least in part receive or house the section 20. Preferably, defined at an end of the cavity 51 is a step or undercut 52, on which a peripheral region of the lid 26*a* of the section 20 is designed to bear. In the case of sections 20 having one or more parts projecting laterally, such as the inlet connector 22*b* and the aeration passage 47, the cavity 51 is provided with lateral impressions 53 of a suitable shape, for receiving at least partially the aforesaid projecting parts. As may be appreciated from FIGS. 73 and 74, in the coupled condition of the components, the lid 26*a* of the section 20 is perfectly visible through the through opening 51 of the body of the support 50. On the opposite side, the connector body 41 with the terminals 42 is accessible.

The support 50 can conveniently have a circular outer shape, for its introduction in Petri dishes, or else the support 50 can have a shape designed to be mounted directly in apparatuses of the biomedical sector, such as a shape similar to that of a Petri dish. As may be appreciated, the use of the support 50 can prove in any case advantageous for simplifying the use and handling of the section 20, for example, on apparatus or instrument of analysis.

By way of indication, the section 1 (i.e., the body 2 when it is without the section 20) and/or the section 20 and/or the support 50 can have shapes in plan view and/or dimensions corresponding or close to at least one of the following:

a generally circular shape, with diameters comprised between approximately 35 and approximately 180 mm, such as for example one of the following diameters: 35 mm, 50 mm, 60 mm, 80 mm, 90 mm, 94 mm, 100 mm, 120 mm, 140 mm, 145 mm, 150 mm, 180 mm;

a generally quadrangular shape, with sides comprised between approximately 25 and approximately 120 mm, such as for example one of the following (side×side) 26 mm×76 mm, 100 mm×100 mm, 120 mm×120 mm.

It will be appreciated that, in various embodiments, the collection section 20—whether mounted on a support or not—constitutes in itself a microfluidic device, which can be used in itself, once separated from the body 2. This is in particular the case of collection sections 20 that integrate electrical and/or electronic and/or electromechanical devices of the type indicated previously, with corresponding interconnection and/or electrical-supply means (whether wired or wireless) and hydraulic connectors, as well as possible mechanical and/or electrical separation means. Hence, said sections 20, in addition to being usable as "slides" for visual analyses, for example under the microscope, may possibly be used on apparatuses of analysis provided with electrical and/or hydraulic interconnections that can be coupled with those of said sections.

Figure 76:
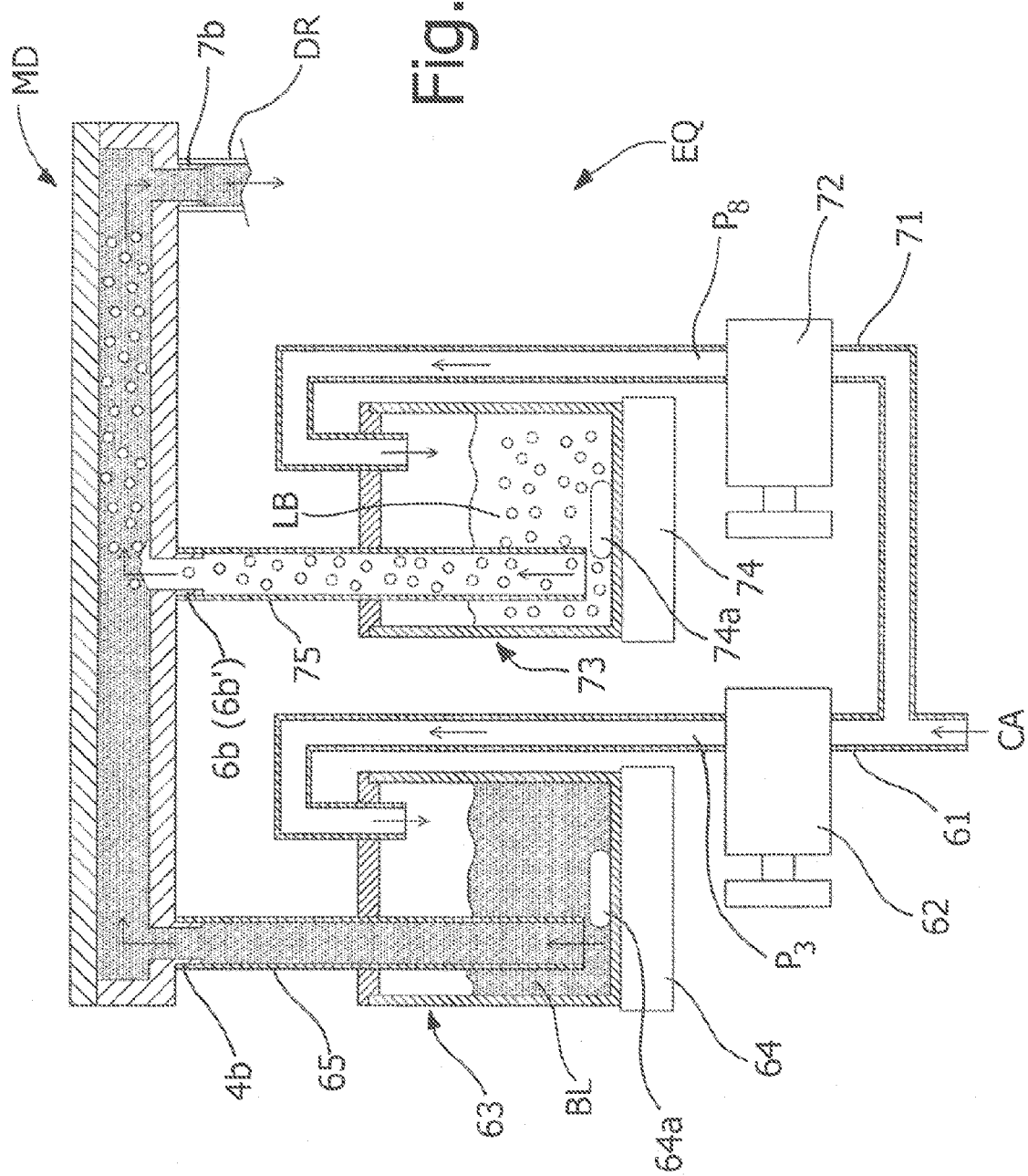
FIG. 76 is a simplified representation of an apparatus according to the invention, that can be used together with a microfluidic device, in particular for circulation and/or management of flows of fluids and/or control of the device itself.

FIG. 76 represents a principle diagram of a laboratory apparatus according to the invention that can be used in combination with a microfluidic device, for example a device having a mixed-flow separation structure or a device MD of the type described previously, in particular for circulation and/or handling of the flows of fluids and/or for control of the device itself.

The apparatus of FIG. 76, designated by EQ, is connected to a source of a fluid, preferably an aeriform AC such as compressed air, not represented, for supplying a first branch 61 and a second branch 71, operative along which are pressure-regulating devices suitable for the application, designated by 62 and 72, of a mechanical and/or electrical and/or electronic type, preferably precision pressure regulators, possibly programmable ones. In particular, said pressure regulators can be regulated in a pressure range comprised between 1 mbar and 1 bar, preferably between 10 mbar and 200 mbar.

According to one variant, operatively associated to the pressure regulators 62 and 72 are respective pressure sensors, not shown, for example in fluid communication with ducts or paths of the device MD, in particular in order to obtain a feedback and/or regulation of the pressure.

The compressed air AC at outlet from the regulators 62 and 72, to pressures $P_3$ and $P_8$, respectively, reaches respective hermetic containers 63 and 73, contained in which are a biological fluid, such as blood, and an auxiliary fluid, such as the liquid buffer; the pressures $P_3$ and $P_8$ are preferably comprised in a pressure range between 1 mbar and 1 bar, for example, a pressure range between 10 mbar and 200 mbar.

Preferably, but not necessarily, associated to the containers 63 and 73 are respective agitator means, in particular to maintain in suspension and/or in uniform distribution the particles and/or the possible beads, which may comprise, for example, a magnetic agitator 64 and 74, for example, designed to produce movement of at least one magnetic element or magnetic capsule 64a and 74a set in the containers 63 and 73, respectively.

An agitation or movement of the fluid could possibly be obtained via an appropriate excitation and/or movement of the beads dispersed in the fluid, obtained via appropriate excitation means, such as means designed to induce an electrical field.

The containers 63 and 73 have a respective outlet connected via a corresponding duct 65 and 75 to the respective inlet connectors 4b and 6b (or 6b') of the device MD. The outlet connector 7b of the device MD is connected to a discharge duct DR.

The containers 63 and 73 preferably comprise a respective casing 63a, 73a and a lid 63b, 73b coupled to one another in a fluid-tight way, possibly via appropriate additional sealing means. The lids 63b, 73b are preferably associated in a fluid-tight way to the respective ducts 61, 65 and 71, 75. Preferably, the inlet ducts 61, 71 extend in the respective casing 63a, 73a for a stretch or length shorter than the outlet ducts 65, 75. In particular, the ducts 61, 71 terminate at a higher level, close to the lower part of the lids 63b, 73b, whereas the ducts 65, 75 terminate at a lower level close to the lower part of the containers 63, 73, even if slightly raised to allow the fluid contained therein to flow away, or else are provided with appropriate openings close to said lower level. The ducts 61, 71 preferably terminate at the aforesaid higher level in order to prevent the compressed air AC from possibly forming bubbles or froth in the fluid contained in the corresponding container 63 or 73 and/or to prevent the risk of any reflux of fluid into the ducts for the compressed air. The apparatus could, however, function also with ducts 61, 71 arranged or terminating at different levels, i.e., longer inside the containers 63, 73.

In a normal operating cycle, the regulators 62 and 72 allow entry into the containers 63 and 73 of compressed air AC, at the pressures $P_3$ and $P_8$, so that the blood and the buffer, respectively, are introduced under pressure within the device MD.

As has been explained previously, preferably, the pressure $P_8$ is slightly higher than the pressure $P_3$, in order to prevent any reflux of blood from the duct 3 of the device to the duct 8. As already said, in any case, the pressures of the fluids at inlet to the device 1, such as the pressures $P_3$ and $P_8$, are preferably relatively low, i.e., of a value such as to reduce the risk of damage to or lysis of the particles or cells.

It should be noted that FIG. 76 presents a schematic configuration that can apply to any one of the devices MD, 1 and 20 previously described; it follows that the number of the ducts and/or of the attachments and/or of the containers and/or of the pressure regulators could vary, and the buffer could contain beads or be without them.

Consider moreover that what has been described for brevity with reference to a system designed to generate pressures could also refer to a system designed to generate negative pressures and/or differences of pressure, in particular between at least one inlet and at least one outlet of the device according to the invention. Likewise, what has been described for brevity with reference to a device functioning at positive pressures could also refer to a device operating with negative pressures and/or differences of pressure.

Figure 77:
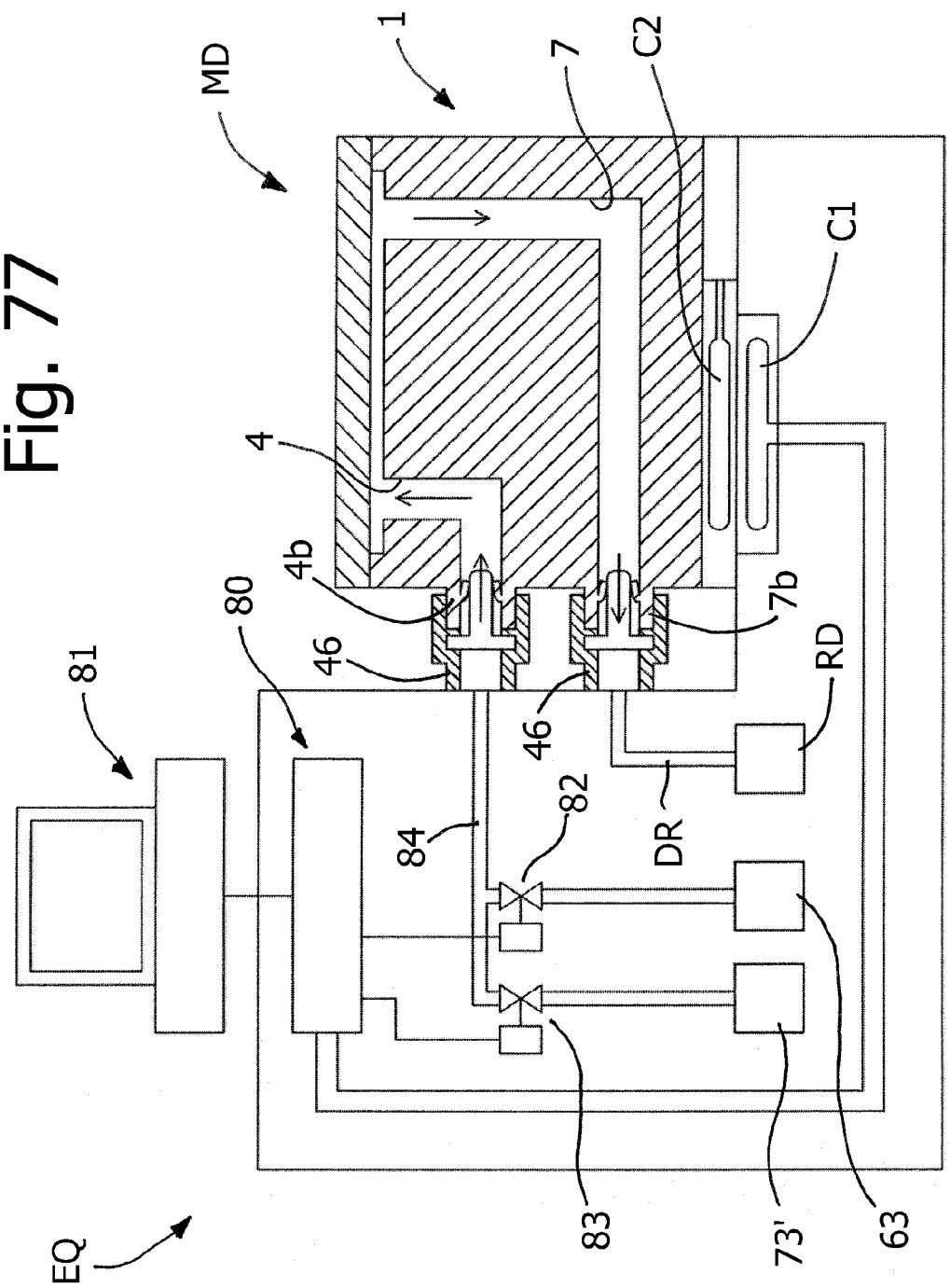

FIG. 77 illustrates another example of apparatus EQ according to the invention, of a type similar to the one shown in FIG. 76. In this schematic example (where for simplicity the source of compressed air and the corresponding pressure regulators have been omitted), the device MD is of the type with lateral connectors, provided with valve means of the type described with reference to FIGS. 59-60, and the apparatus EQ has connectors 46 of the type illustrated in FIGS. 61-62. It should be noted that also the hydraulic attachments 46 of the apparatus of FIG. 77 may possibly be provided with retention valves or valves for closing the ducts in the absence of the microfluidic device, for example to prevent any contamination or dispersion of fluid.

FIG. 77 highlights for simplicity just the connectors 4b for inlet of the blood and 7b for discharge of the reject mixture. The apparatus EQ is in any case conveniently provided with at least one further connector for the introduction of the auxiliary fluid (the buffer or the buffer with beads) into the device MD, provided for this purpose with the corresponding inlet connector, similar to the ones highlighted.

FIG. 77 represents schematically also a control system of the apparatus EQ, designated by 80, which can be connected to an external processor, such as a personal computer 81, for receiving and/or transmitting data, such as sending of data of configuration to the system 80 and/or for receiving from the system 80 results of analyses effected on the sample of target particles. The control system 80 supervises general operation of the apparatus, including management of the corresponding pressure regulators.

In the specific case represented, it may be noted how, in addition to the container 63 for the blood and a container RD for the discharge fluid, an additional container 73' is provided for a liquid, such as the aforesaid buffer or a further flushing buffer, both said containers being connected—by way of valves 82 and 83—to one and the same line 84 that supplies the connector 46 for inlet of the blood. This configuration is useful for the purposes of performing a step of flushing just with buffer of the device MD, at the end of collection of the sample of target particles in order to prevent any stagnation of blood inside the device itself and/or to push all the blood in circulation and cause it pass through the device MD. In practice, then, for the purposes of separation/collection of the sample of target particles just the valve 82, for delivery of the blood, is opened. At the end of said operating step, the valve 82 is closed, and just the valve 83 is opened to carry out a final flushing of the device MD with just buffer.

Of course, the hydraulic configuration of the apparatus EQ may differ from the one exemplified in FIG. 77; for example, it may be provided with a single container for the buffer and with suitable deviator means controlled by the system 80 for initially directing the buffer to the inlet 6, 6b of the path 8 of the device MD and, when the final flushing is to be performed, for directing the buffer, instead of the blood, to the inlet 4, 4*b* of the path 3. As may be appreciated, in this way, when the device MD is removed from the apparatus, absence inside it of deposits of blood is guaranteed and/or treatment of all the blood set in circulation is likewise guaranteed.

FIG. 77 moreover exemplifies a wireless communication and/or supply system set between the apparatus EQ and the device MD, for example for identification purposes, as has been explained previously. Designated by C1 is a winding and/or an antenna, forming part of the control circuit 80 of the apparatus EQ, and designated by C2 is a winding and/or an antenna integrated in the device MD, for example in its collection section (not represented in the figure), where said windings and/or antennas C1 and C2 belong to an arrangement of an RFID type. As is known, certain RFID arrangements include a passive device, i.e., one without battery or electrical supply (typically having transmitter or transceiver functions), bearing data and designed to react to a specific inductive electromagnetic field, produced by a respective reader, which supplies in response a modulated radiofrequency representing data. Since it does not have any internal source of energy, the aforesaid passive device derives its own supply from the electromagnetic field itself generated by the reader. Hence, in the case exemplified, following upon positioning of the device MD on the apparatus EQ, it is possible to set up a communication between them, without the need for any wiring and without having to provide the device MD with a battery of its own. According to a variant, the part of the RFID arrangement carried by the microfluidic device could, however, comprise a battery or a different electrical supply.

It should be noted that a circuit arrangement of the type indicated above can also be used for electrical supply and/or writing of data or information in suitable storage means present in the device MD, for example, data or information deriving or resulting from the analyses or tests effected on the laboratory apparatus.

FIG. 78 highlights an apparatus EQ according to the invention, altogether similar to that of FIG. 77, used in combination with a device MD having a different configuration of the microfluidic paths, which here extend on two opposite faces of the body 2.

FIG. 78 moreover highlights the presence of a cover, designated by 85, for enclosing the device MD in a protected and thermostatted environment TA, i.e., one designed to be kept at a substantially pre-set temperature (for example, by exploiting the means of the device MD itself previously designated by TS and/or EH in FIG. 46). Preferably, also the area of the apparatus EQ in which the containers 63, 73, 73', RD and the corresponding ducts are present is protected and/or thermostatted.

According to a variant, the device MD of FIG. 78 has a configuration in which the ducts and/or microfluidic paths are obtained on at least two opposed sides or faces of the device MD and/or of the body 2, preferably set in communication by through ducts or holes, provided with respective covers 26 (or 30).

FIG. 79 is a schematic illustration of an equipment EQ according to the invention, substantially configured as kit of parts, for handling the flows in a microfluidic device, for example a device MD of the type described previously, having purposes substantially similar to the ones of the equipment of FIG. 76, but of simplified construction and use. The figure represents a kit comprising:

a flexible tube 90;

a first connector 91 with a needle for connection of the tube 90 to the device MD;

a second connector 92 with two needles, for connection both of the tube 90 to a container or test tube 93 containing the blood (or the buffer) and for connection of the test tube 93 to a further flexible tube 94 for delivery of a fluid or compressed air; and a third connector 95 for connection of the tube 94 to a source of a fluid or compressed air 96 at a suitable pressure.

Preferably, at least part of the kit EQ of FIG. 79 is of a disposable type in order to prevent any contamination and/or for a greater practicality of use.

In the example illustrated, the connector 92 comprises two needles 92*a* and 92*b*, which are introduced into the test tube 93, in particular perforating an elastomer plug 93*a* thereof in order to enable a convenient connection free from any contamination. In the assembled condition, the two needles are set staggered with respect to the central axis of the test tube 93, and connected to the two respective hoses 90 and 94.

The test tube 93 is preferably—but not necessarily—a test tube of a standard type used in the sector, such as a test tube having an outer diameter of approximately 12.3 mm or 15.2 mm and an internal diameter of approximately 10.7 mm or 13.3 mm, respectively, the external diameter of the plug 93*a* being of approximately 15-16 mm and 16.5-17.5 mm, respectively.

According to an advantageous aspect, the connector 92 has dimensions such that it can be fitted or pressed on the test tube 93 and/or on the plug 93*a* via the two needles 92*a*, 92*b*. Preferably, the body of the connector 92 has a perimetral portion that surrounds at least in part the edge of the test tube 93 and/or of its plug 93*a*. In said perspective, for example, the internal diameter of the connector 92 can be equal to or slightly larger than approximately 12.3 mm or 15.2 mm, or approximately 15-16 mm, or approximately 16.5-17.5 mm, respectively. Preferably, in order to facilitate perforation of the plug 93 with the two needles of the connector 92, the plug itself has a central portion with reduced cross section.

In a way similar to what has been described with reference to FIG. 76, the flow of compressed air generated by the source 96 pushes on the blood into the test tube 93, forcing it into the device MD via the tube 90. A similar operation occurs obviously in the case of a container 93 containing the liquid buffer to be introduced into the device MD in parallel with the blood.

Considering the fact that, in the devices MD described herein with mixed-flow separation, fluids at a relatively low pressure are preferably used, the seals can be obtained easily and/or low-cost components or materials can be used. This applies, for example, for the seal between the needles 92*a* and 92*b* and the elastomer plug 93*a* of the test tube 93 and/or the seal between the elastomer plug 93*a* and the test tube 93 and/or the seal of the various connectors 91, 92, 95, and/or for the use of components of the kit made of plastic material.

In a variant, the tube 94 can be connected, for example at the end of the step of collection of the sample of target particles or an intermediate treatment step, to a source under pressure of a liquid buffer, instead of a source of compressed air, both in order to empty the test tube 93 completely from the blood and in order to eliminate the final residue of blood that might have remained within the device MD. In this way, there is the possibility of treating all or almost all of the blood introduced into the test tube 93. At the same time a flushing is obtained that, even though the device MD, the tubes 90, 94, the connectors 91, 92, and the test tube 93 are of a disposable type, enables a safer and cleaner handling and subsequent disposal of said components.

It should be noted that a flushing of the device MD of the type indicated previously may possibly be obtained by envisaging a purposely provided flushing accessory, to which the device itself is to be connected after analysis and/or after taking the sample of target particles out of the section 20.

As has been explained previously, the body 2 of the device MD according to the invention can be made at least of one of various materials, such as an elastomer or silicone material, a thermoplastic material, a glass, a semiconductor such as silicon.

Use of glass enables an excellent planarity to be obtained, as compared to an elastomer micromoulded item. On the other hand, as has been said, also in the case of a microprocessed elastomer body 2, the presence of the lid 25 and/or of the lower body 30 fixed—for example via gluing or bonding—to the body 2 enables the necessary planarity to be guaranteed.

In the case of use of glass an initial machining step is preferably envisaged (for example, lapping), in order to obtain a perfectly plane plate, on which to provide the microprocessed elements by etching (chemical etching, abrasion, laser etching, plasma etching, etc.), or possibly deposition, in order to form the walls and/or lateral delimitations of the paths 3, 8, 9.

In an example of said process, both the glass and the silicon can be machined as plane surfaces, on which a layer of protective material (such as a metal mask or a polymeric photoresist mask) is then positioned or deposited, which leaves free the paths to be obtained in the underlying material (glass or silicon), which is dug and removed via appropriate known processes, for example, chemical etching or microabrasion. The material in question, whether glass or silicon, can also be dug in other ways, for example, via laser or plasma etching.

In order to define the paths 3, 8, 9 and/or the lateral delimitations 10, 11 deposition techniques may also be used, for example, by depositing a material designed to form the walls and the lateral delimitations that delimit the various paths. Said deposition can be obtained with multiple known technologies, such as for example serigraphy or ink jet printing, considering that there exist inks of various types (metal-based, NPs, dielectric, doped and otherwise, semiconductor, using biological substances, etc.).

Amongst the various techniques that can be employed for producing a device MD wafer-bonding may be mentioned, which is suited for embodiments in which a first microfluidic circuit made of a first material (for example silicone or glass, for the body 2 or the body 21) is associated to a second microfluidic circuit made of a second material (for example silicon, for the substrate 40 of the section 20). The body 2 can also be obtained with a moulding process, including one or more steps of moulding and/or forming.

Figure 80:
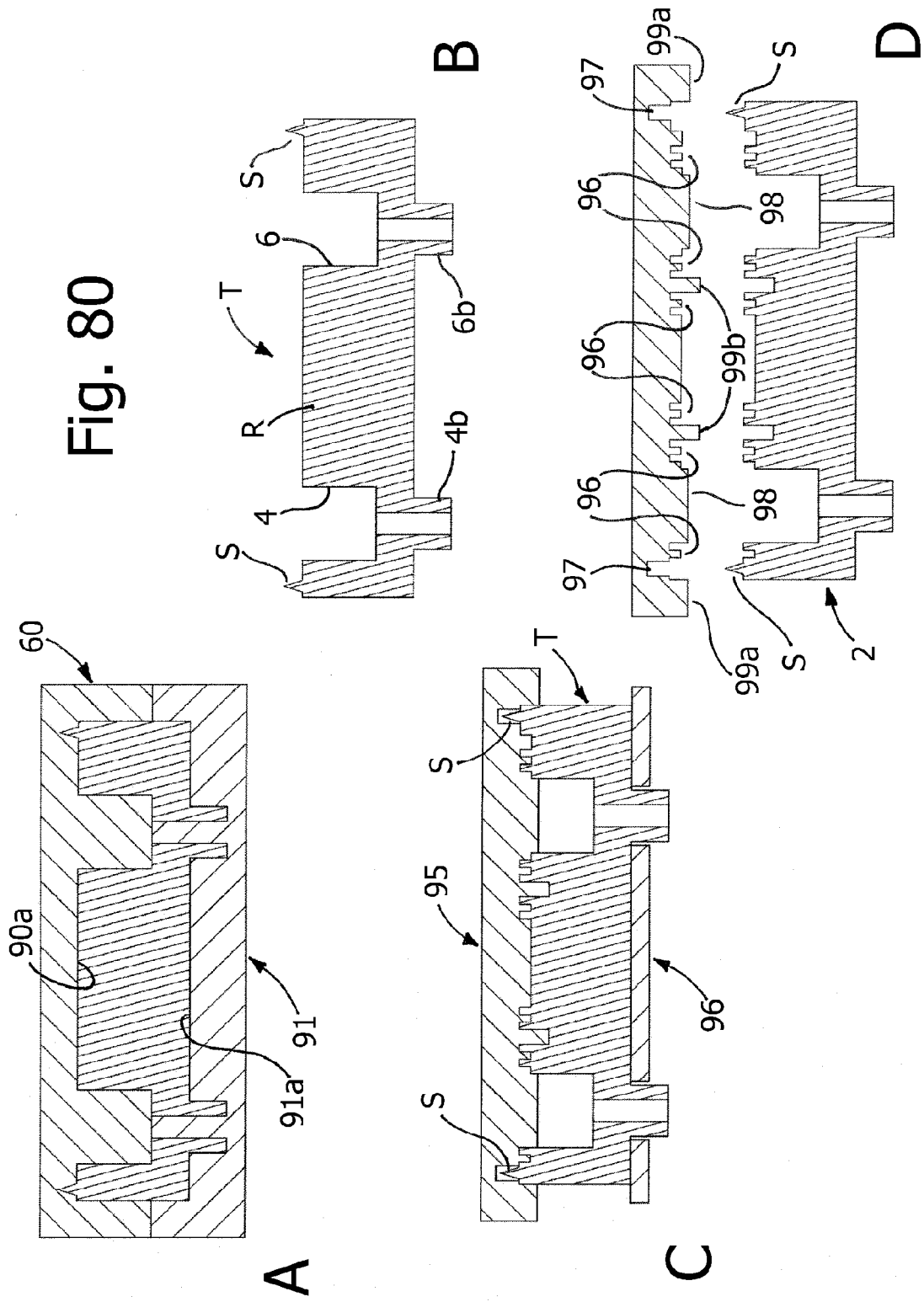
FIG. 80 illustrates in schematic form an example of process of moulding of a microprocessed body forming part of a microfluidic device according to the invention.

FIG. 80 is a merely schematic illustration of an example of a process for moulding a device according to the invention, such as a mixed-flow separation device. The example regards a moulding of a sub-micrometric imprinting type of a body 2 made of elastomer or silicone material, such as PDMS, or thermoplastic material, such as PMMA (polymethylmetacrylate).

Part A of FIG. 80 highlights the use of a first mould, including two half-moulds 90 and 91, having respective impressions 90a, 91a for definition of details of the body 2, preferably ones not having micrometric dimensions, such as for example the ducts 8, 9 and/or the corresponding hydraulic connectors 6b, 7b (see part B of Figure) and the seal elements or lips, such as of the perimetral lips S.

In the example, the impression 90a of the top half-mould 90 is also configured for providing at least one element in relief R, shaped in said first moulding step, aimed at providing a semifinished product, designated by T in part B of FIG. 80. Performed on the element in relief R are the micromouldings in a second moulding step, in particular using the imprinting technique.

The fluid-tight element S can be configured as a lip running along the perimeter of the body 2, for example for providing seal towards the outside with respect to a lid 26, such as a seal from inside, for example in regard to the hydraulic ducts, and/or a seal from outside, for example in regard to any infiltration of dirt into the device. Possibly, the element S and/or the element in relief R can undergo micromoulding processes in the aforesaid second moulding step, for example to change at least in part the shape thereof.

Once the semifinished product T, for example made silicone or thermoplastic material, has been obtained, this is introduced into further moulding or forming equipment, as highlighted in parts C and D of FIG. 80. This forming or imprinting equipment includes a top mould 95 and a counter-mould or bottom support 96. The mould 95 is provided with impressions 96, 99b that form at least the micro-mouldings of the upper surface or face of the semifinished product T. It should be noted that the equipment could be configured to enable simultaneous forming or imprinting on at least two different surfaces, such as two opposite surfaces; hence, with reference to the example illustrated, also the support 96 could be provided with imprinting impressions.

Preferably, the second mould 95 is provided with seats or cavities 97 designed to receive the element or elements formed in the first moulding step, such as the elements S and/or R and/or the ducts 4, 6 and/or the connectors 4b, 6b, so as not to damage them.

Once again preferably, the mould 95 necessary for forming the micromouldings has both projections 98 in the parts coinciding with "empty" regions of the piece T, and lateral shoulders 99a for containing the material during the second moulding step. The presence of the aforesaid projections and lateral shoulders prevents the material on which the micromouldings are obtained from deforming laterally, without offering a due mechanical resistance to compression and/or axial deformation exerted by the mould 95, in particular in the direction or along the axis of movement of at least part of the mould. In other words, at the moment of descent or axial movement of the mould 95 on the piece T, in particular for impressing the shape of the microfluidic paths, the material appropriately heated could yield elastically downwards and/or outwards, and in this case the mould 95 might be unable to impress adequately its own shape. The presence of the aforesaid shoulders and projections prevents this eventuality. Obviously, the extension downwards of the aforesaid projections and shoulders can be greater than the one exemplified in the figure.

Preferably, the mould 95 is provided with impressions 96, in particular ones of a smaller width and height, and impressions 99b, in particular ones of a larger width and height, which provide the micro-mouldings of the upper surface or face of the semifinished product T, such as respective microchannels of a smaller width and depth and microchannels of a larger width and depth, respectively (see, for example, what is described with reference to FIG. 3C).

By way of indication, the maximum width and height of the projections of the mould (and hence the depth and width of the paths/channels of the device) preferably fall within a ratio of approximately 30.

Consider that the various shapes or characteristics described with reference to the device of FIG. 80, performed in two process steps, could also be obtained with just a single process step, such as a step of moulding or a step of imprinting; for example, a body 2 as in part D of FIG. 80 could be obtained just with moulding or injection of material in a mould, in particular a mould provided with micrometric machinings or seats.

FIGS. 81-83 illustrate a further embodiment of a microfluidic device according to the invention. In said figures the same reference numbers as those of the previous figures are used to designate elements that are technically equivalent to the ones already described.

The device MD of FIGS. 81-83 is of a general conception similar to that of the devices described previously with a spiral configuration of the paths 3, 8 and 9 (see, for example, FIG. 22 or 36), but the corresponding idea may be applied also to devices MD having a different configuration. In this solution, the inlet 4 is made at the top of the body 2, and more in particular in the lid 26. In this embodiment, the inlet 4 is basically constituted by a hollow coupling provided in a region of the lid 26, which, in the assembled condition of the device, has its lower end facing an initial region of the path 3, delimited by a wall 2a''.

On said upper inlet 4 there can be fitted a container or reservoir 100 containing, for example, blood. For this purpose, the container 100 has a body 101 provided with a lower hydraulic attachment 102, preferably equipped with the retention means or valves of the type already described (not shown), or else with a closure designed to be perforated when it is fitted on the device MD. For this purpose, the connector of the device MD that provides the inlet 4 is shaped, in the example, like a needle.

The container 100 includes a top lid or plug 103, with a corresponding connector or attachment 104, preferably provided with said retention means or valves (not shown), in order to inject a fluid under pressure aimed at pushing the blood into the device MD. The thrust fluid can be, for example, compressed air and/or a liquid buffer. Once again by way of example, in a first step air can be injected and then, when all the blood has left the container 100, a liquid buffer can be injected. Possibly, for this purpose, level-sensor means can be associated to the container, for example, ones of an optical type, interfaced with an apparatus for analysis or management of supply of the flows to the device MD. Similar level-sensor means can be provided also for the further containers 63, 73, 93 described previously.

This solution eliminates or in any case considerably reduces the length of the path that the blood has to follow between a corresponding container and the device MD, in particular without the need for connection tubes. In this way, the amount of blood necessary for testing via the device MD may be reduced. The solution also prevents any stagnation of blood in the connection tubes that are typically envisaged for supplying known microfluidic devices, with the consequent possible errors in tests that require an analysis on predefined amounts of blood. There is moreover prevented the need to throw away each time also the tubes that are soiled with blood or other fluid being examined.

The device MD according to the embodiment proposed enables in fact the container 100 to be filled with a predefined amount of blood or other fluid, that is smaller if compared to the known art, and to cause it then to flow completely into the device MD, without any risk of stagnation.

In the example of embodiment, the container 100 is represented as a separate container, which can advantageously be filled apart and then fitted on the device MD. It will be appreciated, however, that, according to a possible variant, the container 100 can be directly associated to or integrated or made of a single piece in the device MD, in particular in its lid 26, possibly as reservoir obtained apart and then fixed or bonded or glued to the device MD.

A container having the same functions as the one previously designated by 100 can be advantageously integrated in the device MD, for example in the body 2 or in the lid 26, when it is made of elastomer. In an integrated container of this sort the blood can be introduced or injected (through a door or plug, or else injected by perforating a thin elastic closing wall, or via a retention valve of the type already described). Likewise, the air could then be injected into the container through an appropriate opening or a needle driven into said purposely provided perforatable wall. Considering that the pressures of thrust on the blood are relatively low, the elasticity itself of the elastomer material could guarantee the appropriate seals also during pressurization.

It will be appreciated that the solution of associating or integrating a container or reservoir to the device MD according to what has been described above applies also to the case where the same or a similar container is in fluid communication with a discharge outlet of the device itself, possibly even an outlet of the section 20. Said solution makes it possible, for example, to collect the reject liquid, and to dispose of it subsequently along with the body 2 or the section 20 (in case of integration), or else to have a separable collection reservoir so as to be able to dispose of said reservoir separately from the body 2 or the section 20.

Figure 84:
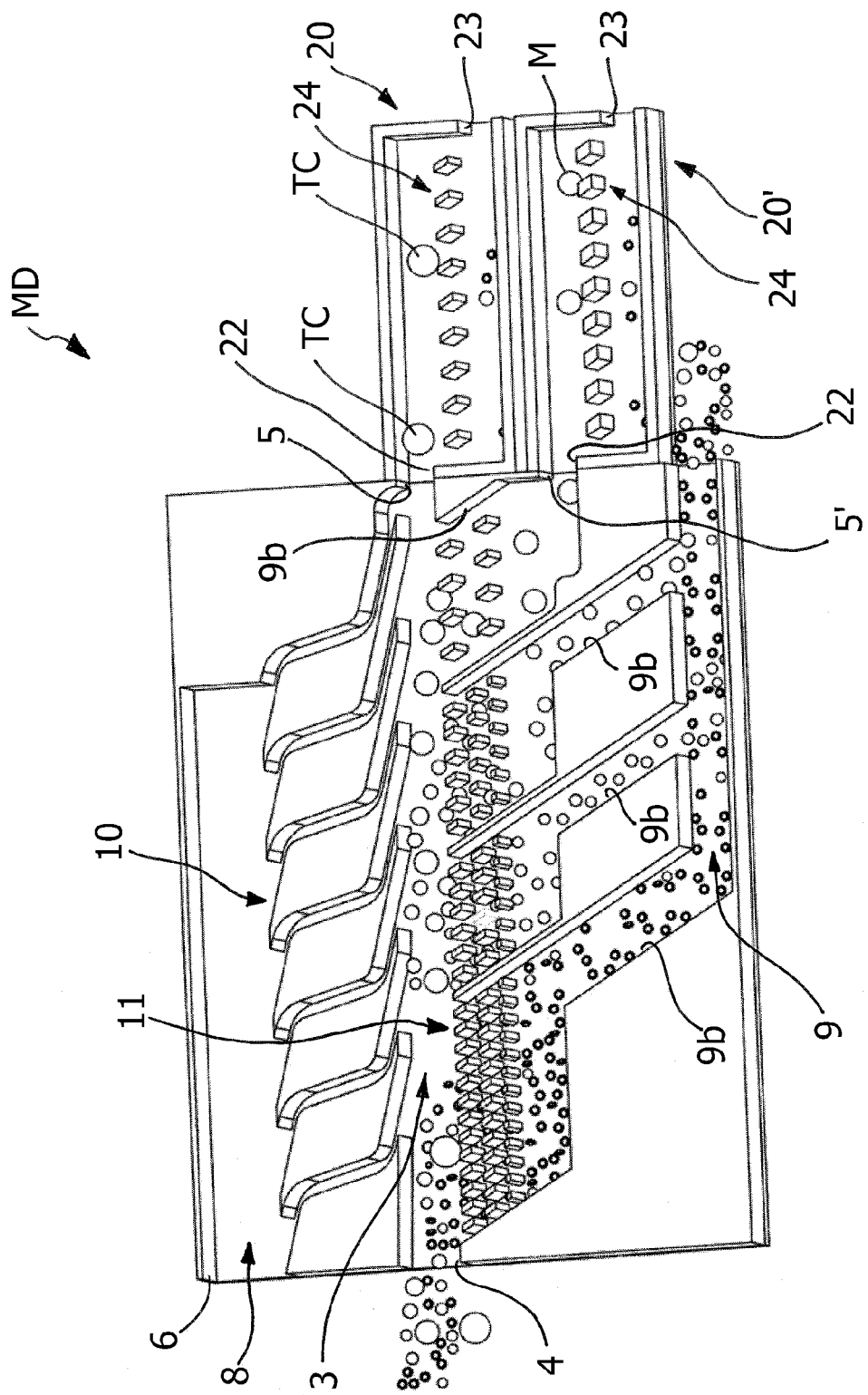
FIG. 84 is a partial and schematic perspective view of a further microfluidic device according to the invention.

FIG. 84 illustrates a further embodiment of the invention. The device MD of this figure is illustrated, merely by way of example, as having a structure similar to that of the device of FIG. 1, but the solution described in what follows may evidently be applied also to other configurations of microfluidic device.

In this embodiment, the device MD is provided with two collection sections 20 and 20', each of which is in fluid communication with a respective outlet 5 and 5' of the path 3 and/or of the device MD.

In the non-limiting example illustrated, the lateral delimitation 11, with the corresponding passageways, is configured for eliminating—as the fluid advances along the path 3—particles of progressively increasing dimensions and at the end isolate in the two sections 20, 20' larger particles, separated by size on the basis of the width of the passageways 11a of the last section of the lateral delimitation 11. In the example, the section 20 represented at the top is designed to collect tumour cells TC, whilst the section 20' represented at the bottom is designed to collect monocytes M.

Hence, in an embodiment of this type, the passageways 11a of the lateral delimitation 11 can be used as means for separation of target particles, for example tumour cells of different dimensions (see what has been said previously with reference to the preferred sizings of the passageways 11a, in the various sections or portions of the lateral delimitation 11).

Highlighted in the example are just two collection sections, but there is nothing to rule out adopting other configurations, with a greater number of sections 20, 20'. In addition, collection sections can be provided in various stretches of the lateral delimitation 11 distinguished by passageways having different dimensions, as has been explained previously. As may be noted in FIG. 84 (as likewise in FIG. 1), corresponding to each aforesaid stretch of the lateral delimitation 11 is a respective branch 9b for connection to the path 9. Unlike the case illustrated—where the branches 9b converge in a single channel—at the end of each of the branches 9b there could be connected in fluid communication a respective section 20 for collecting particles of different dimensions (possibly also rejecting the larger particles, in which case the outlet 5, or each outlet 5', would be an reject outlet of the device MD, not necessarily connected to a collection section).

The branches 9b and/or at least part of the passageways 11a can be devised as tortuous stretches or channels, prearranged for preventing a return flow from the path 9 to the path 3. In another embodiment, not represented, specific non-return means may be provided, such as one-way valve means, for example ones comprising membranes that bend in opening under the thrust of the flow from the duct 3 to the duct 9 and bend in closing in the presence of a thrust in the opposite direction. Said membranes may possibly be obtained by moulding and/or from the body 2, in the case where the body 2 is made of elastomeric or silicone material.

The case of FIG. 84 regards a configuration in which the two sections 20, 20' are connected to the path 3 substantially in parallel. It will, however, be appreciated that it is also possible to envisage a configuration with at least two sections connected in series one after another, i.e., with the outlet of a first section that is connected to the inlet of a second section. Obviously, in such a case, the passages of the separation means 24 of the first section will be wider than those of the second section.

The embodiment of FIG. 84 moreover highlights how, in one embodiment, the body 2 can be provided with just one duct 8, which can be used with a buffer with or without beads BE. Consequently, in the latter case, the separation of the particles will occur on the basis of just the size of the particles themselves, without the aid of beads.

It should moreover be noted that, in the example of FIG. 84, the section 20' corresponds to an "intermediate" outlet, with the larger particles that remain in the duct 3 and do not necessarily constitute the target particles. In the case where the use of the device MD is aimed at the collection of particles having an intermediate size (and not the larger ones), the outlet 5 of the duct 3 can be used as reject outlet (and hence without necessarily having to provide the section 20), with the outlet 5' that is, instead, connected to the section 20' for collection of the particles of interest.

As has been explained previously, the device MD according to the invention can be provided with a detection device, such as a particle counter, associated to the body 2 or to the section 20.

A device of this sort can be of an electrical type, i.e., with electrodes, or else of an optical type, i.e., with a transmitter and a receiver of light radiation, or again of an acoustic type, for example based upon the Doppler effect or the like. A principle diagram of such a particle counter is highlighted in FIG. 85.

Figure 85:
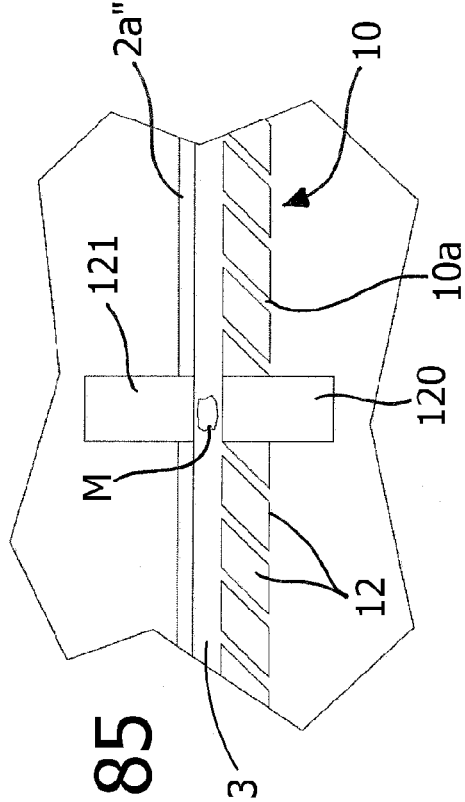
FIG. 85 is a schematic representation in plan view of a sensor or particle-counter system for a fluidic device according to the invention.

In the example of FIG. 85 the particles, including the target particles which here are assumed as being monocytes M, are made to pass individually in succession in a section that included a calibrated or capillary passage, on the two sides of which two electrodes 120 and 121 are located in opposed positions, in the case of an electrical particle counter. The section including the aforesaid calibrated passage can be, as in the example shown, a terminal stretch of the path 3, appropriately sized for enabling passage in succession of the target particles. A calibrated passage of this sort can in any case be defined along the path 3 or also within the section 20.

In operation, between the two electrodes 120, 121 a preferably constant electric current is made to flow. The passage of a particle between the electrodes 120 and 121 causes an alteration of the electric current that flows between the two electrodes, i.e., a variation of electrical resistance, enabling corresponding counting thereof. In general, the variation of current, or of resistance, will be proportional to the size of the particle, thus enabling detection of what type it is. The aforesaid variation can then be converted into a corresponding voltage pulse for each particle that has passed. Via a control logic the voltage amplitude of each pulse is then stored, where the different amplitude corresponds to a different size of the particle, so that finally the number of the cells differentiated on the basis of the size (i.e., the type) can be counted. An implementation of this sort can be facilitated if the conductivity of the circulating fluid is known. Conductivity ranges may be experimentally derived and stored in a control logic of the device MD. In any case, considering that in the terminal stretch of the path 3 the particles are for the most part dispersed in just the buffer, the characteristics of conductivity of the latter can be easily known beforehand. In said perspective, preferably, the buffer used has predefined physical and/or electrical characteristics, such as a known electrical conductivity. Preferably, the buffer has a predefined conductivity and characteristics such as to not damage any possible functionalized bonds and/or antibodies, in particular for the purposes of separation and/or detection of the particles.

It should be noted that the principle scheme of FIG. 85 can be applied also for the case of an optical detection device, in which case the elements designated by 120 and 121 will be, respectively, an emitter and a receiver of light radiation. In this case the buffer preferably has a good transparency to the optical signal.

In the case of an acoustic detection device, the elements 120-121 may consist of two transducers or else be replaced by a single transducer. For example, a single transducer can be devised for directing in the fluid sound energy, preferably wide-band ultrasound energy, operating both as transmitter and as receiver. A particle that comes to occupy the focal region of the transducer reflects the energy, generating an echo pulse proportional to the size of the particle.

The device according to the invention can further be provided with an arrangement or section configured for aligning the particles, i.e., arranging them substantially in a row one after another, for example for the purposes of a subsequent count via a particle counter.

Figure 86:
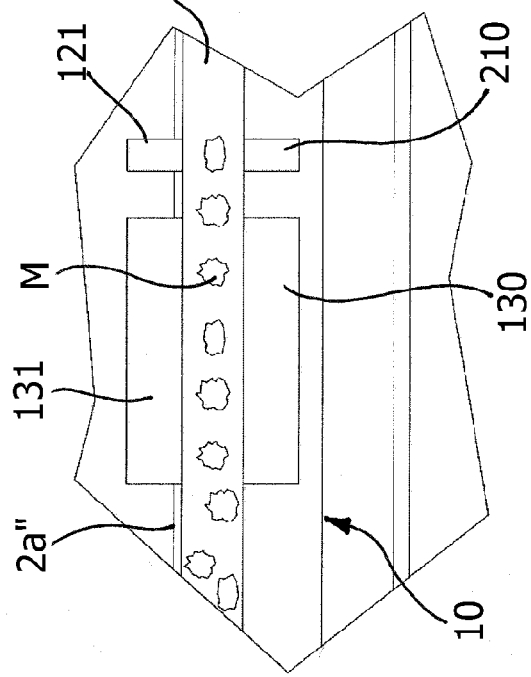
FIG. 86 is a schematic representation in plan view of a system for alignment of particles of a fluidic device according to the invention, in combination with a sensor or particle-counter system.

A schematic example of this type is illustrated in FIG. 86, in accordance with which the device MD has a section 130-131 for acoustic alignment of the particles, upstream of a detector device 120-121, which here is assumed as being a particle counter 120-121. The particle counter 120-121 can be of the type with (resistive or capacitive) electrodes, or else an optical counter, or again an acoustic counter, preferably distinct from the alignment system. The use of an alignment system, in the body 2 or in the section 20, enables, for example, counting of the particles also in ducts that are not necessarily capillary ones, i.e., with a width larger than that of the cell, in so far as the alignment is not performed by the duct, but via acoustic means.

In FIGS. 86, 130 and 131 designate the means designed for generating the acoustic alignment signal, for example in the form of opposed electrodes or transducers. In the example, the sections 120-121 and 130-131 are located along the path 3, for example in the proximity of its terminal portion, or else at the inlet 22 of the section 20. Preferably, the corresponding stretch of the lateral delimitation 10 is without passageways, in order to prevent in this stretch any turbulence that would annul alignment. Preferably, the buffer has characteristics such as to facilitate generation and/or propagation and/or detection of the acoustic signal.

Figure 87:
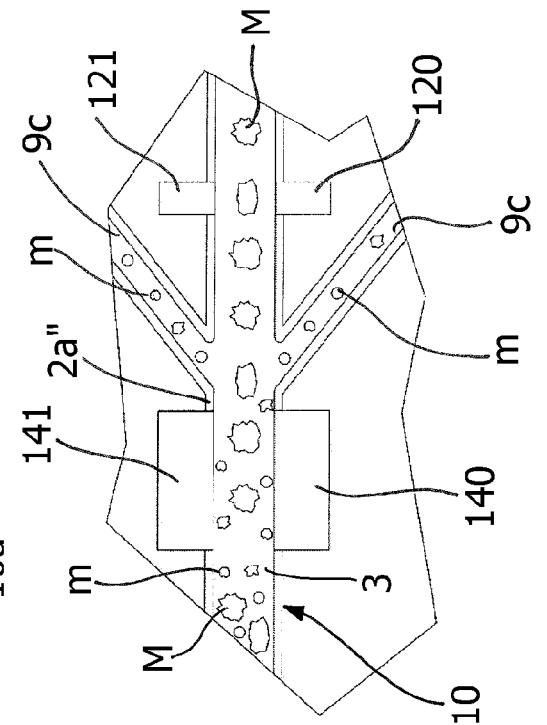
FIG. 87 is a schematic representation in plan view of an acoustic-separation system and/or particle sensor of a fluidic device according to the invention.

FIG. 87 illustrates, instead, the case of means for separating or displacing particles via acoustic waves. These means comprise, for example, a section including two acoustic transducers 140-141, such as electrodes of an appropriate shape or interdigitated, the separation system being preferably based upon the acoustic phoresis technique.

According to the principle of the acoustic phoresis, the large particles M are concentrated at the centre of the path 3, whereas the smaller particles, designated by m, are shifted to the sides of the path 3 so as to be then discharged in at least one peripheral duct, here two ducts designated by 9c, which preferably communicate with the discharge ducts 9 or 23.

Preferably, the transducers 140-141 are located in a first area of a microfluidic duct of the device MD, such as the path 3, whereas the detection means 120-121 are located in a second area of a microfluidic duct of the device MD, such as the path 3. In particular, the peripheral duct or ducts 9c are connected to said microfluidic duct 3 in an area comprised between said first area and said second area.

A section of the type illustrated in FIG. 87 can be used as refinement of the separation, i.e., after an initial separation has been conducted with a different method, such as a mechanical separation or filtration. For example, a system of acoustic phoresis can be used for separating the possible residual particles (such as erythrocytes or leukocytes that are not of interest) from the target particles.

It will be appreciated that, in various embodiments of the invention, the mixed-flow separation or filtering means including the corresponding lateral delimitations 10 and 11 with the corresponding paths 8 and 9 could be replaced by separation or filtering means according to other technical solutions or according to the known art, it remaining understood that other characteristics of the invention remain valid, such as for example the separability of the section 20, the provision of a collection section using a substrate made of semiconductor material, the use of separation and/or counting and/or alignment means of an electrical/electronic type, and equipment or kits for use in combination of the device.

As has been seen previously, the devices according to the invention, i.e., the device MD, considered as a whole, or its individual sections 1 and 20 considered separately, can integrate electrical and/or electronic components or arrangements, and in this case appropriate electrical-supply means are provided in regard to an external system, such as, for example, means for electrical connection to an apparatus of analysis.

According to an advantageous version of the invention, at least one of the sections 1 and 20 is provided with electrical-supply means that operate on the basis of a coupling a of wireless or pinless type, such as a coupling with galvanic insulation or with an induction of energy via coupled windings, comprising for example an antenna or a winding belonging to the device MD (section 1 and/or section 20) and an antenna or winding belonging to the aforesaid external system.

With reference to FIG. 77, a device according to the invention can be provided with a system comprising windings or antennas, which can be exploited both for supplying the electrical energy necessary for performing functions for transmitting and/or receiving data and for supplying the electrical energy necessary for carrying out at least one of the further electrical/electronic functions of the microfluidic device that have been described previously.

The configuration of the elements designated by C1 and C2 in FIG. 77 is suited to describing also the case where the elements C1 and C2 do not belong to a data-transmitter and/or data-receiver system, but to a power coupling of an inductive type (also known as "pinless power coupling") without any transmission of data in radiofrequency, of the type including a primary winding C1 shielded by a suitable insulating layer, for inductive coupling with a secondary winding C2.

Also in such an embodiment, then, the windings C1 and C2 enable supply of the electronic circuitry of the device MD, or of its sections 1 and/or 20, albeit without transmission or exchange of data. This solution can prove particularly useful, for example, for the section 20 of the device, which, also when it is separate from the body 2, can be supplied electrically in a convenient way. In this embodiment, then, the section 20 will comprise the antenna or secondary winding C2 and will receive the energy via the antenna or primary winding C1. The electrical supply thus provided can be used for carrying out the various electrical/electronic functions integrated in the section 20, for example for illuminating or exciting particles collected in the section itself, via an integrated optical source, or again for supplying electrical energy to a heater, for localized heating of the cells, for example for a cell culture.

The use of a wireless or pinless electrical-supply system moreover presents the advantage of enabling a fast and convenient handling of the device MD or of the sections 1 and/or 20, preventing the risk of rupture of electrical terminals following upon erroneous and/or forced insertion. In this regard it should be considered that the terminals for the connectors may be delicate, above all when they belong to miniaturized electrical connectors. A supply of a wireless or pinless type avoids the need for an electrical connector with the consequent risks of breaking thereof.

The antenna or winding C2 can be advantageously obtained on a printed circuit or PCB with which the section 2 or 20 is provided, as already exemplified previously, or again on parts made of insulating material of said sections, for example, glass or plastic, with techniques in themselves known, for example via serigraphy or deposition of conductive pastes. The antenna or winding referred to above can of course be integrated also in a silicon support of the device.

It should moreover be noted that a control circuit of the type previously designated by 80, 81 with reference to FIG. 77 can belong to a laboratory or analysis apparatus having functions different from the ones simplified, and hence apparatuses that not necessarily are designed for circulation of one or more fluids. Such a control circuit can, for example, be integrated in a viewing system or in a microscope, for example for detecting particles in the section 20 after it has been separated from the body 2, or else be integrated in an apparatus for support or storage of devices MD, or again be integrated in a cell-culture apparatus.

The mixed-flow separation technique has been described previously with reference to mixing of a buffer of the path 8 with a biological fluid or blood of the path 3. Consider, however, that, in order to implement the separation technique described, a portion of the same biological fluid or blood under analysis could be made to pass in the path 8. Also in such an embodiment, the auxiliary flow of blood of the path 8 is conveyed via the passageways 10a into the path 3 in order to mix with the other portion of blood, for the purposes already described, in particular for determining components of thrust, forces, or turbulent or irregular motions in the flow in the path 3. In said modality of use, then, the fluid to be treated or blood would be injected both into the inlet 4 that into the inlet 8.

It is clear that the microfluidic device described by way of example herein may undergo numerous variations by a person skilled in the branch, without thereby departing from the scope of the invention as defined in the ensuing claims.

The passageways 10a of the lateral delimitation 10 have been previously described with reference to a shape generally inclined with respect to the normal direction of flow in the path 3. However, in other embodiments of mixed-flow separation structures, the passageways 10a, or at least some of them, can have a different orientation or shape, for example be orthogonal or inclined in a direction opposite to the direction of the flow in the duct 3, as highlighted schematically in the areas designated by Z in FIG. 1. Also such a different configuration proves suited to inducing turbulence in the flow of the biological fluid of the duct 3, following upon introduction therein, via said passageways 10a, of a flow of an auxiliary fluid, whether this be a buffer or blood.

The invention claimed is:

1. A microfluidic device for separating at least one sub-population of particles from a fluid, the device having:
    a first microfluidic path for a first fluid, the first microfluidic path being defined in a first body of the device and extending at least in part between a first inlet for introduction of the first fluid in the first microfluidic path and a first outlet for discharging from the first microfluidic path a fluid sample enriched in a first sub-population of particles, the fluid sample being a first fraction of a mixture formed by the first fluid and an auxiliary fluid;
    a second inlet for introduction of the auxiliary fluid that is to mix with the first fluid, and a second outlet for discharging a second fraction of the mixture formed by the first fluid and the auxiliary fluid, the second fraction of the mixture containing at least one second sub-population of particles, the particles of the at least one second sub-population being smaller in size than the particles of the first sub-population;
    wherein the first path is defined in the first body between a second microfluidic path and a third microfluidic path, the second microfluidic path being in fluid communication with the second inlet to receive the auxiliary fluid and the third microfluidic path being in fluid communication with the second outlet or discharging the second fraction of the mixture;
    wherein the first microfluidic path is delimited laterally with respect to the second microfluidic path and the third microfluidic path by a first lateral delimitation and a second lateral delimitation, respectively, the first lateral delimitation having two opposite longitudinal ends and first passageways which connect the second microfluidic path to the first microfluidic path, the second lateral delimitation having two opposite longitudinal end and second passageways which connect the first microfluidic path to the third microfluidic path;
    wherein the first lateral delimitation comprises at least one array of first barrier elements upwardly protruding from an upper surface of the first body of the device, the first barrier elements being spaced from one another in a lengthwise direction of the first lateral delimitation to define each of said first passageway between two adjacent first barrier elements;
    wherein the second lateral delimitation comprises at least one array of second barrier elements upwardly protruding from the upper surface of the first body of the device, the second barrier elements being spaced from one another in a lengthwise direction of the second lateral delimitation to define each of said second passageways between two adjacent second barrier elements;
    wherein the second passageways have a size greater than the size of the particles of the at least one second sub-population and small than the size of the particles of the first sub-population,
    and wherein the first microfluidic path, the second microfluidic path, the third microfluidic path, the first lateral delimitation, the second lateral delimitation, the first passageways and the second passageways are arranged in such a way that a flow of the auxiliary fluid entering the first microfluid path from the second microfluidic path via the first passageways contributes to force particles of the at least one second sub-population to pass into the third microfluidic path along with said second fraction of the mixture, while the particles of the first sub-population are constrained by the first lateral delimitation and the second lateral delimitation to flow in the first microfluidic path along with the first fraction of the mixture up to the first outlet.

2. The device according to claim 1, wherein each of the first lateral delimitation and the second lateral delimitation has a length defined by the two opposite ends thereof and wherein the first passageways and the second passageways are distributed along most of the length of the first lateral delimitation and the second lateral delimitation, respectively, for introducing in a distributed way the auxiliary fluid from the second microfluidic path to the first microfluidic path, and for evacuating in a distributed way the second fraction of the mixture from the first microfluidic path to the third microfluidic path.

3. The device according to claim 1, further comprising at least one of:
    a section for collection of said first fraction of the mixture, having a respective inlet in fluid communication with the first outlet, a respective outlet opening and elements for separating the particles of said first sub-population from said first fraction of the mixture upstream of said respective outlet opening, or
    a section for collection of said second fraction of the mixture, having a respective inlet in fluid communication with the at least one second outlet, a respective outlet opening and elements for separating the particles of said second sub-population from said second fraction of the mixture upstream of said respective outlet opening.

4. The device according to claim 3, wherein the section for collection is configured as a distinct unit which is separable from the first body, the section for collection comprising
    a second body which is mechanically and hydraulically coupled in a separable way with the first body, the second body having at least one of an electric interconnection, a mechanical interconnection and a hydraulic interconnection couplable in a separable way with a respective electric interconnection or mechanical interconnection or hydraulic interconnection of the first body.

5. The device according to claim 4, wherein the section for collection includes a device made of semiconductor material, the device made of semiconductor material integrating at least one from among a fluidic means, an electromechanical device, an electrical device, an electronic device in miniaturized form, a device for transmitting and/or receiving signals, a device of a MEMS type, or a device of a NEMS type.

6. The device according to claim 1, wherein at least one longitudinal portion of the first microfluidic path has a decreasing cross section and extends between
    a longitudinal portion of the second microfluidic path having decreasing cross section and
    a longitudinal portion of the third microfluidic path having an increasing cross section path.

7. The device according to claim 1, wherein at least one of said first inlet, said first outlet, said second inlet, or said second outlet has valve means associated thereto.

8. The device according to claim 1, wherein the first, the second and the third microfluidic paths have a development which is at least in part substantially spiral-shaped.

9. The device according to claim 1, wherein at least one of the first inlet, the second inlet, the first outlet and the second outlet are located in a region of the first body about which the first, the second and the third microfluidic paths are wound up or develop in a spiral.

10. The device according to claim 1, further comprising a closure body superimposed to the first body and having an inner surface facing a bottom of the first, wherein the second and the third microfluidic paths, the first barrier elements and the second barrier elements have upper sealing elements cooperating with the inner surface of the closure body to form a seal therewith.

11. The device according to claim 1, wherein at least one of a lower supporting body and an upper closure body is associated to the first body, the at least one of the lower supporting body and the upper closure body including a printed circuit.

12. The device according to claim 1, wherein one of the first lateral delimitation and the second lateral delimitation comprises a plurality of said arrays of barrier elements.

13. The device according to claim 1, wherein the first body defines a housing in which a section for collection of at least one said sub-population of particles is at least partially inserted.

14. The device according to claim 1, wherein at least one of the first microfluidic path, the second microfluidic path and the third microfluidic path has two longitudinal portion having different depths.

15. A biomedical microfluidic device for separating a sub-population of particles from a biological fluid, the device having:
a first microfluidic path for a first fluid, the first microfluidic path being defined in a first body of the device and extending at least in part between a first inlet and a first outlet for defining at least one direction of flow;
at least one second inlet for introduction of an auxiliary fluid that is to mix with the first fluid, and at least one second outlet, for discharge of a first fraction of a mixture formed by the first fluid and by the auxiliary fluid;
wherein the first microfluidic path is defined in the first body between a second microfluidic path and a third microfluidic path, at least part of which is adjacent in length to a part of the first microfluidic path, the second and third microfluidic paths being in fluid communication with the at least one second inlet and the at least one second outlet, respectively,
wherein the first microfluidic path is delimited laterally with respect to the second microfluidic path and the third microfluidic path by a first lateral delimitation and a second lateral delimitation, respectively, the first lateral delimitation having two opposite ends and first passageways which connect the second microfluidic path to the first microfluidic path and the second lateral delimitation having two opposite ends and second passageways which connect the first microfluidic path to the third microfluidic path,
wherein at least one from among the first microfluidic path, the second microfluidic path, the first lateral delimitation and the first passageways is configured in such a way that a flow of the auxiliary fluid introduced into the first path from the second path forces particles or aggregates of particles having a dimension smaller than a dimension of the second passageways to pass into the third microfluidic path,
wherein each of the first lateral delimitation and the second lateral delimitation has a length defined by the two opposite ends thereof and wherein the first passageways and the second passageways are distributed along most of the length of the first lateral delimitation and the second lateral delimitation, respectively, in such a way that the auxiliary fluid is introduced from the second microfluidic path to the first microfluidic path along most of length of the first lateral delimitation and a second fraction of the mixture including said particles or aggregates of particles having a dimension smaller than a dimension of the second passageways is evacuated from the first microfluidic path to the third microfluidic path along most of length of the second lateral delimitation.

16. A microfluidic device for separating a sub-population of particles from a biological fluid, the device comprising:
a first module having a first body provided with first elements for causing a substantially mechanical filtration of the biological fluid, the first elements including at least one first microfluidic path, defined at least partly in the first module and having a first inlet, for introduction of the biological fluid in the first microfluidic path, and at least one outlet for discharge of a fluid sample enriched in said sub-population of particles, the first microfluidic path extending at least in part between the first inlet and the first outlet for defining at least a direction of flow;
a second module comprising electrically supplied elements, the second module having a second body with a respective inlet, in fluid communication with one of said first microfluidic path and said at least one outlet of the first module, the electrically supplied elements including at least one of a second element for causing a filtration of the fluid sample, a micro-fluidic element, an electro-mechanical element, an electric device, a miniaturized electronic device, an electric/electronic detection element, an element for transmission and/or reception of signals, a MEMS-type element, or a NEMS-type element,
wherein the first module and the second module are configured as units distinct from each other and mutually coupled in a separable manner, the first body of the first module being mechanically and hydraulically coupled in a separable way with the second body of the second module, the first body having at least one of a mechanical connection arrangement and a hydraulic connection arrangement coupled in a separable way with a corresponding mechanical connection arrangement or hydraulic connection arrangement of the second body,
in such a way that once said sub-population of particles has been collected in the second module, the second module is separable from the first module by uncoupling said at least one connection arrangement of the second body from the at least one corresponding connection arrangement of the first body.

17. The device according to claim 16, wherein the second body comprises a casing body housing a device made of semiconductor material and integrates at least partially at least one of hydraulic ducts and electric connection elements connected to the device made of semiconductor material.

18. The device according to claim 16, wherein one of said first module and second module comprises at least one of:
an arrangement for applying an electric field or an acoustic signal capable of inducing a displacement of particles present in one of the biological fluid and the fluid sample;
an arrangement to induce agitation or turbulence of functionalized particles added to the biological fluid;
an arrangement for subjecting functionalized particles added to the biological fluid to attraction or repulsion forces by means of electrical fields;
an arrangement for performing a detection of characteristics of particles present in one of the biological fluid and the fluid sample;

an arrangement for performing a counting of particles present in one of the biological fluid and the fluid sample;

an arrangement for obtaining an alignment of particles present in one of the biological fluid and the fluid sample.

19. The device according to claim 16, also comprising at least one of an integrated circuit, a device for measuring and/or processing information, a lighting device, an excitation device, an optical detection device, a memory device, a device for counting particles, or a sensor device.

20. The device according to claim 16, wherein the second module has a valve arrangement, configured for preventing outflow from the corresponding inlet of the fluid sample, following upon separation of the second module from the first module.

* * * * *